(12) United States Patent
Purandare et al.

(10) Patent No.: US 8,445,676 B2
(45) Date of Patent: May 21, 2013

(54) PYRROLOTRIAZINE KINASE INHIBITORS

(75) Inventors: Ashok Vinayak Purandare, Pennington, NJ (US); David B. Frennesson, Naugatuck, CT (US); Muthoni G. Kamau, Lawrenceville, NJ (US); Lalgudi S. Harikrishnan, Skillman, NJ (US); Mark G. Saulnier, Higganum, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 29 days.

(21) Appl. No.: 13/123,305

(22) PCT Filed: Oct. 8, 2009

(86) PCT No.: PCT/US2009/059945
§ 371 (c)(1),
(2), (4) Date: Jun. 29, 2011

(87) PCT Pub. No.: WO2010/042684
PCT Pub. Date: Apr. 15, 2010

(65) Prior Publication Data
US 2011/0294816 A1    Dec. 1, 2011

Related U.S. Application Data

(60) Provisional application No. 61/103,620, filed on Oct. 8, 2008.

(51) Int. Cl.
*C07D 487/04* (2006.01)
*A61K 31/53* (2006.01)
*A61P 35/00* (2006.01)

(52) U.S. Cl.
USPC .......................................... 544/183; 514/243

(58) Field of Classification Search .... 544/183; 514/243
See application file for complete search history.

(56) References Cited

U.S. PATENT DOCUMENTS

| | | | |
|---|---|---|---|
| 7,531,539 B2 * | 5/2009 | Fink et al. | 514/243 |
| 7,534,792 B2 * | 5/2009 | Wittman et al. | 514/243 |
| 7,879,855 B2 * | 2/2011 | Wittman et al. | 514/243 |
| 8,263,765 B2 * | 9/2012 | Wittman et al. | 544/183 |

FOREIGN PATENT DOCUMENTS

| WO | WO 2008/021924 | 2/2008 |
|---|---|---|
| WO | WO 2009/111531 | 9/2009 |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Piccaluga et al., Expert Opinion in Biological Therapy, 7(10), 1597-1611, 2007.*
Golub et al., Science, 286, 531-537, 1999.*
Cecil Textbook of Medicine, edited by Bennet, J.C., and Plum F., 20th edition,vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*

* cited by examiner

*Primary Examiner* — Venkataraman Balasubramanian
(74) *Attorney, Agent, or Firm* — Elliott Korsen

(57) ABSTRACT

The present invention provides compounds of formula I

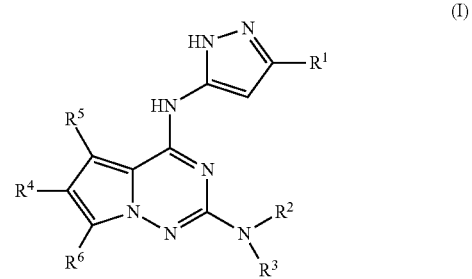

and pharmaceutically acceptable salts thereof.
The formula I compounds inhibit tyrosine kinase activity of such as Jak2 and CK2, thereby making them useful as antiproliferative agents for the treatment of cancer and other diseases.

10 Claims, No Drawings

PYRROLOTRIAZINE KINASE INHIBITORS

RELATED APPLICATION

This application claims a benefit of priority from U.S. Provisional Application No. 60/103,620, filed Oct. 8, 2008, the entire disclosure of which is herein incorporated by reference.

FIELD OF THE INVENTION

This invention relates to novel compounds that are useful as anti-cancer/antiproliferative agents. This invention also relates to a method of using the compounds in the treatment of proliferative diseases, such as cancer, and to pharmaceutical compositions containing the compounds.

BACKGROUND OF THE INVENTION

Protein kinases play a critical role in signal transduction for several cellular functions including cell proliferation, carcinogenesis, apoptosis, and cell differentiation. Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Protein kinases that have been implicated in these processes include Abl, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB, SRC, CK2 and VEGF. Hence, there is an ongoing need to investigate novel compounds that can be used to regulate or inhibit tyrosine kinase enzymes. Inhibitors of protein kinase enzymes may be used to treat diseases which are characterized by an overexpression or upregulation of tyrosine kinase activity such as cancer, diabetes, restenosis, arteriosclerosis, psoriasis, angiogenic diseases and immunologic disorders (Powis, G.; Workman P. Signaling Targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. In general, RTKs are activated by ligand-induced oligomerization and tyrosine autophosphorylation of specific intracellular substrates such as PLCγ, PI3 kinase, ras, and raf/MEK/Erk1. Tyrosine kinase activity is an absolute requirement for signal transduction through this class of receptor.

The Janus kinases (Jaks) modulate proliferation, survival and differentiation of a variety of cell types through integrating the signal transduction mediated by cytokine receptors. The Jak family of tyrosine kinases is comprised of the four family members, Tyk2, Jak 1, Jak2 and Jak3. This kinase family shares several structural features including several Jak (JH) homology domains. The carboxy terminal JH1 domain contains the active kinase domain adjacent to a pseudokinase JH2 domain. Amino terminal to these domains are JH3-4 and JH5-7, which encode a domain similar to a SH2 and FERM domains, respectively. The SH2-like domain is not well characterized functionally amongst the Jak family members whereas the FERM domain, comprised of JH5-7, has been shown to mediate binding to cytokine receptors. Cytokine receptors are devoid of an intrinsic kinase activity and upon ligand binding, Jak family members are recruited to these receptors and are activated to phosphorylate tyrosine residues on the receptor complex and to downstream signaling molecules. A key downstream mediator of cytokine receptor signaling is the signal transduction and activator of transcription (STAT) proteins. There are seven mammalian STAT proteins (STAT1, 2, 3, 4, 5a, 5b, 6 and 7) which integrate signaling downstream of cytokine receptor activation. Upon recruitment to the cytokine receptor-Jak complex, STATs are tyrosine phosphorylated at the carboxy terminus by the Jak kinases. This phosphorylation results in the formation of STAT homo- or heterodimers through phosphorylated tyrosine and SH2 domain interactions. After activation through dimerization, the STAT proteins translocate the nucleus where they bind a response element in promoters to activate transcription of key genes involved in proliferation and differentiation. In addition to STAT regulation, Jak activation has also been reported to regulate other key growth/survival pathways including those mediated by IRS-1, Ras-MAPK, PI3K and Src kinase.

Alterations in Jak signal transduction has been reported in a variety of diseases. In leukemias, chromosomal rearrangements (Tel-Jak2) producing a constitutively active Jak kinase have been observed in atypical chronic myeloid leukemia. Activating point mutations have been observed in Jak3 in acute megakaryoblastic leukemia and Jak2 in acute myelogenous leukemia and in myeloproliferative disorders such as polcythaemia vera, essential thrombocythemia and myeloid metaplasia. Recently JAK2 mutation (JAK2 V617F) was shown to be responsible for variety of myeloproliferative diseases like polycythemia vera, essential thrombocytopenia and myelofibrosis. A role for Jak kinases in solid tumors is also supported by the large number of reports of constitutive Stat3 activation in a wide variety of cancers. Elevated or constitutive STAT3 activity has been observed in breast, prostate, head/neck and melanoma tumor specimens and cell lines with pharmacological or genetic evidence for involvement of Jak activity in the observed STAT3 activation. In addition, Jak signaling has been implicated in malignant transformation through the activation of other key signaling pathways such as PI3K, Src, Bcl2 and Ras-MAPK. The communication of Jak signaling to these key pathways has the potential to broaden the involvement of this kinase family to a wide spectrum of malignancies.

Tropomysosin Related Kinases (Trk) are a family of receptor tyrosine kinases composed of three family members, TrkA, TrkB and TrkC. The Trks bind with high affinity to, and mediate the signal transduction induced by the Neurotrophin family of ligands whose prototype members are Nerve Growth Factor (NGF), Brain-Derived Neurotrophic Factor (BDNF) and Neurotrophin-3, -4 and -5 (NT-3, NT-4 and NT-5). In addition, a co-receptor lacking enzymatic activity, p75, has been identified which binds all neurotrophines (NTs) with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. In addition to these developmental consequences of Trk signaling, the subversion of this receptor and its signaling pathway in certain malignancies has also been documented. Of particular note are reports of aberrant expression of NGF and TrkA receptor kinase are implicated in the development and progression of human prostatic carcinoma and pancreatic ductal adrenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuroectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. In addition, profound or significantly attenuated reduction of bone pain caused by prostate cancer metastasis has recently been achieved by utilization of anti-NGF antibody. Overall, the oncogenic properties of Trk signaling in multiple tumor types makes the modulation of the Trk receptor signaling a potentially attractive therapeutic intervention point in different malignancies.

The Trk family of RTKs is frequently expressed in lung, breast, pancreatic and prostate cancers as well as in certain type of acute myelogenous leukemia and congenital fibrosarcoma. The tyrosine kinase activity of Trk is believed to promote the unregulated activation of cell proliferation machinery. It is believed that inhibitors of either TrkA, TrkB or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies.

Casein Kinase 2 (CK2) is a serine/threonine kinase that has been implicated in the regulation of stability of a number of oncogenic or tumor suppressor proteins. Proteins such as beta-catenin and c-Myc, that have been established as important components of signaling pathways in cancer cells, have been shown to be phosphorylated by CK2 and these phosphorylation events have been proposed to be required for the stabilization of these proteins. Tumor suppressor proteins, such as PML and PTEN, have also been shown to be phosphorylated by CK2, and these modifications have been suggested to promote degradation of these proteins. Inhibition of CK2 enzymatic activity, such as by small molecules, may lead to the destabilization of oncogene products as well as the stabilization of tumor suppressor proteins, resulting in an anti-proliferative effect on tumor cells.

Another kinase family of interest is the Src family of kinases. These kinases are implicated in cancer, immune system dysfunction and bone remodeling diseases. For general reviews, see Thomas and Brugge, Annu. Rev. Cell Dev. Biol. (1997) 13, 513; Lawrence and Niu, Pharmacol. Ther. (1998) 77, 81; Tatosyan and Mizenina, Biochemistry (Moscow) (2000) 65, 49; Boschelli et al., Drugs of the Future 2000, 25(7), 717, (2000). Members of the Src family include the following eight kinases in mammals: Src, Fyn, Yes, Fgr, Lyn, Hck, Lck, and Blk.

U.S. Patent Publication No. US20080045496 discloses Trk receptor kinases. Example 74 of the publication is shown below. This compound has an IC50 against JAK2 of 0.031 µM and an IC50 against JAK3 of 0.46 µM.

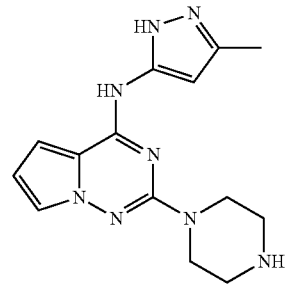 [SMILES: Cc1cc(Nc2nc(N3CCNCC3)nn3cccc23)[nH]n1]

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I

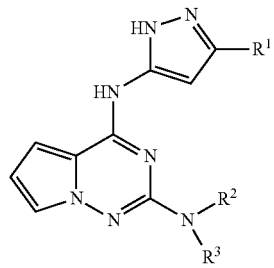

(I)

or stereoisomers, tautomers, pharmaceutically acceptable salts, or solvates thereof, wherein:

$R^1$ is hydrogen, $C_{1-6}$ alkyl substituted with 0-3 $R^a$, $C_{3-6}$ cycloalkyl substituted with 0-3 $R^a$, $C_{6-10}$ aryl substituted with 0-3 $R^a$, or —$CONR^{12}R^{13}$;

$R^2$ and $R^3$ are taken together with the nitrogen atom to which they are attached to form a piperazinyl or diazabicyclo[2.2.1]heptanyl ring; the ring being substituted with at least one of —$COR^{14}$, —$C(O)$—$C(O)$—$R^{14}$, —$SO_2R^{14}$, said ring also being substituted with 0-3 $R^a$;

$R^7$ and $R^8$ are independently hydrogen, $C_{1-6}$ alkyl, $C_{3-6}$ cycloalkyl, or $(CH_2)_r$-phenyl; alternatively $R^7$ and $R^8$, along with nitrogen atom to which they are attached, join to form a 5-10 membered heterocyclic ring;

$R^{12}$ and $R^{13}$ are independently hydrogen, $C_{1-6}$ alkyl optionally substituted with $R^a$, $C_{3-6}$ cycloalkyl optionally substituted with $R^a$, $C_{6-10}$ aryl substituted with 0-3 $R^a$, or a 5-10 membered heterocyclic system containing 1-4 heteroatoms selected from N, O, and S, substituted with 0-3 $R^a$; or alternatively, $R^{12}$ and $R^{13}$ are taken together with the nitrogen atom to which they are attached to form an 4-8 membered ring, the ring optionally containing one or more additional heteroatoms selected from —N—, —S— and —O—; the ring being substituted with 0-1 of hydrogen, —OH, or $C_{1-6}$ alkyl optionally substituted with 0-5 $R^a$;

$R^{14}$ is hydrogen, $C_{1-6}$ alkyl substituted with 0-3 $R^{14a}$, $C_{1-6}$ alkenyl substituted with 0-3 $R^{14a}$, $C_{1-6}$ alkynyl substituted with 0-3 $R^{14a}$, $C_{1-6}$ haloalkyl, $(CHR)_r$—$C_{3-6}$ cycloalkyl substitute with 0-3 $R^{14a}$; bicyclo[4.2.0]octatrienyl substituted with 0-3 $R^{14a}$, indenyl substituted with 0-3 $R^{14a}$, indanonyl substituted with 0-3 $R^{14a}$; —$(CH_2)_r$—$C_{6-10}$ aryl substituted with 0-5 $R^{14a}$, or —$(CH_2)_r$-5-10 membered heterocyclic system containing 1-4 heteroatoms selected from N, O, and S, substituted with 0-3 $R^{14a}$, $R^{14a}$ is F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^b$, —$(CH_2)_rNR^bC(O)OR^c$, —$NR^bC(O)NR^7R^8$, —$S(O)_pNR^7R^8$, —$NR^bS(O)_pR^c$, —$S(O)R^c$, —$S(O)_2R^c$, $C_{1-6}$ alkyl substituted with 0-1 $R^a$, $C_{1-6}$ alkenyl substituted with 0-1 $R^a$, $C_{1-6}$ alkynyl substituted with 0-1 $R^a$, $C_{1-6}$ haloalkyl, a —$(CH_2)_r$-3-14 membered carbocycle optionally substituted with 0-2 $R^a$, or a —$(CH_2)_r$-5-7 membered heterocycle comprising carbon atoms and 1-4 heteroatoms selected from N, O, and $S(O)_p$, wherein said heterocycle is substituted with 0-2 $R^a$;

$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^c$, —$(CH_2)_rNR^bC(O)OR^c$, —$NR^bC(O)NR^7R^8$, —$S(O)_pNR^7R^8$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, OCF3, CF3, CN, NO2, —$OR^e$, —$(CH2)rC(O)Rb$, —$NR^eR^e$, —$NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

R, at each occurrence, is independently from H, $C_{1-6}$ alkyl, $(CH_2)_rC_{3-6}$ cycloalkyl, or $(CH_2)_r$phenyl;

p is 0, 1, or 2;

r is 0, 1, 2, 3, or 4;

or a pharmaceutically acceptable salt or stereoisomer thereof.

In another embodiment of the present invention, there are disclosed compounds of formula I

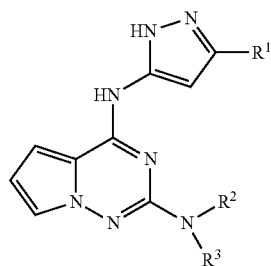

(I)

or stereoisomers, tautomers, pharmaceutically acceptable salts, or solvates thereof, wherein:

$R^1$ is hydrogen, $C_{1-6}$ alkyl substituted with 0-3 $R^a$, $C_{3-6}$ cycloalkyl substituted with 0-3 $R^a$, $C_{6-10}$ aryl substituted with 0-3 $R^a$, or —$CONR^{12}R^{13}$;

$R^2$ and $R^3$ are taken together with the nitrogen atom to which they are attached to form a piperazinyl or diazabicyclo[2.2.1]heptanyl ring; the ring being substituted with at least one of —$COR^{14}$, —$C(O)$—$C(O)$—$R^{14}$, —$SO_2R^{14}$, said ring also being substituted with 0-3 $R^a$;

$R^7$ and $R^8$ are independently hydrogen, $C_{1-6}$ alkyl, $C_{3-6}$ cycloalkyl, or $(CH_2)_r$-phenyl; alternatively $R^7$ and $R^8$, along with nitrogen atom to which they are attached, join to form a 5-10 membered heterocyclic ring;

$R^{12}$ and $R^{13}$ are independently hydrogen, $C_{1-6}$ alkyl optionally substituted with $R^a$, $C_{3-6}$ cycloalkyl optionally substituted with $R^a$, $C_{6-10}$ aryl substituted with 0-3 $R^a$, or a 5-10 membered heterocyclic system containing 1-4 heteroatoms selected from N, O, and S, substituted with 0-3 $R^a$; or alternatively, $R^{12}$ and $R^{13}$ are taken together with the nitrogen atom to which they are attached to form an 4-8 membered ring, the ring optionally containing one or more additional heteroatoms selected from —N—, —S— and —O—; the ring being substituted with 0-1 of hydrogen, —OH, or $C_{1-6}$ alkyl optionally substituted with 0-5 $R^a$;

$R^{14}$ is hydrogen, $C_{1-6}$ alkyl substituted with 0-3 $R^{14a}$, $C_{1-6}$ alkenyl substituted with 0-3 $R^{14a}$, $C_{1-6}$ alkynyl substituted with 0-3 $R^{14a}$, $C_{1-6}$ haloalkyl, $(CHR)_r$—$C_{3-6}$ cycloalkyl substitute with 0-3 $R^{14a}$, —$(CH_2)_r$—$C_{6-10}$ aryl substituted with 0-5 $R^{14a}$, or —$(CH_2)_r$-5-10 membered heterocyclic system containing 1-4 heteroatoms selected from N, O, and S, substituted with 0-3 $R^{14a}$, $R^{14a}$ is F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^b$, —$(CH_2)_rNR^bC(O)OR^c$, —$NR^bC(O)NR^7R^8$, —$S(O)_pNR^7R^8$, —$NR^bS(O)_pR^c$, —$S(O)R^c$, —$S(O)_2R^c$, $C_{1-6}$ alkyl substituted with 0-1 $R^a$, $C_{1-6}$ alkenyl substituted with 0-1 $R^a$, $C_{1-6}$ alkynyl substituted with 0-1 $R^a$, $C_{1-6}$ haloalkyl, a —$(CH_2)_r$-3-14 membered carbocycle optionally substituted with 0-2 $R^a$, or a —$(CH_2)_r$-5-7 membered heterocycle comprising carbon atoms and 1-4 heteroatoms selected from N, O, and $S(O)_p$, wherein said heterocycle is substituted with 0-2 $R^a$;

$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^c$, —$(CH_2)_rNR^bC(O)OR^c$, —$NR^bC(O)NR^7R^8$, —$S(O)_pNR^7R^8$, —$NR^bS(O)_pR^c$, —$S(O)R^b$, —$S(O)_2R^c$, $C_{1-6}$ alkyl, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, OCF3, CF3, CN, NO2, —$OR^e$, —$(CH2)rC(O)Rb$, —$NR^eR^e$, —$NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

R, at each occurrence, is independently from H, $C_{1-6}$ alkyl, $(CH_2)_rC_{3-6}$ cycloalkyl, or $(CH_2)_r$phenyl;

p is 0, 1, or 2;

r is 0, 1, 2, 3, or 4;

or a pharmaceutically acceptable salt or stereoisomer thereof.

In another embodiment are compounds of Formula (I), wherein:

$R^2$ and $R^3$ are taken together with the nitrogen atom to which they are attached to form the ring, the ring is:

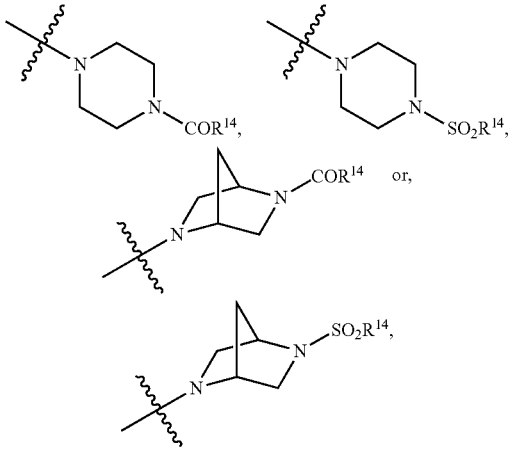

the ring also being substituted with 0-2 $R^a$.

In another embodiment are compounds of Formula (I), wherein:

$R^1$ is hydrogen, $C_{1-4}$ alkyl, $C_{3-6}$ cycloalkyl substituted 0-1 $R^a$, or —$CONR^{12}R^{13}$;

$R^{12}$ and $R^{13}$ are hydrogen, $C_{1-6}$ alkyl, or $C_{3-6}$ cycloalkyl.

In another embodiment are compounds of Formula (I), wherein:

$R^7$ and $R^8$ are independently hydrogen, $C_{1-6}$ alkyl, $C_{3-6}$ cycloalkyl, or $(CH_2)_r$-phenyl.

In another embodiment are compounds of Formula (I), wherein:

$R^{14}$ is hydrogen, $C_{1-6}$ alkyl substituted with 0-3 $R^{14a}$; $C_{1-6}$ alkenyl substituted with 0-3 $R^{14a}$; $(CHR)_r$—$C_{3-6}$ cycloalkyl substitute with 0-3 $R^{14a}$, wherein the cycloalkyl is cyclobutyl, cyclopentyl or cyclohexyl; —$(CH_2)_r$—$C_{6-10}$ aryl substituted with 0-5 $R^{14a}$, wherein the aryl is phenyl, bicyclo[4.2.0]octatrienyl, indenyl, indanonyl; or —$(CH_2)_r$-5-10 membered heterocyclic system containing 1-4 heteroatoms selected from N, O, and S, substituted with 0-3 $R^{14a}$, $R^{14a}$ is F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^b$, —$(CH_2)_rNR^bC(O)OR^c$, —$NR^bC(O)NR^7R^8$, —$S(O)_pNR^7R^8$, —$NR^bS(O)_pR^c$, —$S(O)R^c$, —$S(O)_2R^c$, $C_{1-6}$ alkyl substituted with 0-1 $R^a$, $C_{1-6}$ alkynyl substituted with 0-1 $R^a$, $C_{1-6}$ haloalkyl, a —$(CH_2)_r$-3-14 membered carbocycle optionally substituted with 0-2 $R^a$, wherein the carbocyclic residue is cyclopropyl, cyclopentyl, cyclohexyl, fluorenyl, or phenyl, or a —$(CH_2)_r$-5-7 membered heterocycle comprising carbon atoms and 1-4 heteroatoms selected from N, O, and $S(O)_p$, wherein said heterocycle is substituted with 0-2 $R^a$, wherein the heterocycle is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl.

In another embodiment are compounds of Formula (I), wherein:

$R^{14}$ is hydrogen, $C_{1-6}$ alkyl substituted with 0-3 $R^{14a}$; $C_{1-6}$ alkenyl substituted with 0-3 $R^{14a}$; $(CHR)_r$—$C_{3-6}$ cycloalkyl substitute with 0-3 $R^{14a}$, wherein the cycloalkyl is cyclobutyl, cyclopentyl or cyclohexyl; —$(CH_2)_r$—$C_{6-10}$ aryl substituted with 0-5 $R^{14a}$, wherein the aryl is phenyl, bicyclo[4.2.0]octatrienyl, indenyl, indanonyl; or —$(CH_2)_r$-5-10 membered heterocyclic system containing 1-4 heteroatoms selected from N, O, and S, substituted with 0-3 $R^{14a}$, $R^{14a}$ is F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^b$, —$(CH_2)_rNR^bC(O)OR^c$, —$NR^bC(O)NR^7R^8$, —$S(O)_pNR^7R^8$, —$NR^bS(O)_pR^c$, —$S(O)R^c$, —$S(O)_2R^c$, $C_{1-6}$ alkyl substituted with 0-1 $R^a$, $C_{1-6}$ alkynyl substituted with 0-1 $R^a$, $C_{1-6}$ haloalkyl, a —$(CH_2)_r$-3-14 membered carbocycle optionally substituted with 0-2 $R^a$, wherein the carbocyclic residue is cyclopropyl, cyclopentyl, cyclohexyl, fluorenyl, or phenyl, or a —$(CH_2)_r$-5-7 membered heterocycle comprising carbon atoms and 1-4 heteroatoms selected from N, O, and $S(O)_p$, wherein said heterocycle is substituted with 0-2 $R^a$, wherein the heterocycle is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl.

In another embodiment are compounds of Formula (I), wherein:

r is 0, 1, or 2.

In another embodiment are compounds of Formula (I), wherein:

$R^{14}$ is hydrogen, $C_{1-6}$ alkyl substituted with 0-3 $R^{14a}$; $C_{1-6}$ alkenyl; $(CHR)_r$—$C_{3-6}$ cycloalkyl substitute with 0-3 $R^{14a}$, wherein the cycloalkyl is cyclobutyl, cyclopentyl or cyclohexyl; —$(CH_2)_r$—$C_{6-10}$ aryl substituted with 0-5 $R^{14a}$, wherein the aryl is phenyl, bicyclo[4.2.0]octatrienyl, indenyl, indanonyl; or —$(CH_2)_r$-heterocyclic system containing 1-4 heteroatoms selected from N, O, and S, substituted with 0-3 $R^{14a}$, wherein the heterocyclic system is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl, $R^{14a}$ is F, Cl, Br, $OCF_3$, $CF_3$, $CHF_2$, CN, $NO_2$, —$OR^b$, —$C(O)R^b$, —$C(O)OR^b$, —$OC(O)R^b$, —$(CH_2)_rNR^7R^8$, —$C(O)NR^7R^8$, —$NR^bC(O)R^b$, —$NR^bC(O)OR^c$, —$C(O)NR^7R^8$, —$S(O)_pNR^7R^8$, —$NR^bS(O)_pR^c$, —$S(O)R^c$, —$S(O)_2R^c$, $C_{1-6}$ alkyl substituted with 0-1 $R^a$, —C≡CH, $C_{1-2}$ haloalkyl, a —$(CH_2)_r$-3-7 membered carbocycle optionally substituted with 0-2 $R^a$, wherein the carbocyclic residue is cyclopropyl, cyclopentyl, cyclohexyl, fluorenyl, or phenyl, or a —$(CH_2)_r$-5-7 membered heterocycle comprising carbon atoms and 1-4 heteroatoms selected from N, O, and $S(O)_p$, wherein said heterocycle is substituted with 0-2 $R^a$, wherein the heterocycle is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl;

In another embodiment are compounds of Formula (I), wherein:

$R^{14}$ is hydrogen, $C_{1-6}$ alkyl substituted with 0-3 $R^{14a}$; $C_{1-6}$ alkenyl; $(CHR)_r$—$C_{3-6}$ cycloalkyl substitute with 0-3 $R^{14a}$, wherein the cycloalkyl is cyclobutyl, cyclopentyl or cyclohexyl; —$(CH_2)_r$—$C_{6-10}$ aryl substituted with 0-5 $R^{14a}$, wherein the aryl is phenyl, bicyclo[4.2.0]octatrienyl, indenyl, indanonyl; or —$(CH_2)_r$-heterocyclic system containing 1-4 heteroatoms selected from N, O, and S, substituted with 0-3 $R^{14a}$, wherein the heterocyclic system is pyridyl, pyridinyl, piperidinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl;

$R^{14a}$ is F, Cl, Br, $OCF_3$, $CF_3$, $CHF_2$, CN, $NO_2$, $-(CH_2)_rOR^b$, $-C(O)R^b$, $-C(O)OR^b$, $-OC(O)R^b$, $-(CH_2)_rNR^7R^8$, $-C(O)NR^7R^8$, $-NR^bC(O)R^b$, $-NR^bC(O)OR^c$, $-C(O)NR^7R^8$, $-S(O)_pNR^7R^8$, $-NR^bS(O)_pR^c$, $-S(O)R^c$, $-S(O)_2R^c$, $C_{1-6}$ alkyl substituted with 0-1 $R^a$, $-C\equiv CH$, $C_{1-2}$ haloalkyl, a $-(CH_2)_r$-3-7 membered carbocycle optionally substituted with 0-2 $R^a$, wherein the carbocyclic residue is cyclopropyl, cyclopentyl, cyclohexyl, fluorenyl, or phenyl, or a $-(CH_2)_r$-5-7 membered heterocycle comprising carbon atoms and 1-4 heteroatoms selected from N, O, and $S(O)_p$, wherein said heterocycle is substituted with 0-2 $R^a$, wherein the heterocycle is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl;

In another embodiment there is a pharmaceutical composition comprising one or more compounds of Formula (I) and a pharmaceutically acceptable carrier.

In another embodiment there is a method for treating leukemia, myeloproliferative disorders and/or hematological disorders, comprising administering to a mammalian species in need thereof, a therapeutically effective amount of one or more compound of Formula (I).

In another embodiment are compounds of Formula (I), wherein:

$R^2$ and $R^3$ are taken together with the nitrogen atom to which they are attached to form the ring, the ring is:

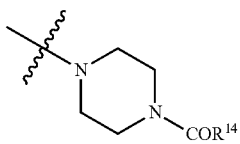

the ring also being substituted with 0-2 $R^a$.

In another embodiment are compounds of Formula (I), wherein:

$R^1$ is hydrogen, $C_{1-4}$ alkyl, $C_{3-6}$ cycloalkyl substituted 0-1 $R^a$;

$R^{12}$ and $R^{13}$ are hydrogen, $C_{1-6}$ alkyl, or $C_{3-6}$ cycloalkyl.

In another embodiment, $R^1$ is $C_{1-4}$ alkyl, $C_{3-6}$ cycloalkyl substituted 0-1 $R^a$, or $-CONR^{12}R^{13}$.

In another embodiment, $R^1$ is methyl, cyclopropyl substituted with 0-1 methyl or trifluoromethyl, or $-CONR^{12}R^{13}$.

In another embodiment, $R^{12}$ and $R^{13}$ are hydrogen, methyl, ethyl, or cyclopropyl.

In another embodiment, $R^{14}$ is $C_{1-6}$ alkyl substituted with 0-3 $R^{14a}$, $C_{1-6}$ alkenyl; $(CHR)_r$—$C_{3-6}$ cycloalkyl substitute with 0-3 $R^{14a}$, wherein the cycloalkyl is cyclobutyl, cyclopentyl or cyclohexyl; $-(CH_2)_r$—$C_{6-10}$ aryl substituted with 0-5 $R^{14a}$, wherein the aryl is phenyl, bicyclo[4.2.0]octatrienyl, indenyl, indanonyl; or $-(CH_2)_r$-heterocyclic system containing 1-4 heteroatoms selected from N, O, and S, substituted with 0-3 $R^{14a}$, wherein the heterocyclic system is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl.

In another embodiment, $R^{14a}$ is F, Cl, Br, $OCF_3$, $CF_3$, $CHF_2$, CN, $NO_2$, $-OR^b$, $-C(O)R^b$, $-C(O)OR^b$, $-OC(O)R^b$, $-(CH_2)_rNR^7R^8$, $-C(O)NR^7R^8$, $-NR^bC(O)R^b$, $-NR^bC(O)OR^c$, $-C(O)NR^7R^8$, $-S(O)_pNR^7R^8$, $-NR^bS(O)_pR^c$, $-S(O)R^c$, $-S(O)_2R^c$, $C_{1-6}$ alkyl substituted with 0-1 $R^a$, $-C\equiv CH$, $C_{1-2}$ haloalkyl, a $-(CH_2)_r$-3-'4 membered carbocycle optionally substituted with 0-2 $R^a$, wherein the carbocyclic residue is cyclopropyl, cyclopentyl, cyclohexyl, fluorenyl, or phenyl; or pyrazolyl substituted with 0-2 $R^a$.

In another embodiment, $R^{14a}$ is F, Cl, Br, $OCF_3$, $CF_3$, $CHF_2$, CN, $NO_2$, $-OR^b$, $-NR^bC(O)R^b$, $-NR^bC(O)OR^c$, $-S(O)R^c$, $-S(O)_2R^c$, $C_{1-6}$ alkyl substituted with 0-1 $R^a$, $-C\equiv CH$, $C_{1-2}$ haloalkyl, a $-(CH_2)_r$-3-7 membered carbocycle optionally substituted with 0-2 $R^a$, wherein the carbocyclic residue is cyclopropyl, cyclopentyl, cyclohexyl, fluorenyl or phenyl; or pyrazolyl substituted with 0-2 $R^a$.

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof.

In another embodiment, the present invention provides a method for treating proliferative disorders and/or cancer comprising: administering to a patient in need of such treatment a therapeutically effective amount of at least one of the compounds of the present invention or a stereoisomer, tautomer, pharmaceutically acceptable salt, solvate or prodrug thereof, in combination with at least one other anti-cancer agent, or a stereoisomer, tautomer, pharmaceutically acceptable salt, solvate or prodrug thereof.

In another embodiment, the present invention provides a method for treating proliferative disorders and/or cancer comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a method of treating a patient in need of proliferative disorder and/or cancer treatment, comprising: administering a compound of the present invention or a stereoisomer, tautomer, pharmaceutically acceptable salt, solvate, or prodrug form thereof in an amount effective to treat the proliferative disorder and/or cancer.

In another embodiment, the present invention provides a method of treating myeloproliferative diseases (polycythemia vera, essential thrombocytopenia, myelofibrosis), solid tumors of the pancreatic, prostate, lung, head and neck, breast, colon, ovary, gastric cancer as well as other tumor types including multiple myeloma, melanoma, neuroblastoma, globalstoma and hematological malignancies such as acute myelogenous leukemia.

In another embodiment, the present invention provides a novel method, comprising: administering a compound of the present invention or a stereoisomer, tautomer, pharmaceutically acceptable salt, solvate, or prodrug form thereof in an amount effective to treat a proliferative disorder and/or cancer.

In another embodiment, the present invention provides a compound of the present invention for use in therapy.

In another embodiment, the present invention provides a compound of the present invention for use in therapy for treating a proliferative disorder and/or cancer.

In another embodiment, the present invention also provides the use of a compound of formula I of the present invention for the manufacture of a medicament for the treatment of a proliferative disorder and/or cancer.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The following are definitions of terms that may be used in the present specification. The initial definition provided for a group or term herein applies to that group or term throughout the present specification individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C═N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., ═O), then 2 hydrogens on the atom are replaced. Keto substituents are not present on aromatic moieties. Ring double bonds, as used herein, are double bonds that are formed between two adjacent ring atoms (e.g., C═C, C═N, or N═N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, arylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

As used herein, the term "heterocycle", "heterocyclyl", "heterocyclic system" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

In another embodiment, heterocycles include, but are not limited to, pyridyl, pyridinyl, isoxazyl, isoquinolinyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl Also included are smaller heterocyclyls, such as, epoxides and aziridines.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may exist as a free form or may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include 13C and 14C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of comp The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

UTILITY

The present invention is based on the discovery that certain pyrrolotriazines are inhibitors of protein kinases. More specifically, pyrrolotriazines such as those described in this invention inhibit the protein tyrosine kinase activity of members of the Jak family of receptors, TRK and as well as Src. Pyrrolotriazines such as those described in this invention also inhibit the protein serine/threonine kinase activity of members of the CK2 family of receptors. These inhibitors will be useful in the treatment of proliferative diseases that are dependent on signaling by one or more of these receptors. Such diseases include myeloproliferative diseases, solid tumors of the pancreatic, prostate, lung, head and neck, breast, colon, ovary, as well as other tumor types including multiple myeloma, melanoma, neuroblastoma, gliobalstoma and hematological malignancies such as acute myelogenous leukemia.

The invention also relates to a pharmaceutical composition of compound of formula I, or pharmaceutically acceptable salt thereof, and a pharmaceutically acceptable carrier in the treatment of hyperproliferative disorder in mammal. In particular, said pharmaceutical composition is expected to inhibit the growth and/or metastasis of those primary and recurrent solid tumors which are associated with TrkA, TrkB, TrkC, Flt-3 (Fms-like kinase-3), Jak2, Jak3, Src and CK2, especially those tumors which are significantly dependent on JAK2, TrkA, TrkB, TrkC, CK2 for their growth and spread, including for example, cancers of the blood, thyroid, breast, colon, pancreas, or a variety of tumor types including multiple myeloma, melanoma, neuroblastoma and glioblastoma.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit TrkA, TrkB, TrkC, Flt-3, Jak2, Jak3, Src, CK2 and Tie-2 kinases, compounds of the present invention can be used for the treatment of proliferative diseases, including cancer. The TrkA, TkB and TrkC receptor kinases have been shown to be expressed and activated in tumors including thyroid, breast, colon, acute myelogenous leukemia and elevated Trk receptors and corresponding ligands have also been reported in a variety of tumor types including multiple myeloma, melanoma, pancreatic acnrcinoma, neuroblastoma and glioblastoma. It is therefore expected that inhibitors of the TrkA, TrkB and TrkC kinases will have efficacy in the treatment of tumors that depend on signaling from either or both of the two receptors. These compounds are expected to have efficacy either as single agent or in combination (simultaneous or sequentially) with other chemotherapeutic agents such as Taxol®, adriamycin, and cisplatin.

Thus, the present invention provides methods for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burkett's lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

The present invention provides methods for the treatment of leukemia, myeloproliferative diseases (polycythemia vera, essential thrombocytopenia, myelofibrosis), multiple myeloma, colon cancer, breast cancer, and gastric cancer.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; kinase inhibitors, e.g. Gleevec® and dasatinib (Sprycel®); Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to treat the cancer.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Biological Assays
JAK2 Tyrosine Kinase Assay

The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM MgCl$_2$, 25 mM Beta-Glycerolphosphate, 0.015% Brij35 and 4 mM DTT). The reaction was initiated by the combination of JAK2 with substrates and test compounds. The reaction was incubated at room temperature for 60 min. and terminated by adding 45 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; JAK2 fluorescent peptide, 1.5 µM; JAK2, 1 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis JAK3 Tyrosine Kinase Assay The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM MgCl$_2$, 25 mM Beta-Glycerolphosphate, 0.015% Brij35 and 4 mM DTT). The reaction was initiated by the combination of JAK3 with substrates and test compounds. The reaction was incubated at room temperature for 60 min. and terminated by adding 45 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 8 µM; JAK3 fluorescent peptide, 1.5 µM; JAK3, 2.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

Compounds described herein were tested in the JAK2 assay described above. The following results were obtained.

| Example No. | Jak2(IC$_{50}$, µM) | Jak3(IC$_{50}$, µM) |
| --- | --- | --- |
| 7 | 0.32 | 2.06 |
| 10 | 6.04E−04 | 9.84E−03 |
| 20 | 8.14E−03 | 0.05 |
| 24 | 1.14E−03 | 5.98E−03 |
| 32 | 7.16E−03 | 0.12 |
| 37 | 7.73E−03 | 0.16 |
| 38 | 1.12E−03 | 0.03 |
| 43 | 2.66 | 50.00 |
| 45 | 8.91E−04 | 0.01 |
| 48 | 9.03E−04 | 0.02 |
| 49 | 7.90E−03 | 0.17 |
| 66 | 8.98E−04 | 0.01 |
| 90 | 8.15E−03 | 0.07 |
| 91 | 6.97E−04 | 0.02 |
| 95 | 6.65E−03 | 0.09 |
| 106 | 7.14E−03 | 0.04 |
| 110 | 1.00E−03 | 0.02 |
| 126 | 0.15 | 1.41 |

-continued

| Example No. | Jak2(IC$_{50}$, μM) | Jak3(IC$_{50}$, μM) |
|---|---|---|
| 132 | 9.71E-04 | 0.03 |
| 134 | 8.87E-04 | 8.41E-03 |
| 139 | 1.04E-03 | 0.07 |
| 150 | 0.70 | 13.65 |
| 152 | 0.30 | 2.36 |
| 158 | 0.30 | 1.74 |
| 164 | 0.24 | 1.49 |
| 168 | 7.07E-03 | 0.21 |
| 187 | 6.83E-03 | 0.20 |
| 193 | 0.13 | 3.05 |
| 200 | 7.25E-03 | 0.12 |
| 211 | 0.59 | 9.48 |
| 222 | 0.17 | 0.76 |
| 230 | 0.19 | 0.42 |

A. CK2 Kinase Assay

CK2 enzymatic assays were performed in 384-well plates, and reaction mixtures contained 10 μM of peptide substrate (RRRADDSDDDDD-NH$_2$), [γ-$^{33}$P]ATP (10 μCi) at 25 μM (CK2A1) or 5 μM (CK2A2), 20 mM Hepes (pH 7.4), 100 mM NaCl, 10 mM MgCl$_2$, 0.25 mM dithiothreitol, Brij-35 at 0.015%, and recombinant CK2A1 (10 nM, Invitrogen) or CK2A2 (5 nM, Upstate Biotechnology). Reaction mixtures were incubated at 30° C. for 1 h, and reaction products were captured by binding to phosphocellulose (P81) filter plates. Incorporation of radioactive phosphate into the peptide substrate was determined by liquid scintillation counting. The potency of compounds in inhibiting CK2 is expressed as IC$_{50}$, defined as the concentrations of compounds required to inhibit the enzymatic activity by 50%. Other compounds described herein and compounds falling within the formulae of I (including formula aI(a)), are surprisingly advantageous for their CK2 enzyme inhibition activity and/or other drugability properties, e.g., having desirable stability, bioavailability, therapeutic index and/or toxicity values that are important to their use as pharmaceutical agents.

B. Cell Proliferation Inhibition Assay

Compounds were evaluated for their ability to inhibit cell proliferation, using an assay that measures mitochondrial metabolic activity, that is directly correlated with cell numbers. Cells were plated at 2000 cells/well in 96-well plates and were cultured for 24 h in RPMI-1640 supplemented with 2% fetal bovine serum, before test compounds were added. Compounds were diluted in culture medium such that the final concentration of dimethyl sulfoxide never exceeded 1%. Following the addition of compounds, the cells were cultured for an additional 72 h before cell viability was determined by measuring the conversion of 3-(4,5-dimethylthiazol-2-yl)-2, 5-diphenyltetrazolium bromide (MTT) dye using the CellTiter96 kit (Promega).

Compounds described herein have been tested in one or more of the above identified assays and have been found to be active.

Another embodiment of the invention are compounds having an IC$_{50}$ in the JAK2 assay of 5 nM or less and are selected from the following:

N-(5-methyl-1H-pyrazol-3-yl)-2-(4-(phenylacetyl)-1-piperazinyl)pyrrolo[2,1-f][1,2,4]triazin-4-amine;

2-(4-(2-fluorobenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-pentanoyl-1-piperazinyl)pyrrolo[2,1-f][1,2,4]triazin-4-amine;

N-(5-methyl-1H-pyrazol-3-yl)-2-(4-((2-(trifluoromethyl)phenyl)acetyl)-1-piperazinyl)pyrrolo[2,1-f][1,2,4]triazin-4-amine;

N-(5-methyl-1H-pyrazol-3-yl)-2-(4-((1-phenylcyclopropyl)carbonyl)-1-piperazinyl)pyrrolo[2,1-f][1,2,4]triazin-4-amine;

2-(4-(cyclohexylacetyl)-1-piperazinyl)-N-(5-methyl-1H-pyrazol-3-yl)pyrrolo[2,1-f][1,2,4]triazin-4-amine;

2-(4-((1-methylcyclopropyl)carbonyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-((6-methyl-3-pyridinyl)carbonyl)-1-piperazinyl)pyrrolo[2,1-f][1,2,4]triazin-4-amine;

2-(4-(3-furoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-((1-methyl-1H-pyrrol-2-yl)carbonyl)-1-piperazinyl)pyrrolo[2,1-f][1,2,4]triazin-4-amine;

2-(4-(4-methoxybenzoyl)-1-piperazinyl)-N-(5-methyl-1H-pyrazol-3-yl)pyrrolo[2,1-f][1,2,4]triazin-4-amine;

2-(4-(4-fluorobenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(1H-pyrazol-3-ylcarbonyl)-1-piperazinyl)pyrrolo[2,1-f][1,2,4]triazin-4-amine;

N-(5-methyl-1H-pyrazol-3-yl)-2-(4-((4-methyl-2-thienyl)carbonyl)-1-piperazinyl)pyrrolo[2,1-f][1,2,4]triazin-4-amine;

2-(4-(2,5-dimethyl-3-furoyl)-1-piperazinyl)-N-(5-methyl-1H-pyrazol-3-yl)pyrrolo[2,1-f][1,2,4]triazin-4-amine;

2-((4-(4-((5-methyl-1H-pyrazol-3-yl)amino)pyrrolo[2,1-f][1,2,4]triazin-2-yl)-1-piperazinyl)carbonyl)benzonitrile;

2-(4-((2,6-dichlorophenyl)acetyl)-1-piperazinyl)-N-(5-methyl-1H-pyrazol-3-yl)pyrrolo[2,1-f][1,2,4]triazin-4-amine;

2-(4-(bicyclo[4.2.0]octa-1,3,5-trien-7-ylcarbonyl)-1-piperazinyl)-N-(5-methyl-1H-pyrazol-3-yl)pyrrolo[2,1-f][1,2,4]triazin-4-amine;

2-(4-((4-methoxyphenyl)acetyl)-1-piperazinyl)-N-(5-methyl-1H-pyrazol-3-yl)pyrrolo[2,1-f][1,2,4]triazin-4-amine;

2-(4-((3-methylphenyl)acetyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-((3-(trifluoromethyl)phenyl)acetyl)-1-piperazinyl)pyrrolo[2,1-f][1,2,4]triazin-4-amine;

2-(4-((3-chlorophenyl)acetyl)-1-piperazinyl)-N-(5-methyl-1H-pyrazol-3-yl)pyrrolo[2,1-f][1,2,4]triazin-4-amine;

2-(4-((3-fluorophenyl)acetyl)-1-piperazinyl)-N-(5-methyl-1H-pyrazol-3-yl)pyrrolo[2,1-f][1,2,4]triazin-4-amine;

2-(4-((2-chlorophenyl)acetyl)-1-piperazinyl)-N-(5-methyl-1H-pyrazol-3-yl)pyrrolo[2,1-f][1,2,4]triazin-4-amine;

2-(4-(2-fluoro-6-(trifluoromethyl)benzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(4-(trifluoromethyl)benzoyl)-1-piperazinyl)pyrrolo[2,1-f][1,2,4]triazin-4-amine;

2-(4-(3-methylbenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(3-(trifluoromethyl)benzoyl)-1-piperazinyl)pyrrolo[2,1-f][1,2,4]triazin-4-amine;

2-(4-(3-chlorobenzoyl)-1-piperazinyl)-N-(5-methyl-1H-pyrazol-3-yl)pyrrolo[2,1-f][1,2,4]triazin-4-amine;

2-(4-(3-methoxybenzoyl)-1-piperazinyl)-N-(5-methyl-1H-pyrazol-3-yl)pyrrolo[2,1-f][1,2,4]triazin-4-amine;

3-((4-(4-((5-methyl-1H-pyrazol-3-yl)amino)pyrrolo[2,1-f][1,2,4]triazin-2-yl)-1-piperazinyl)carbonyl)benzonitrile;

2-(4-(3-fluorobenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(2-(trifluoromethyl)benzoyl)-1-piperazinyl)pyrrolo[2,1-f][1,2,4]triazin-4-amine;

N-(3-((4-(4-((5-methyl-1H-pyrazol-3-yl)amino)pyrrolo[2,1-f][1,2,4]triazin-2-yl)-1-piperazinyl)carbonyl)phenyl)acetamide;

N-(4-((4-(4-((5-methyl-1H-pyrazol-3-yl)amino)pyrrolo[2,1-f][1,2,4]triazin-2-yl)-1-piperazinyl)carbonyl)phenyl)acetamide;

2-(4-(2-chloro-6-fluorobenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(1,2,3-thiadiazol-4-ylcarbonyl)-1-piperazinyl)pyrrolo[2,1-f][1,2,4]triazin-4-amine;

N-(5-methyl-1H-pyrazol-3-yl)-2-(4-((2-methyl-3-pyridinyl)carbonyl)-1-piperazinyl)pyrrolo[2,1-f][1,2,4]triazin-4-amine;

N-(5-methyl-1H-pyrazol-3-yl)-2-(4-((1-phenylcyclopentyl)carbonyl)-1-piperazinyl)pyrrolo[2,1-f][1,2,4]triazin-4-amine;

N-(5-methyl-1H-pyrazol-3-yl)-2-(4-(1,3-oxazol-2-ylcarbonyl)-1-piperazinyl)pyrrolo[2,1-f][1,2,4]triazin-4-amine;

N-(5-methyl-1H-pyrazol-3-yl)-2-(4-((1-phenylcyclobutyl)carbonyl)-1-piperazinyl)pyrrolo[2,1-f][1,2,4]triazin-4-amine;

3-(2-(4-(4-((5-methyl-1H-pyrazol-3-yl)amino)pyrrolo[2,1-f][1,2,4]triazin-2-yl)-1-piperazinyl)-2-oxoethyl)benzonitrile;

N-(5-methyl-1H-pyrazol-3-yl)-2-(4-((4-(trifluoromethoxy)phenyl)acetyl)-1-piperazinyl)pyrrolo[2,1-f][1,2,4]triazin-4-amine;

2-(4-(2-fluoro-6-methoxybenzoyl)-1-piperazinyl)-N-(5-methyl-1H-pyrazol-3-yl)pyrrolo[2,1-f][1,2,4]triazin-4-amine;

2-(4-((2-bromophenyl)acetyl)-1-piperazinyl)-N-(5-methyl-1H-pyrazol-3-yl)pyrrolo[2,1-f][1,2,4]triazin-4-amine;

2-(4-((2,6-difluorophenyl)acetyl)-1-piperazinyl)-N-(5-methyl-1H-pyrazol-3-yl)pyrrolo[2,1-f][1,2,4]triazin-4-amine;

2-(4-(2-chloro-6-methylbenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(2-(trifluoromethoxy)benzoyl)-1-piperazinyl)pyrrolo[2,1-f][1,2,4]triazin-4-amine;

N-(5-methyl-1H-pyrazol-3-yl)-2-(4-(4-(trifluoromethoxy)benzoyl)-1-piperazinyl)pyrrolo[2,1-f][1,2,4]triazin-4-amine;

N-(5-methyl-1H-pyrazol-3-yl)-2-(4-((3-(trifluoromethoxy)phenyl)acetyl)-1-piperazinyl)pyrrolo[2,1-f][1,2,4]triazin-4-amine;

2-(4-((4-chloro-2-fluorophenyl)acetyl)-1-piperazinyl)-N-(5-methyl-1H-pyrazol-3-yl)pyrrolo[2,1-f][1,2,4]triazin-4-amine;

2-(4-((2R)-2-methoxy-2-phenylacetyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(1,3-oxazol-5-ylcarbonyl)-1-piperazinyl)pyrrolo[2,1-f][1,2,4]triazin-4-amine;

2-(4-((benzyloxy)acetyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-((2S)-3,3,3-trifluoro-2-methoxy-2-phenylpropanoyl)-1-piperazinyl)pyrrolo[2,1-f][1,2,4]triazin-4-amine;

2-(2-(4-(4-((5-methyl-1H-pyrazol-3-yl)amino)pyrrolo[2,1-f][1,2,4]triazin-2-yl)-1-piperazinyl)-2-oxoethyl)benzonitrile;

N-(2-((4-(4-((5-methyl-1H-pyrazol-3-yl)amino)pyrrolo[2,1-f][1,2,4]triazin-2-yl)-1-piperazinyl)carbonyl)phenyl)acetamide;

N-(5-methyl-1H-pyrazol-3-yl)-2-(4-(1,2,5-oxadiazol-3-ylcarbonyl)-1-piperazinyl)pyrrolo[2,1-f][1,2,4]triazin-4-amine;

1-(2,6-difluorophenyl)-2-(4-(4-((5-methyl-1H-pyrazol-3-yl)amino)pyrrolo[2,1-f][1,2,4]triazin-2-yl)-1-piperazinyl)-2-oxoethanol;

1-(4-fluorophenyl)-2-(4-(4-((5-methyl-1H-pyrazol-3-yl)amino)pyrrolo[2,1-f][1,2,4]triazin-2-yl)-1-piperazinyl)-2-oxoethanol;

1-(4-chlorophenyl)-2-(4-(4-((5-methyl-1H-pyrazol-3-yl)amino)pyrrolo[2,1-f][1,2,4]triazin-2-yl)-1-piperazinyl)-2-oxoethanol;

tert-butyl((1S)-1-(4-fluorophenyl)-2-(4-(4-((5-methyl-1H-pyrazol-3-yl)amino)pyrrolo[2,1-f][1,2,4]triazin-2-yl)-1-piperazinyl)-2-oxoethyl)carbamate;

2-(4-(2-(4-chlorophenyl)-3-methylbutanoyl)-1-piperazinyl)-N-(5-methyl-1H-pyrazol-3-yl)pyrrolo[2,1-f][1,2,4]triazin-4-amine;

2-(4-((2,6-difluoro-4-methoxyphenyl)acetyl)-1-piperazinyl)-N-(5-methyl-1H-pyrazol-3-yl)pyrrolo[2,1-f][1,2,4]triazin-4-amine;

2-(4-((4-ethoxy-2,6-difluorophenyl)acetyl)-1-piperazinyl)-N-(5-methyl-1H-pyrazol-3-yl)pyrrolo[2,1-f][1,2,4]triazin-4-amine;

2-(4-(2,2-dimethylbutanoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-((1-(trifluoromethyl)cyclobutyl)carbonyl)-1-piperazinyl)pyrrolo[2,1-f][1,2,4]triazin-4-amine;

1-((4-(4-((5-methyl-1H-pyrazol-3-yl)amino)pyrrolo[2,1-f][1,2,4]triazin-2-yl)-1-piperazinyl)carbonyl)cyclopropanecarbonitrile;

2-(4-(2-(4-chlorophenyl)propanoyl)-1-piperazinyl)-N-(5-methyl-1H-pyrazol-3-yl)pyrrolo[2,1-f][1,2,4]triazin-4-amine;

2-(4-(2-(4-chlorophenyl)-2-methylpropanoyl)-1-piperazinyl)-N-(5-methyl-1H-pyrazol-3-yl)pyrrolo[2,1-f][1,2,4]triazin-4-amine;

N-(2-(4-(4-((5-methyl-1H-pyrazol-3-yl)amino)pyrrolo[2,1-f][1,2,4]triazin-2-yl)-1-piperazinyl)-2-oxo-1-phenylethyl)acetamide;

N-(5-methyl-1H-pyrazol-3-yl)-2-(4-((2S)-2-phenylbutanoyl)-1-piperazinyl)pyrrolo[2,1-f][1,2,4]triazin-4-amine;

2-(4-((1-(4-methylphenyl)cyclohexyl)carbonyl)-1-piperazinyl)-N-(5-methyl-1H-pyrazol-3-yl)pyrrolo[2,1-f][1,2,4]triazin-4-amine;

tert-butyl (1-(4-chlorophenyl)-2-(4-(4-((5-methyl-1H-pyrazol-3-yl)amino)pyrrolo[2,1-f][1,2,4]triazin-2-yl)-1-piperazinyl)-2-oxoethyl)carbamate;

2-(4-(2-chloro-4,5-difluorobenzoyl)-1-piperazinyl)-N-(5-methyl-1H-pyrazol-3-yl)pyrrolo[2,1-f][1,2,4]triazin-4-amine;

tert-butyl (2-((4-(4-((5-methyl-1H-pyrazol-3-yl)amino)pyrrolo[2,1-f][1,2,4]triazin-2-yl)-1-piperazinyl)carbonyl)phenyl)carbamate;

2-(4-(2-(3,5-dimethyl-1H-pyrazol-4-yl)benzoyl)-1-piperazinyl)-N-(5-methyl-1H-pyrazol-3-yl)pyrrolo[2,1-f][1,2,4]triazin-4-amine;

2-(4-(2-bromobenzoyl)-1-piperazinyl)-N-(5-methyl-1H-pyrazol-3-yl)pyrrolo[2,1-f][1,2,4]triazin-4-amine;

2-(4-(2,4-dichlorobenzoyl)-1-piperazinyl)-N-(5-methyl-1H-pyrazol-3-yl)pyrrolo[2,1-f][1,2,4]triazin-4-amine;
2-(4-(2,5-dichlorobenzoyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(2-phenoxybenzoyl)-1-piperazinyl)pyrrolo[2,1-f][1,2,4]triazin-4-amine;
2-(4-((2-chloro-3-pyridinyl)carbonyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(2-nitrobenzoyl)-1-piperazinyl)pyrrolo[2,1-f][1,2,4]triazin-4-amine;
2-(4-((3-chloro-1-benzothiophene-2-yl)carbonyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(2-(phenoxymethyl)benzoyl)-1-piperazinyl)pyrrolo[2,1-f][1,2,4]triazin-4-amine;
2-(4-((1-(2-chloro-6-fluorophenyl)cyclohexyl)carbonyl)-1-piperazinyl)-N-(5-methyl-1H-pyrazol-3-yl)pyrrolo[2,1-f][1,2,4]triazin-4-amine;
(2R)-1-(4-(4-((5-methyl-1H-pyrazol-3-yl)amino)pyrrolo[2,1-f][1,2,4]triazin-2-yl)-1-piperazinyl)-1-oxo-4-phenyl-2-butanol;
(2R)-2-(4-fluorophenyl)-1-(4-(4-((5-methyl-1H-pyrazol-3-yl)amino)pyrrolo[2,1-f][1,2,4]triazin-2-yl)-1-piperazinyl)-1-oxo-2-propanol;
(2S)-1-(4-(4-((5-methyl-1H-pyrazol-3-yl)amino)pyrrolo[2,1-f][1,2,4]triazin-2-yl)-1-piperazinyl)-1-oxo-3-phenyl-2-propanol;
(1S)-2-(4-(4-((5-methyl-1H-pyrazol-3-yl)amino)pyrrolo[2,1-f][1,2,4]triazin-2-yl)-1-piperazinyl)-2-oxo-1-phenylethanol;
(1R)-2-(4-(4-((5-methyl-1H-pyrazol-3-yl)amino)pyrrolo[2,1-f][1,2,4]triazin-2-yl)-1-piperazinyl)-2-oxo-1-phenylethanol;
3-((4-(4-((5-methyl-1H-pyrazol-3-yl)amino)pyrrolo[2,1-f][1,2,4]triazin-2-yl)-1-piperazinyl)carbonyl)-1-indanone;
1-(2-fluorophenyl)-2-(4-(4-((5-methyl-1H-pyrazol-3-yl)amino)pyrrolo[2,1-f][1,2,4]triazin-2-yl)-1-piperazinyl)-2-oxoethanol;
N-(5-methyl-1H-pyrazol-3-yl)-2-(4-(2-phenylbutanoyl)-1-piperazinyl)pyrrolo[2,1-f][1,2,4]triazin-4-amine;
tert-butyl (1-((4-(4-((5-methyl-1H-pyrazol-3-yl)amino)pyrrolo[2,1-f][1,2,4]triazin-2-yl)-1-piperazinyl)carbonyl)-2,3-dihydro-1H-inden-1-yl)carbamate;
or salt thereof.

In addition to activity against JAK2, selectivity for JAK2 over JAK 3 would be beneficial to mitigate risks for overt immunosuppression.

Another embodiment of the invention are compounds having selectivity of 15 or better for JAK2 activity versus JAK3 activity and are selected from:
2-(4-(2-chlorobenzoyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(phenylacetyl)-1-piperazinyl)pyrrolo[2,1-f][1,2,4]triazin-4-amine;
2-(4-(2-fluorobenzoyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-pentanoyl-1-piperazinyl)pyrrolo[2,1-f][1,2,4]triazin-4-amine;
N-(5-methyl-1H-pyrazol-3-yl)-2-(4-((2-(trifluoromethyl)phenyl)acetyl)-1-piperazinyl)pyrrolo[2,1-f][1,2,4]triazin-4-amine;
N-(5-methyl-1H-pyrazol-3-yl)-2-(4-((1-phenylcyclopropyl)carbonyl)-1-piperazinyl)pyrrolo[2,1-f][1,2,4]triazin-4-amine;
2-(4-(cyclohexylacetyl)-1-piperazinyl)-N-(5-methyl-1H-pyrazol-3-yl)pyrrolo[2,1-f][1,2,4]triazin-4-amine;
2-(4-((1-methylcyclopropyl)carbonyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-((1-methyl-1H-pyrrol-2-yl)carbonyl)-1-piperazinyl)pyrrolo[2,1-f][1,2,4]triazin-4-amine;
N-(5-methyl-1H-pyrazol-3-yl)-2-(4-((4-methyl-2-thienyl)carbonyl)-1-piperazinyl)pyrrolo[2,1-f][1,2,4]triazin-4-amine;
2-(4-(5-methyl-2-pyrazinyl)carbonyl)-1-piperazinyl)-N-(5-methyl-1H-pyrazol-3-yl)pyrrolo[2,1-f][1,2,4]triazin-4-amine;
2-(4-(4-chloro-2-fluorobenzoyl)-1-piperazinyl)-N-(5-methyl-1H-pyrazol-3-yl)pyrrolo[2,1-f][1,2,4]triazin-4-amine;
2-(4-((2,4-difluorophenyl)acetyl)-1-piperazinyl)-N-(5-methyl-1H-pyrazol-3-yl)pyrrolo[2,1-f][1,2,4]triazin-4-amine;
2-(4-((2,6-dichlorophenyl)acetyl)-1-piperazinyl)-N-(5-methyl-1H-pyrazol-3-yl)pyrrolo[2,1-f][1,2,4]triazin-4-amine;
2-(4-isobutyryl-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-((4-(trifluoromethyl)phenyl)acetyl)-1-piperazinyl)pyrrolo[2,1-f][1,2,4]triazin-4-amine;
2-(4-(bicyclo[4.2.0]octa-1,3,5-trien-7-ylcarbonyl)-1-piperazinyl)-N-(5-methyl-1H-pyrazol-3-yl)pyrrolo[2,1-f][1,2,4]triazin-4-amine;
2-(4-((4-methoxyphenyl)acetyl)-1-piperazinyl)-N-(5-methyl-1H-pyrazol-3-yl)pyrrolo[2,1-f][1,2,4]triazin-4-amine;
2-(4-((3-methylphenyl)acetyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-((3-(trifluoromethyl)phenyl)acetyl)-1-piperazinyl)pyrrolo[2,1-f][1,2,4]triazin-4-amine;
2-(4-((3-methoxyphenyl)acetyl)-1-piperazinyl)-N-(5-methyl-1H-pyrazol-3-yl)pyrrolo[2,1-f][1,2,4]triazin-4-amine;
2-(4-((3-chlorophenyl)acetyl)-1-piperazinyl)-N-(5-methyl-1H-pyrazol-3-yl)pyrrolo[2,1-f][1,2,4]triazin-4-amine;
2-(4-((3-fluorophenyl)acetyl)-1-piperazinyl)-N-(5-methyl-1H-pyrazol-3-yl)pyrrolo[2,1-f][1,2,4]triazin-4-amine;
2-(4-((2-chlorophenyl)acetyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(3-phenylpropanoyl)-1-piperazinyl)pyrrolo[2,1-f][1,2,4]triazin-4-amine;
N-(5-methyl-1H-pyrazol-3-yl)-2-(4-(4-(trifluoromethyl)benzoyl)-1-piperazinyl)pyrrolo[2,1-f][1,2,4]triazin-4-amine;
2-(4-(3-chlorobenzoyl)-1-piperazinyl)-N-(5-methyl-1H-pyrazol-3-yl)pyrrolo[2,1-f][1,2,4]triazin-4-amine;
2-(4-(3-methoxybenzoyl)-1-piperazinyl)-N-(5-methyl-1H-pyrazol-3-yl)pyrrolo[2,1-f][1,2,4]triazin-4-amine;
2-(4-(3-fluorobenzoyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(2-(trifluoromethyl)benzoyl)-1-piperazinyl)pyrrolo[2,1-f][1,2,4]triazin-4-amine;
N-(3-((4-(4-((5-methyl-1H-pyrazol-3-yl)amino)pyrrolo[2,1-f][1,2,4]triazin-2-yl)-1-piperazinyl)carbonyl)phenyl)acetamide;

N-(4-((4-(4-((5-methyl-1H-pyrazol-3-yl)amino)pyrrolo[2,1-f][1,2,4]triazin-2-yl)-1-piperazinyl)carbonyl)phenyl)acetamide;

2-(4-(2-chloro-6-fluorobenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-((2-methyl-3-pyridinyl)carbonyl)-1-piperazinyl)pyrrolo[2,1-f][1,2,4]triazin-4-amine;

N-(5-methyl-1H-pyrazol-3-yl)-2-(4-(3-pyridinylcarbonyl)-1-piperazinyl)pyrrolo[2,1-f][1,2,4]triazin-4-amine;

N-(5-methyl-1H-pyrazol-3-yl)-2-(4-((1-phenylcyclopentyl)carbonyl)-1-piperazinyl)pyrrolo[2,1-f][1,2,4]triazin-4-amine;

N-(5-methyl-1H-pyrazol-3-yl)-2-(4-(1,3-oxazol-2-ylcarbonyl)-1-piperazinyl)pyrrolo[2,1-f][1,2,4]triazin-4-amine;

N-(5-methyl-1H-pyrazol-3-yl)-2-(4-((1-phenylcyclobutyl)carbonyl)-1-piperazinyl)pyrrolo[2,1-f][1,2,4]triazin-4-amine;

3-(2-(4-(4-((5-methyl-1H-pyrazol-3-yl)amino)pyrrolo[2,1-f][1,2,4]triazin-2-yl)-1-piperazinyl)-2-oxoethyl)benzonitrile;

2-(4-(4-((5-methyl-1H-pyrazol-3-yl)amino)pyrrolo[2,1-f][1,2,4]triazin-2-yl)-1-piperazinyl)-2-oxo-1-phenylethanone;

N-(5-methyl-1H-pyrazol-3-yl)-2-(4-((4-(trifluoromethoxy)phenyl)acetyl)-1-piperazinyl)pyrrolo[2,1-f][1,2,4]triazin-4-amine;

2-(4-(2-fluoro-6-methoxybenzoyl)-1-piperazinyl)-N-(5-methyl-1H-pyrazol-3-yl)pyrrolo[2,1-f][1,2,4]triazin-4-amine;

2-(4-((2-bromophenyl)acetyl)-1-piperazinyl)-N-(5-methyl-1H-pyrazol-3-yl)pyrrolo[2,1-f][1,2,4]triazin-4-amine;

2-(4-((2,6-difluorophenyl)acetyl)-1-piperazinyl)-N-(5-methyl-1H-pyrazol-3-yl)pyrrolo[2,1-f][1,2,4]triazin-4-amine;

2-(4-(2-chloro-6-methylbenzoyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(2-(trifluoromethoxy)benzoyl)-1-piperazinyl)pyrrolo[2,1-f][1,2,4]triazin-4-amine;

N-(5-methyl-1H-pyrazol-3-yl)-2-(4-(4-(trifluoromethoxy)benzoyl)-1-piperazinyl)pyrrolo[2,1-f][1,2,4]triazin-4-amine;

N-(5-methyl-1H-pyrazol-3-yl)-2-(4-(1H-pyrazol-4-ylcarbonyl)-1-piperazinyl)pyrrolo[2,1-f][1,2,4]triazin-4-amine;

N-(5-methyl-1H-pyrazol-3-yl)-2-(4-((3-(trifluoromethoxy)phenyl)acetyl)-1-piperazinyl)pyrrolo[2,1-f][1,2,4]triazin-4-amine;

2-(4-((2R)-2-methoxy-2-phenylacetyl)-1-piperazinyl)-N-(5-methyl-1H-pyrazol-3-yl)pyrrolo[2,1-f][1,2,4]triazin-4-amine;

N-(5-methyl-1H-pyrazol-3-yl)-2-(4-(1,3-oxazol-5-ylcarbonyl)-1-piperazinyl)pyrrolo[2,1-f][1,2,4]triazin-4-amine;

N-(5-methyl-1H-pyrazol-3-yl)-2-(4-((2S)-2-phenylpropanoyl)-1-piperazinyl)pyrrolo[2,1-f][1,2,4]triazin-4-amine;

2-(2-(4-(4-((5-methyl-1H-pyrazol-3-yl)amino)pyrrolo[2,1-f][1,2,4]triazin-2-yl)-1-piperazinyl)-2-oxoethyl)benzonitrile;

N-(2-((4-(4-((5-methyl-1H-pyrazol-3-yl)amino)pyrrolo[2,1-f][1,2,4]triazin-2-yl)-1-piperazinyl)carbonyl)phenyl)acetamide;

2-(4-(5-isoxazolylcarbonyl)-1-piperazinyl)-N-(5-methyl-1H-pyrazol-3-yl)pyrrolo[2,1-f][1,2,4]triazin-4-amine;

tert-butyl 4-(4-chlorophenyl)-4-((4-(4-((5-methyl-1H-pyrazol-3-yl)amino)pyrrolo[2,1-f][1,2,4]triazin-2-yl)-1-piperazinyl)carbonyl)-1-piperidinecarboxylate;

1-(2,6-difluorophenyl)-2-(4-(4-((5-methyl-1H-pyrazol-3-yl)amino)pyrrolo[2,1-f][1,2,4]triazin-2-yl)-1-piperazinyl)-2-oxoethanol;

1-(4-fluorophenyl)-2-(4-(4-((5-methyl-1H-pyrazol-3-yl)amino)pyrrolo[2,1-f][1,2,4]triazin-2-yl)-1-piperazinyl)-2-oxoethanol;

2-(4-((4-(4-fluorophenyl)tetrahydro-2H-pyran-4-yl)carbonyl)-1-piperazinyl)-N-(5-methyl-1H-pyrazol-3-yl)pyrrolo[2,1-f][1,2,4]triazin-4-amine;

1-(4-chlorophenyl)-2-(4-(4-((5-methyl-1H-pyrazol-3-yl)amino)pyrrolo[2,1-f][1,2,4]triazin-2-yl)-1-piperazinyl)-2-oxoethanol;

2-(4-(2-(4-chlorophenyl)-3-methylbutanoyl)-1-piperazinyl)-N-(5-methyl-1H-pyrazol-3-yl)pyrrolo[2,1-f][1,2,4]triazin-4-amine;

2-(4-((4-fluoro-2-(trifluoromethyl)phenyl)acetyl)-1-piperazinyl)-N-(5-methyl-1H-pyrazol-3-yl)pyrrolo[2,1-f][1,2,4]triazin-4-amine;

2-(4-((4-chloro-2,6-difluorophenyl)acetyl)-1-piperazinyl)-N-(5-methyl-1H-pyrazol-3-yl)pyrrolo[2,1-f][1,2,4]triazin-4-amine;

2-(4-((4-fluorophenyl)(1-piperidinyl)acetyl)-1-piperazinyl)-N-(5-methyl-1H-pyrazol-3-yl)pyrrolo[2,1-f][1,2,4]triazin-4-amine;

2-(4-((2,6-difluoro-4-methoxyphenyl)acetyl)-1-piperazinyl)-N-(5-methyl-1H-pyrazol-3-yl)pyrrolo[2,1-f][1,2,4]triazin-4-amine;

2-(4-((1-(4-fluorophenyl)-2,2-dimethylcyclopropyl)carbonyl)-1-piperazinyl)-N-(5-methyl-1H-pyrazol-3-yl)pyrrolo[2,1-f][1,2,4]triazin-4-amine;

2-(4-((4-methoxy-2-(trifluoromethyl)phenyl)acetyl)-1-piperazinyl)-N-(5-methyl-1H-pyrazol-3-yl)pyrrolo[2,1-f][1,2,4]triazin-4-amine;

2-(4-((4-ethoxy-2,6-difluorophenyl)acetyl)-1-piperazinyl)-N-(5-methyl-1H-pyrazol-3-yl)pyrrolo[2,1-f][1,2,4]triazin-4-amine;

2-(4-(2,2-dimethylbutanoyl)-1-piperazinyl)-N-(5-methyl-1H-pyrazol-3-yl)pyrrolo[2,1-f][1,2,4]triazin-4-amine;

2-(4-((1-methylcyclohexyl)carbonyl)-1-piperazinyl)-N-(5-methyl-1H-pyrazol-3-yl)pyrrolo[2,1-f][1,2,4]triazin-4-amine;

2-methyl-1-(4-(4-((5-methyl-1H-pyrazol-3-yl)amino)pyrrolo[2,1-f][1,2,4]triazin-2-yl)-1-piperazinyl)-1-oxo-2-butanol;

tert-butyl (1,2-dimethyl-1-((4-(4-((5-methyl-1H-pyrazol-3-yl)amino)pyrrolo[2,1-f][1,2,4]triazin-2-yl)-1-piperazinyl)carbonyl)propyl)carbamate;

tert-butyl (4-((1,1-dimethyl-2-(4-(4-((5-methyl-1H-pyrazol-3-yl)amino)pyrrolo[2,1-f][1,2,4]triazin-2-yl)-1-piperazinyl)-2-oxoethyl)carbamoyl)cyclohexyl)carbamate;

tert-butyl (1,1-dimethyl-2-(4-(4-((5-methyl-1H-pyrazol-3-yl)amino)pyrrolo[2,1-f][1,2,4]triazin-2-yl)-1-piperazinyl)-2-oxoethyl)carbamate;

tert-butyl (3-((4-(4-((5-methyl-1H-pyrazol-3-yl)amino)pyrrolo[2,1-f][1,2,4]triazin-2-yl)-1-piperazinyl)carbonyl)tetrahydro-3-furanyl)carbamate;

N-(5-methyl-1H-pyrazol-3-yl)-2-(4-((1-(trifluoromethyl)cyclopropyl)carbonyl)-1-piperazinyl)pyrrolo[2,1-f][1,2,4]triazin-4-amine;

2-methyl-1-(4-(4-((5-methyl-1H-pyrazol-3-yl)amino)pyrrolo[2,1-f][1,2,4]triazin-2-yl)-1-piperazinyl)-1-oxo-2-propanol;

tert-butyl 4-methyl-4-((4-(4-((5-methyl-1H-pyrazol-3-yl)amino)pyrrolo[2,1-f][1,2,4]triazin-2-yl)-1-piperazinyl)carbonyl)-1-piperidinecarboxylate;
tert-butyl (1-((4-(4-((5-methyl-1H-pyrazol-3-yl)amino)pyrrolo[2,1-f][1,2,4]triazin-2-yl)-1-piperazinyl)carbonyl)cyclohexyl)carbamate;
tert-butyl (1-((4-(4-((5-methyl-1H-pyrazol-3-yl)amino)pyrrolo[2,1-f][1,2,4]triazin-2-yl)-1-piperazinyl)carbonyl)cyclobutyl)carbamate;
N-(5-methyl-1H-pyrazol-3-yl)-2-(4-((1-(trifluoromethyl)cyclobutyl)carbonyl)-1-piperazinyl)pyrrolo[2,1-f][1,2,4]triazin-4-amine;
(2R)-1,1,1-trifluoro-2-methyl-3-(4-(4-((5-methyl-1H-pyrazol-3-yl)amino)pyrrolo[2,1-f][1,2,4]triazin-2-yl)-1-piperazinyl)-3-oxo-2-propanol;
2-(4-(2,2-dimethylpropanoyl)-1-piperazinyl)-N-(5-methyl-1H-pyrazol-3-yl)pyrrolo[2,1-f][1,2,4]triazin-4-amine;
1-((4-(4-((5-methyl-1H-pyrazol-3-yl)amino)pyrrolo[2,1-f][1,2,4]triazin-2-yl)-1-piperazinyl)carbonyl)cyclopropanecarbonitrile;
N-(5-methyl-1H-pyrazol-3-yl)-2-(4-(trifluoroacetyl)-1-piperazinyl)pyrrolo[2,1-f][1,2,4]triazin-4-amine;
2-(4-((1-(4-chlorophenyl)cyclohexyl)carbonyl)-1-piperazinyl)-N-(5-methyl-1H-pyrazol-3-yl)pyrrolo[2,1-f][1,2,4]triazin-4-amine;
2-(4-(3-methyl-2-phenylbutanoyl)-1-piperazinyl)-N-(5-methyl-1H-pyrazol-3-yl)pyrrolo[2,1-f][1,2,4]triazin-4-amine;
2-(4-(2-(4-chlorophenyl)propanoyl)-1-piperazinyl)-N-(5-methyl-1H-pyrazol-3-yl)pyrrolo[2,1-f][1,2,4]triazin-4-amine;
2-(4-((1-(4-methylphenyl)cyclopentyl)carbonyl)-1-piperazinyl)-N-(5-methyl-1H-pyrazol-3-yl)pyrrolo[2,1-f][1,2,4]triazin-4-amine;
2-(4-(2-(4-chlorophenyl)-2-methylpropanoyl)-1-piperazinyl)-N-(5-methyl-1H-pyrazol-3-yl)pyrrolo[2,1-f][1,2,4]triazin-4-amine;
N-(2-(4-(4-((5-methyl-1H-pyrazol-3-yl)amino)pyrrolo[2,1-f][1,2,4]triazin-2-yl)-1-piperazinyl)-2-oxo-1-phenylethyl)acetamide;
tert-butyl((1R)-2-(4-(4-((5-methyl-1H-pyrazol-3-yl)amino)pyrrolo[2,1-f][1,2,4]triazin-2-yl)-1-piperazinyl)-2-oxo-1-phenylethyl)carbamate;
N-(5-methyl-1H-pyrazol-3-yl)-2-(4-((2S)-2-phenylbutanoyl)-1-piperazinyl)pyrrolo[2,1-f][1,2,4]triazin-4-amine;
N-(5-methyl-1H-pyrazol-3-yl)-2-(4-((2R)-2-phenylbutanoyl)-1-piperazinyl)pyrrolo[2,1-f][1,2,4]triazin-4-amine;
(1S)-2-(4-(4-((5-methyl-1H-pyrazol-3-yl)amino)pyrrolo[2,1-f][1,2,4]triazin-2-yl)-1-piperazinyl)-2-oxo-1-phenylethyl acetate;
2-(4-((1-(4-methylphenyl)cyclohexyl)carbonyl)-1-piperazinyl)-N-(5-methyl-1H-pyrazol-3-yl)pyrrolo[2,1-f][1,2,4]triazin-4-amine;
2-(4-((1-(4-methylphenyl)cyclopropyl)carbonyl)-1-piperazinyl)-N-(5-methyl-1H-pyrazol-3-yl)pyrrolo[2,1-f][1,2,4]triazin-4-amine;
2-(4-((1-(2-fluorophenyl)cyclopentyl)carbonyl)-1-piperazinyl)-N-(5-methyl-1H-pyrazol-3-yl)pyrrolo[2,1-f][1,2,4]triazin-4-amine;
2-(4-((1-(4-fluorophenyl)cyclopentyl)carbonyl)-1-piperazinyl)-N-(5-methyl-1H-pyrazol-3-yl)pyrrolo[2,1-f][1,2,4]triazin-4-amine;
tert-butyl (1-(4-chlorophenyl)-2-(4-(4-((5-methyl-1H-pyrazol-3-yl)amino)pyrrolo[2,1-f][1,2,4]triazin-2-yl)-1-piperazinyl)-2-oxoethyl)carbamate;
2-(4-(2-chloro-4,5-difluorobenzoyl)-1-piperazinyl)-N-(5-methyl-1H-pyrazol-3-yl)pyrrolo[2,1-f][1,2,4]triazin-4-amine;
tert-butyl (2-((4-(4-((5-methyl-1H-pyrazol-3-yl)amino)pyrrolo[2,1-f][1,2,4]triazin-2-yl)-1-piperazinyl)carbonyl)phenyl)carbamate;
N-(5-methyl-1H-pyrazol-3-yl)-2-(4-(2-(methylsulfonyl)benzoyl)-1-piperazinyl)pyrrolo[2,1-f][1,2,4]triazin-4-amine;
2-(4-(2-(3,5-dimethyl-1H-pyrazol-4-yl)benzoyl)-1-piperazinyl)-N-(5-methyl-1H-pyrazol-3-yl)pyrrolo[2,1-f][1,2,4]triazin-4-amine;
2-(4-(2-bromobenzoyl)-1-piperazinyl)-N-(5-methyl-1H-pyrazol-3-yl)pyrrolo[2,1-f][1,2,4]triazin-4-amine;
2-(4-(2,4-dichlorobenzoyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(2-phenoxybenzoyl)-1-piperazinyl)pyrrolo[2,1-f][1,2,4]triazin-4-amine;
2-(4-(2-biphenylylcarbonyl)-1-piperazinyl)-N-(5-methyl-1H-pyrazol-3-yl)pyrrolo[2,1-f][1,2,4]triazin-4-amine;
2-(4-((2-chloro-3-pyridinyl)carbonyl)-1-piperazinyl)-N-(5-methyl-1H-pyrazol-3-yl)pyrrolo[2,1-f][1,2,4]triazin-4-amine;
N-(5-methyl-1H-pyrazol-3-yl)-2-(4-(2-(phenoxymethyl)benzoyl)-1-piperazinyl)pyrrolo[2,1-f][1,2,4]triazin-4-amine;
2-(4-((1-(2-chloro-6-fluorophenyl)cyclohexyl)carbonyl)-1-piperazinyl)-N-(5-methyl-1H-pyrazol-3-yl)pyrrolo[2,1-f][1,2,4]triazin-4-amine;
(2R)-1-(4-(4-((5-methyl-1H-pyrazol-3-yl)amino)pyrrolo[2,1-f][1,2,4]triazin-2-yl)-1-piperazinyl)-1-oxo-2-phenyl-2-propanol;
(2S)-1-(4-(4-((5-methyl-1H-pyrazol-3-yl)amino)pyrrolo[2,1-f][1,2,4]triazin-2-yl)-1-piperazinyl)-1-oxo-2-phenyl-2-propanol;
(2R)-1-(4-(4-((5-methyl-1H-pyrazol-3-yl)amino)pyrrolo[2,1-f][1,2,4]triazin-2-yl)-1-piperazinyl)-1-oxo-4-phenyl-2-butanol;
(2S)-1-(4-(4-((5-methyl-1H-pyrazol-3-yl)amino)pyrrolo[2,1-f][1,2,4]triazin-2-yl)-1-piperazinyl)-1-oxo-3-phenyl-2-propanol;
(1S)-2-(4-(4-((5-methyl-1H-pyrazol-3-yl)amino)pyrrolo[2,1-f][1,2,4]triazin-2-yl)-1-piperazinyl)-2-oxo-1-phenylethanol;
(1R)-2-(4-(4-((5-methyl-1H-pyrazol-3-yl)amino)pyrrolo[2,1-f][1,2,4]triazin-2-yl)-1-piperazinyl)-2-oxo-1-phenylethanol;
1-(2-fluorophenyl)-2-(4-(4-(5-methyl-1H-pyrazol-3-yl)amino)pyrrolo[2,1-f][1,2,4]triazin-2-yl)-1-piperazinyl)-2-oxoethanol;
N-(5-methyl-1H-pyrazol-3-yl)-2-(4-(2-phenylbutanoyl)-1-piperazinyl)pyrrolo[2,1-f][1,2,4]triazin-4-amine;
tert-butyl (1-((4-(4-((5-methyl-1H-pyrazol-3-yl)amino)pyrrolo[2,1-f][1,2,4]triazin-2-yl)-1-piperazinyl)carbonyl)-2,3-dihydro-1H-inden-1-yl)carbamate;
or salt thereof.

ABBREVIATIONS

The following abbreviations may be employed in the methods of preparation and Examples:

| | |
|---|---|
| h = | hours |
| DCM = | dichloromethane |

| | |
|---|---|
| THF = | tetrahydrofuran |
| HPLC = | high performance liquid chromatography |
| DIEA = | diisopropylethyl amine |
| i-PrOH = | isopropyl alcohol |
| TFA = | trifluoroacetic acid |
| min = | minutes |
| DMF = | dimethylformamide |
| EDC = | N-(3-Dimethylaminopropyl)N'-ethylcarbodiimide |
| HOBt = | hydroxybenzotriazole |
| NMP = | N-methylpyrolidinone |
| EtOAc = | ethyl acetate |
| AcOH = | acetic acid |
| BOP reagent = | benzotriazole-1-yl-oxy-tris-(dimethylamino)-phasphoniumhexafluorophosphate |
| brine = | saturated aqueous sodium chloride solution |
| Et$_3$N = | triethylamine |
| $t_R$ = | retention time |

Methods of Preparation

Compounds of formula I may generally be prepared according to the following schemes and the knowledge of one skilled in the art.

Scheme 1

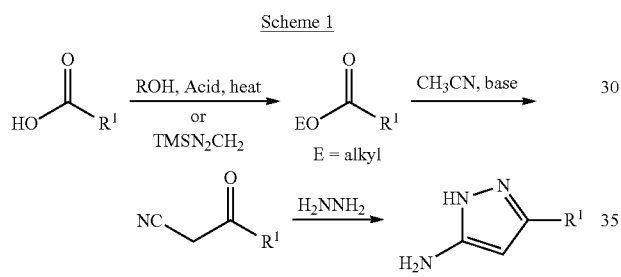

Amino pyrazoles may be prepared according to Scheme 1. An appropriately substituted carboxylic acid may be esterified using acid catalysis and heat or through the use of an esterification reagent such as TMSCH$_2$N$_2$. Condensation with acetonitrile under basic conditions afford β-cyano ketones that may be cyclized to the pyrazoles using hydrazine.

Scheme 2

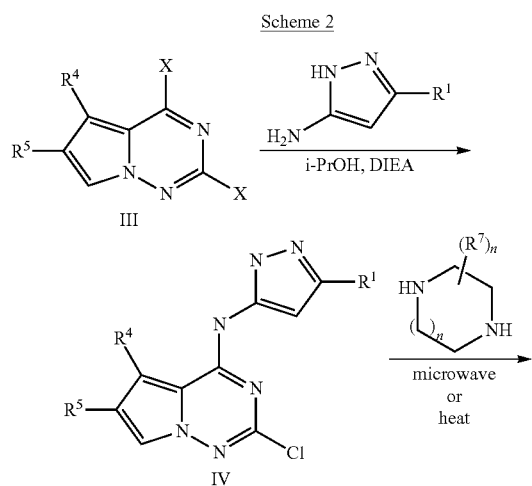

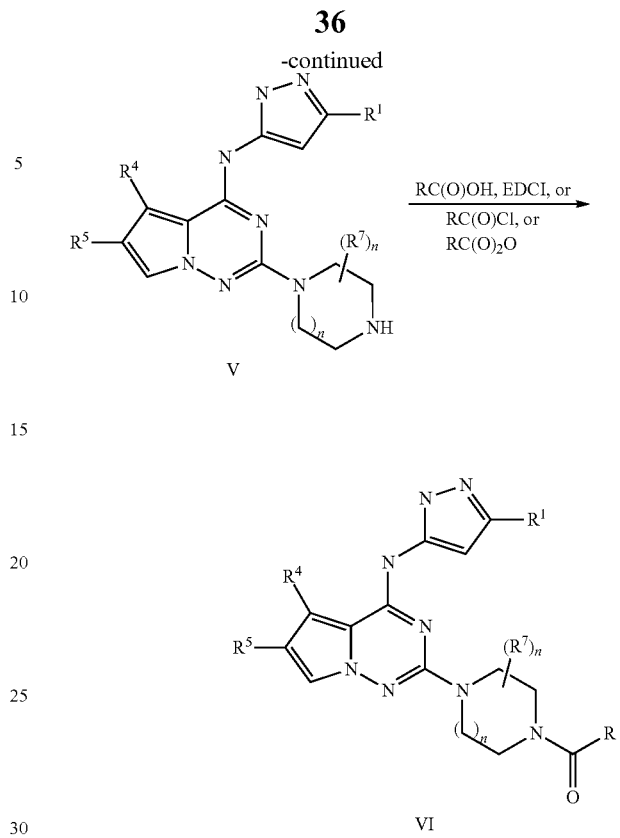

A suitable dihalo-pyrrolotriazine III may be treated with an appropriately substituted amino pyrazole in a suitable solvent such as isopropanol in the presence of a based such as diisopropylethylamine to afford compounds of general formula IV. The second halogen may be displaced by diaamines such as piperazine or substituted piperazines either thermally or under microwave conditions and using either the amine or dimethylformamide or dimethylacetamide as solvent, in the presence or absence of a transition metal catalyst such as Pd and a phosphorous-based ligand, to afford compounds of formula V. Compound V could be further converted into amide derivative VI using standard coupling conditions (EDCI) or through the coupling of acid chlorides, anhydrides, among other routes. Similarly, V could be reacted with chloroformate, isocyanate and sulfonyl chloride to form carbamate, urea and sulfonamide derivatives; respectively.

Compounds of formula XIII, where $R^x$ is aryl or heteroaryl or alkyl may be synthesized using a general methodology as shown in Scheme 4. Bromination of intermediate VII would give two region-isomeric bromides (VIII and IX). Regioisomer IX maybe treated with suitably substituted pyrazole to afford X. Transition metal promoted coupling of the bromide with suitably activated Rx maybe carried out to give XI. The second halogen may be displaced by amines either thermally or under microwave conditions using either the amine or dimethylformamide or dimethylacetamide as solvent, in the presence or absence of a transition metal catalyst such as Pd and a phosphorous-based ligand, to afford compounds of formula XII which could be converted into amide XIII Scheme 3
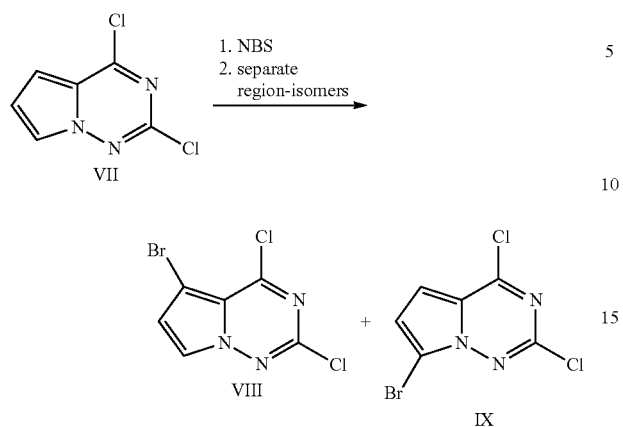
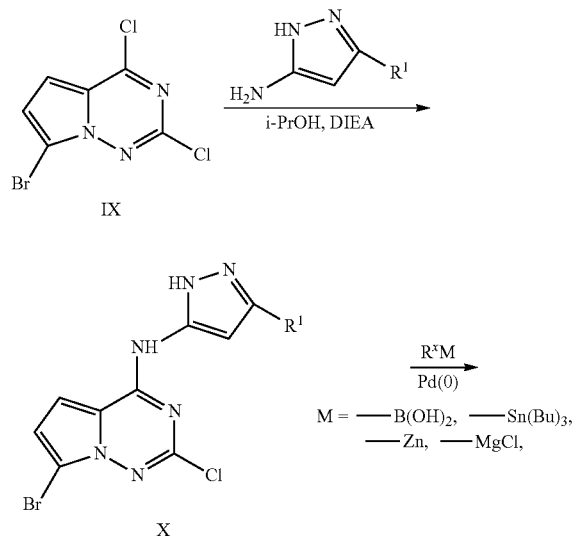
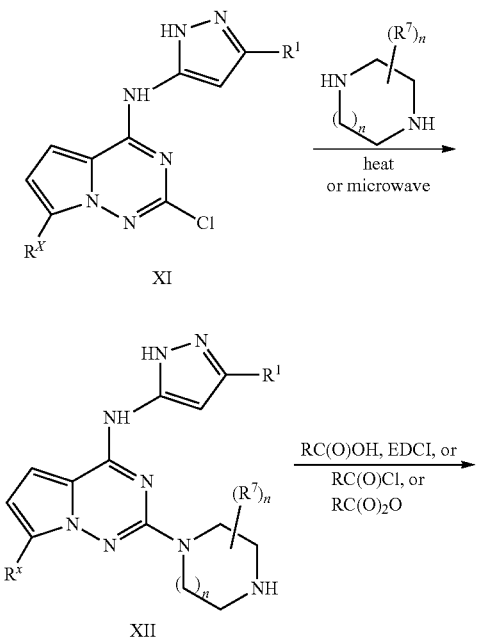
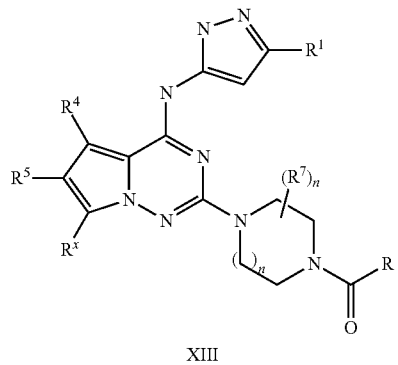
Similarly, regioisomer VIII maybe converted into compound of general formula XIV using protocol as described in Scheme 4.
Scheme 4
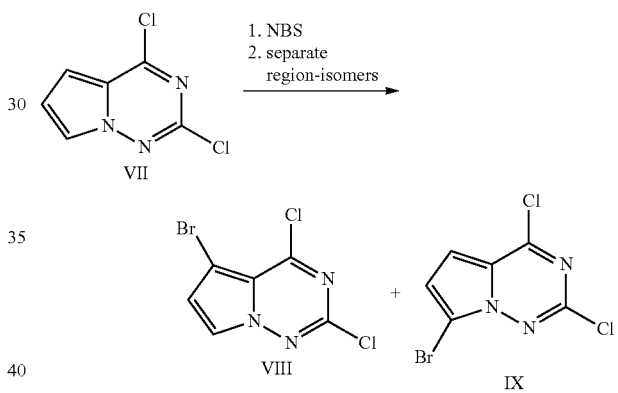
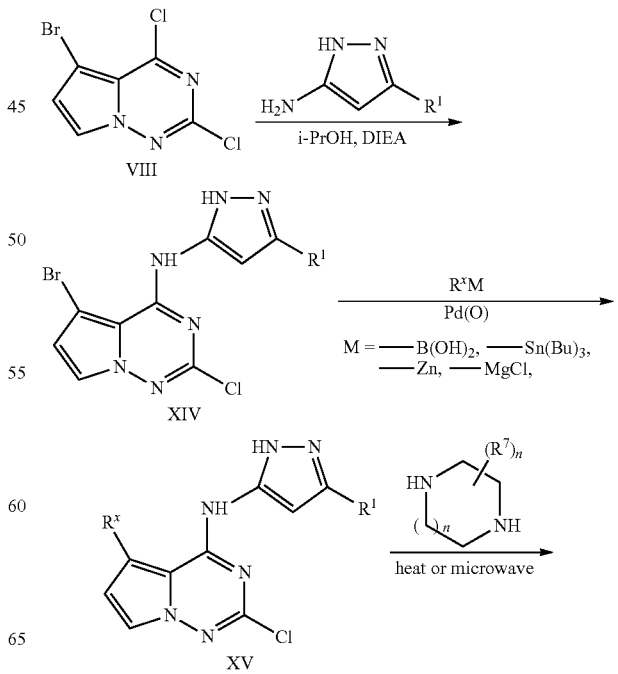

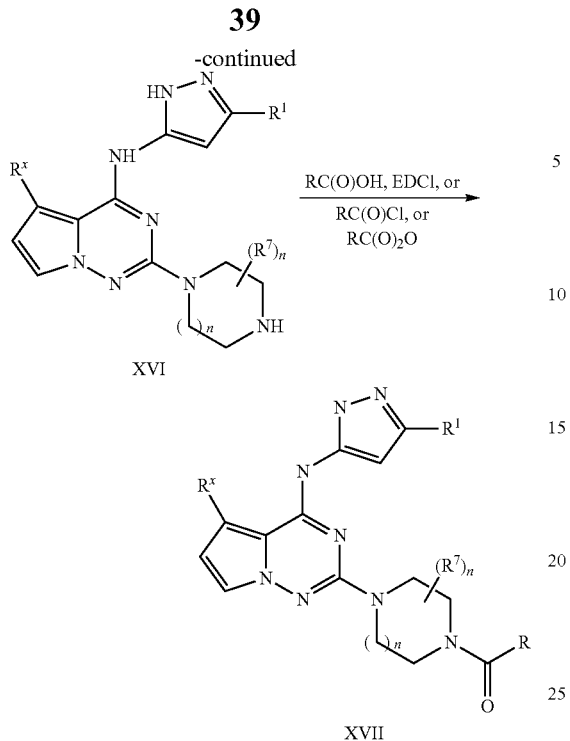

XVI

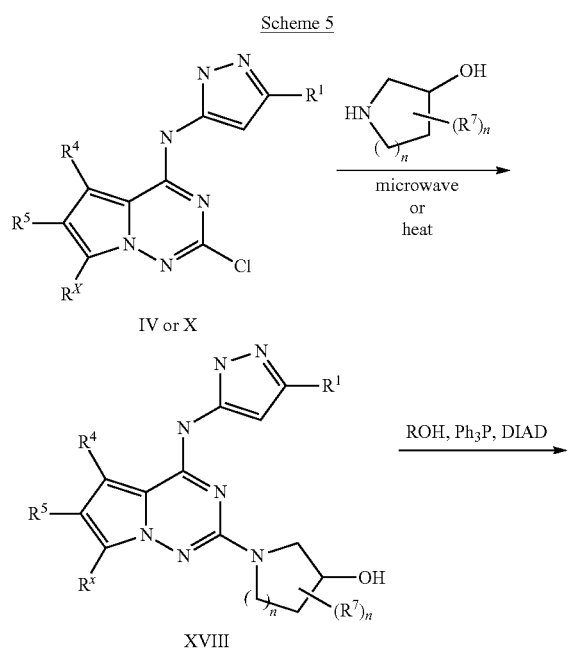

XVII

Compound of general formula XIX in which Rx is H or aryl or heteroaryl or alkyl may be synthesized using a general methodology as shown in Scheme 5. Intermediates IV or X could be coupled with substituted hydroxy group containing saturated amino heterocycles using microwave or thermal conditions. The resulting XVIII could be combined with phenol under Mitsunobu reaction conditions to afford compound XIX.

Scheme 5

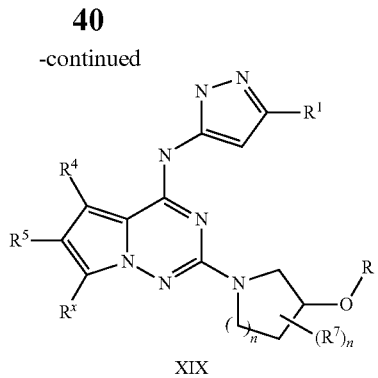

XIX

Preparative Example 1

3-isopropyl-1H-pyrazol-5-amine

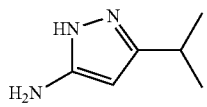

Method One

1A. Preparation of 4-methyl-3-oxopentanenitrile

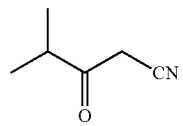

A suspension of NaH (60% dispersion in mineral oil, 1.05 g, 0.026 mol) in 1,4-dioxane (20 mL), was treated with CH$_3$CN (1.5 mL, 0.028 mol). The reaction mixture was stirred at ambient temperature for 20 minutes, then ethyl isobutyrate (3 mL, 0.023 mol) was added. The reaction mixture was heated to 55° C. for 4 h, and then cooled to ambient temperature and stirred overnight. Water (40 mL) was added at 0° C., and the unreacted starting material was extracted with DCM (50 mL). The aqueous layer was acidified with 1N HCl to pH ~5 and then extracted with DCM (2×50 mL). The combined organic layers were dried (Na$_2$SO$_4$), filtered and concentrated to afford the desired product (1.8 g, 67%). $^1$HNMR (400M Hz, CD$_3$OD) δ 3.52 (s, 1H), 2.72-2.80 (m, 1H), 1.14 (d, J=6.8 Hz).

2B. Preparation of 3-isopropyl-1H-pyrazol-5-amine

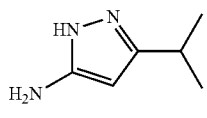

To a mixture of 4-methyl-3-oxopentanenitrile (0.9 g, 0.008 mole) in ethyl alcohol (5 mL) was added hydrazine (0.25 mL, 0.008 mole). The reaction mixture was refluxed for 1 hour and then cooled to room temperature. The reaction mixture was concentrated and the residue was dissolved in MeOH (2 mL). The crude product was loaded on a sulfuric acid bound resin (AG 50W-X2, hydrogen form, 100-200 mesh, BioRad), washed with MeOH (50 mL), then washed with 2N NH$_3$ in methanol (10 mL). The ammonia washes were combined and concentrated to afford the desired product (700 mg, 68%). $^1$HNMR (400 MHz, MeOD) δ 5.44 (s, 1H), 2.84-2.90 (m, 1H), 1.24 (d, J=6.4 Hz).

Preparative Example 2

3-ethyl-1H-pyrazol-5-amine

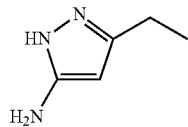

Method Two

2A. Preparation of 3-oxopentanenitrile

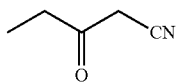

A solution of n-BuLi (1.6 M in Hexane, 5 mL, 8 mmol) in THF (15 mL) at −78° C. was treated with CH$_3$CN (0.4 mL, 8 mmol). The reaction mixture was stirred at −78° C. for 1 h, and then ethyl propionate (0.45 mL, 4 mmol) was added. The reaction mixture was stirred at −40° C. for 2 h, then slowly warmed to room temperature. The reaction was quenched with 1N HCl and brought to pH~5. The solution was extracted with diethyl ether (20 mL), dried (Na$_2$SO$_4$), then carefully concentrated under reduced pressure below 20° C. The crude product (0.4 g) was used in the next step without purification.

2B. Preparation of 3-ethyl-1H-pyrazol-5-amine

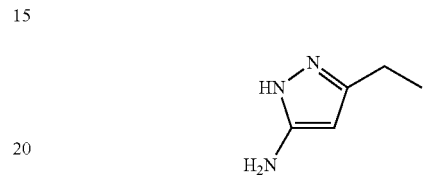

To a mixture of 3-oxopentanenitrile in ethanol (5 mL), was added hydrazine (0.2 mL, 6 mmol). The mixture was refluxed for 1 h, and then concentrated under reduced pressure. The residue was diluted with methanol (1 mL) and purified by preparative reversed-phase HPLC(YMC ODS-A 5um 30×100 mm, 10-90% aqueous methanol containing 0.1% TFA, 15 min gradient, monitored at 220 nm) to give 3-ethyl-1H-pyrazol-5-amine (0.3 g, 68%). $^1$HNMR (MeOD) δ 5.54 (s, 1H), 2.60 (q, 2H, J=7.6 Hz), 1.25 (t, 3H, J=7.6 Hz).

The compounds listed in Table 1 were prepared as described for Preparative Examples 1 or 2 as indicated.

TABLE 1

| # | R | Compound name | Method | HPLC Ret Time (min) |
|---|---|---|---|---|
| A | Et | 3-ethyl-1H-pyrazol-5-amine | 2 | 1.28[a] |
| B | i-Pr | 3-isopropyl-1H-pyrazol-5-amine | 1 | 1.11[a] |
| C | s-Bu | 3-sec-butyl-1H-pyrazol-5-amine | 2 | 0.76[a] |
| D | i-Bu | 3-isobutyl-1H-pyrazol-5-amine | 2 | 0.68[a] |
| E | c-Bu | 3-cyclobutyl-1H-pyrazol-5-amine | 2 | 0.56[a] |
| F | Benzyl | 3-benzyl-1H-pyrazol-5-amine | 1 | 1.75[a] |
| G | cyclopropylmethyl | 3-(cyclopropylmethyl)-1H-pyrazol-5-amine | 2 | 0.65[a] |
| H | trans-2-methylcyclopropyl | 3-(trans-2-methylcyclopropyl)-1H-pyrazol-5-amine | 2 | 0.76[a] |
| I | trans-2-phenylcyclopropyl | 3-(trans-2-phenylcyclopropyl)-1H-pyrazol-5-amine | 2 | 1.82[b] |

TABLE 1-continued

| # | R | Compound name | Method | HPLC Ret Time (min) |
|---|---|---|---|---|
| J | (1-methylcyclopropyl group) | 3-(1-methylcyclopropyl)-1H-pyrazol-5-amine | 2 | 0.62[a] |

HPLC Conditions:
(a) YMC S5 Combiscreen ODS 4.6 × 50 mm, 10-90% aqueous methanol containing 0.2% $H_3PO_4$, 4 min gradient, monitored at 220 or 254 nm)
(b) Chromolith SpeedROD 4.6 × 50 mm, 10-90% aqueous methanol containing 0.1% TFA, 4 min gradient, monitored at 220 or 254 nm)

Example 1

(4-(4-(3-methyl-1H-pyrazol-5-ylamino)pyrrolo[1,2-f][1,2,4]triazin-2-yl)piperazin-1-yl)(phenyl)methanone

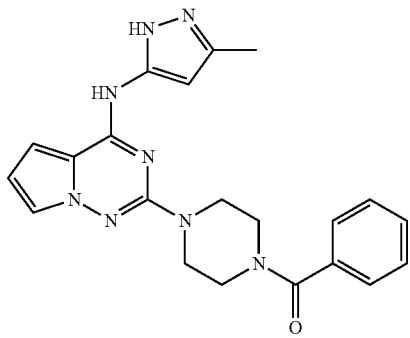 [SMILES: Cc1cc(Nc2nc(N3CCN(C(=O)c4ccccc4)CC3)nn3cccc23)[nH]n1]

1A. Preparation of 2-chloro-N-(5-methyl-1H-pyrazol-3-yl)pyrrolo[1,2-f][1,2,4]triazin-4-amine

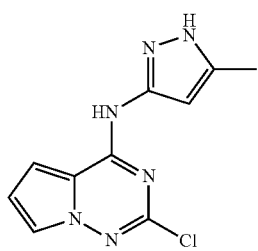 [SMILES: Cc1cc(Nc2nc(Cl)nn3cccc23)n[nH]1]

3-methyl-1H-pyrazol-5-amine (387 mg, 3.99 mmol) was added to a stirred suspension of 2,4-dichloropyrrolo[1,2-f][1,2,4]triazine (500 mg, 2.66 mmol) in a mixture of 2-propanol and triethylamine (4:0.2 mL). The reaction mixture was stirred at 45° C. for 16 hours. The reaction mixture was cooled at room temperature and concentrated in vacuo. The crude was purified using silica gel column chromatography (dichloromethane-methanol (98:2 to 94:6) gradient). The fractions were collected, analyzed, combined and concentrated to afford 350 mg of 2-chloro-N-(5-methyl-1H-pyrazol-3-yl)pyrrolo[1,2-f][1,2,4]triazin-4-amine.

MS (ESI) m/z 249.06 (M+H)

1H NMR (CDCl$_3$) δ ppm 8.75 (s, 1H), 7.66 (s, 1H), 6.71 (s, 1H), 6.05 (br s, 1H), 2.27 (s, 3H)

1B. Preparation of N-(3-methyl-1H-pyrazol-5-yl)-2-(piperazin-1-yl)pyrrolo[1,2-f][1,2,4]triazin-4-amine

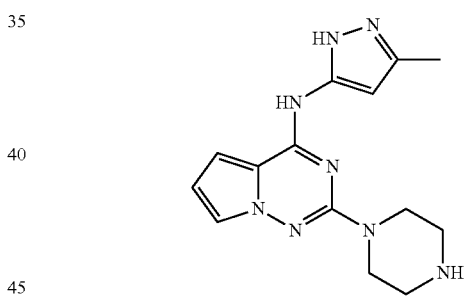

In a 100 mL round-bottomed flask equipped with a stir bar was charged with 2-chloro-N-(5-methyl-1H-pyrazol-3-yl)pyrrolo[1,2-f][1,2,4]triazin-4-amine (5 g, 20.11 mmol), piperazine (8.66 g, 101 mmol) and N-methylpyrrolidine (5 mL). The reaction mixture was stirred at 125° C. for 2 h, when the LC MS of the crude reaction showed disappearance of starting material. The viscous reaction mixture was allowed to cool to room temperature and a mixture of MeOH-DCM (20 mL, 1:1) was added. The liquid was decanted carefully to avoid transfer of excess piperizine that had solidified on the upper walls of the flask. The solution was slowly added to 300 mL of diethyl ether with vigorous stirring for 30 min. The white precipitate was filtered and washed with ether to give 5 gm of N-(5-methyl-1H-pyrazol-3-yl)-2-(piperazin-1-yl)pyrrolo[1,2-f][1,2,4]triazin-4-amine.

MS (ESI) m/z 299.16 (M+H)

1H NMR (CD$_3$OD) δ ppm 7.375 (d, 1H, J=1.83 Hz), 6.82 (d, 1H, J=3.97 Hz), 6.35-6.57 (m, 2H), 3.60-3.71 (m, 4H), 2.88-3.00 (m, 4H), 2.32 (s, 3H)

1C. Preparation of (4-(4-(3-methyl-1H-pyrazol-5-ylamino)pyrrolo[1,2-f][1,2,4]triazin-2-yl)piperazin-1-yl)(phenyl)methanone TFA salt A mixture of N-(3-methyl-1H-pyrazol-5-yl)-2-(piperazin-1-yl)pyrrolo[1,2-f][1,2,4]triazin-4-amine (20 mg, 0.06 mmol) in DMF (1 mL) was treated with benzoic acid (10 mg, 0.08 mmol), N,N,N',N'-tetramethyl-O-(benzotriazol-1-yl) uronium tetrafluoroborate (20 mg, 0.06 mmol), and DIEA (0.1 mL, 0.59 mmol). The reaction was stirred at room temperature overnight. The mixture was diluted with methanol and purified with preparative reversed-phase HPLC(YMC ODS-A 20×100 mm, 10-90% aqueous methanol containing 0.1% TFA, 10 min gradient, monitored at 220 nm) to give (4-(4-(3-methyl-1H-pyrazol-5-ylamino)pyrrolo[1,2-f][1,2,4]triazin-2-yl)piperazin-1-yl)(phenyl)methanone TFA salt (11 mg).

m/z=403.1 (M+H)

$^1$HNMR (CD$_3$OD) δ 10.22 (s, 1H), 8.18 (d, 1H, J=7.6 Hz), 7.77 (d, 2H, J=7.6 Hz), 7.43 (m, 5H), 7.00 (s, 1H), 6.36 (s, 1H), 6.28 (s, 1H), 4.33 (d, 2H, J=13.2 Hz), 4.02 (s, 1H), 3.23 (t, 2H, J=7.6 Hz), 1.84 (m, 3H), 1.54 (m, 2H), 0.88 (m, 2H), 0.63 (m, 2H).

The following compounds in Table 1 have been synthesized utilizing the procedures described in Example 1.

TABLE 1

| Ex. No. | Structure | Name | HPLC Ret. time (min) | m/z [M + H] |
|---|---|---|---|---|
| 2 | 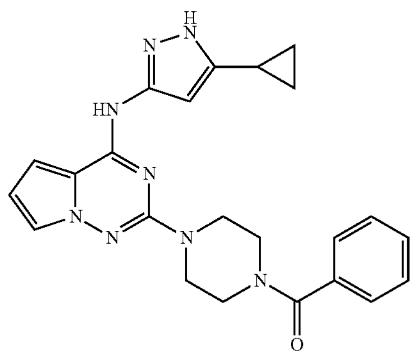 [SMILES: O=C(c1ccccc1)N1CCN(c2nc(Nc3cc(C4CC4)[nH]n3)c3cccn3n2)CC1] | (4-(4-(5-cyclopropyl-1H-pyrazol-3-ylamino)pyrrolo[1,2-f][1,2,4]triazin-2-yl)piperazin-1-yl)(phenyl)methanone | 1.98 | 429.21 |
| 3 | 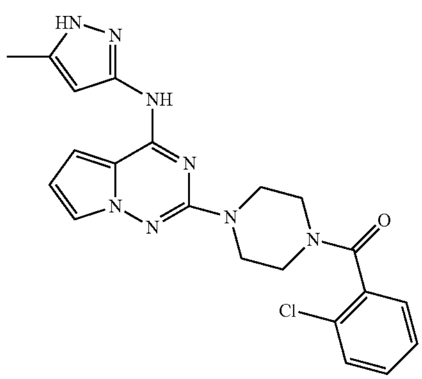 [SMILES: Cc1cc(Nc2nc(N3CCN(C(=O)c4ccccc4Cl)CC3)nn3cccc23)n[nH]1] | 2-(4-(2-chlorobenzoyl)-1-piperazinyl)-N-(5-methyl-1H-pyrazol-3-yl)pyrrolo[2,1-f][1,2,4]triazin-4-amine | 2.07 | 437.08 |
| 4 | 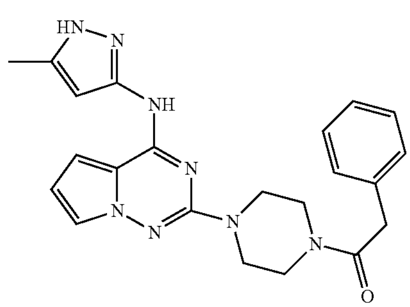 [SMILES: Cc1cc(Nc2nc(N3CCN(C(=O)Cc4ccccc4)CC3)nn3cccc23)n[nH]1] | N-(5-methyl-1H-pyrazol-3-yl)-2-(4-(phenylacetyl)-1-piperazinyl)pyrrolo[2,1-f][1,2,4]triazin-4-amine | 1.98 | 417.22 |

TABLE 1-continued

| Ex. No. | Structure | Name | HPLC Ret. time (min) | m/z [M + H] |
|---|---|---|---|---|
| 5 | 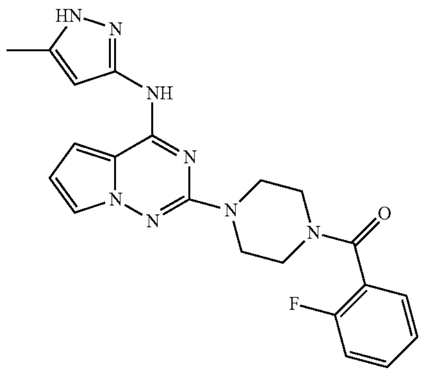 [SMILES: Cc1cc(Nc2nc(N3CCN(C(=O)c4ccccc4F)CC3)nn3cccc23)n[nH]1] | 2-(4-(2-fluorobenzoyl)-1-piperazinyl)-N-(5-methyl-1H-pyrazol-3-yl)pyrrolo[2,1-f][1,2,4]triazin-4-amine | 1.96 | 421.20 |
| 6 | 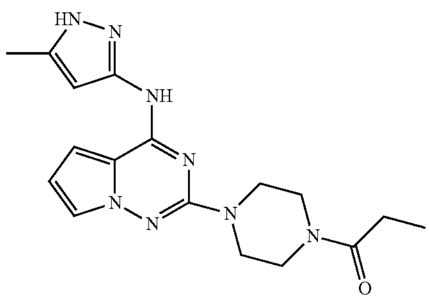 [SMILES: CCC(=O)N1CCN(c2nc(Nc3cc(C)[nH]n3)c3cccn3n2)CC1] | N-(5-methyl-1H-pyrazol-3-yl)-2-(4-propionyl-1-piperazinyl)pyrrolo[2,1-f][1,2,4]triazin-4-amine | 1.60 | 355.20 |
| 7 | 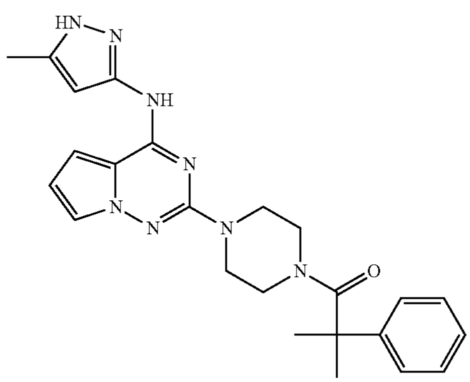 [SMILES: Cc1cc(Nc2nc(N3CCN(C(=O)C(C)(C)c4ccccc4)CC3)nn3cccc23)n[nH]1] | 2-(4-(2-methyl-2-phenylpropanoyl)-1-piperazinyl)-N-(5-methyl-1H-pyrazol-3-yl)pyrrolo[2,1-f][1,2,4]triazin-4-amine | 2.62 | 445.23 |
| 8 | 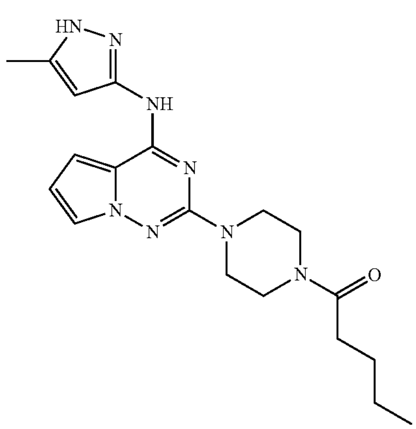 [SMILES: CCCCC(=O)N1CCN(c2nc(Nc3cc(C)[nH]n3)c3cccn3n2)CC1] | N-(5-methyl-1H-pyrazol-3-yl)-2-(4-pentanoyl-1-piperazinyl)pyrrolo[2,1-f][1,2,4]triazin-4-amine | 2.28 | 383.22 |

TABLE 1-continued

| Ex. No. | Structure | Name | HPLC Ret. time (min) | m/z [M + H] |
|---|---|---|---|---|
| 9 | 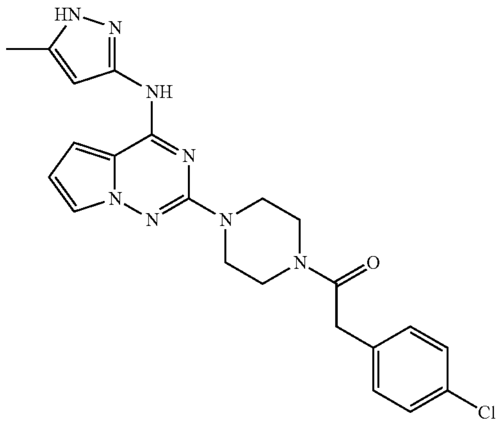 [SMILES: Cc1cc(Nc2nc(N3CCN(C(=O)Cc4ccc(Cl)cc4)CC3)nn3cccc23)n[nH]1] | 2-(4-((4-chlorophenyl)acetyl)-1-piperazinyl)-N-(5-methyl-1H-pyrazol-3-yl)pyrrolo[2,1-f][1,2,4]triazin-4-amine | 2.48 | 451.16 |
| 10 | 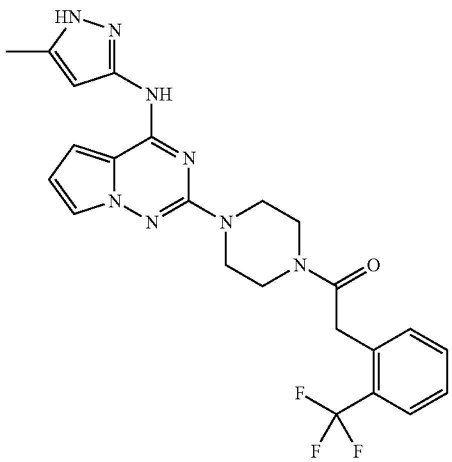 [SMILES: Cc1cc(Nc2nc(N3CCN(C(=O)Cc4ccccc4C(F)(F)F)CC3)nn3cccc23)n[nH]1] | N-(5-methyl-1H-pyrazol-3-yl)-2-(4-((2-(trifluoromethyl)phenyl)acetyl)-1-piperazinyl)pyrrolo[2,1-f][1,2,4]triazin-4-amine | 2.55 | 485.16 |
| 11 | 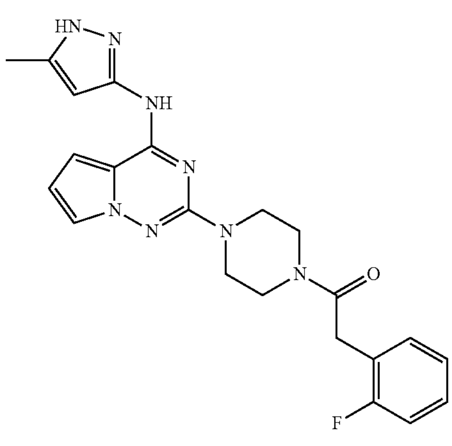 [SMILES: Cc1cc(Nc2nc(N3CCN(C(=O)Cc4ccccc4F)CC3)nn3cccc23)n[nH]1] | 2-(4-((2-fluorophenyl)acetyl)-1-piperazinyl)-N-(5-methyl-1H-pyrazol-3-yl)pyrrolo[2,1-f][1,2,4]triazin-4-amine | 2.36 | 435.17 |

TABLE 1-continued
| Ex. No. | Structure | Name | HPLC Ret. time (min) | m/z [M + H] |
|---|---|---|---|---|
| 12 | 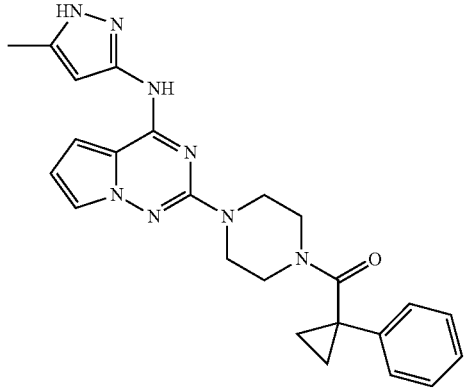 [SMILES: Cc1cc(Nc2nc(N3CCN(C(=O)C4(c5ccccc5)CC4)CC3)nn3cccc23)n[nH]1] | N-(5-methyl-1H-pyrazol-3-yl)-2-(4-((1-phenylcyclopropyl)carbonyl)-1-piperazinyl)pyrrolo[2,1-f][1,2,4]triazin-4-amine | 2.46 | 443.21 |
| 13 | 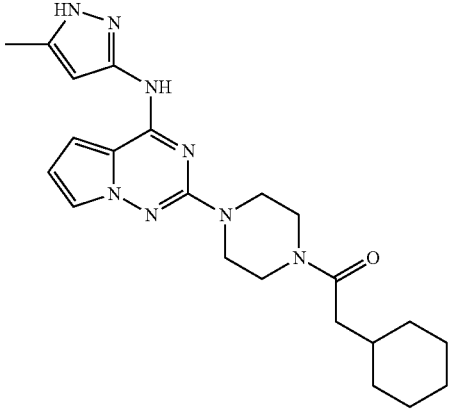 [SMILES: Cc1cc(Nc2nc(N3CCN(C(=O)CC4CCCCC4)CC3)nn3cccc23)n[nH]1] | 2-(4-(cyclohexylacetyl)-1-piperazinyl)-N-(5-methyl-1H-pyrazol-3-yl)pyrrolo[2,1-f][1,2,4]triazin-4-amine | 2.57 | 423.27 |
| 14 | 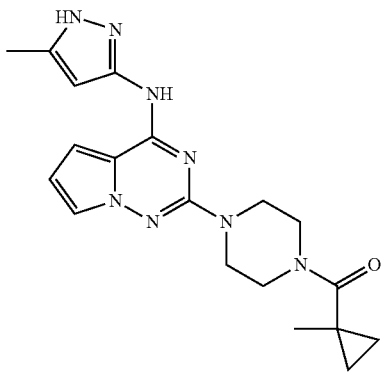 [SMILES: Cc1cc(Nc2nc(N3CCN(C(=O)C4(C)CC4)CC3)nn3cccc23)n[nH]1] | 2-(4-((1-methylcyclopropyl)carbonyl)-1-piperazinyl)-N-(5-methyl-1H-pyrazol-3-yl)pyrrolo[2,1-f][1,2,4]triazin-4-amine | 2.07 | 381.21 |

TABLE 1-continued
| Ex. No. | Structure | Name | HPLC Ret. time (min) | m/z [M + H] |
|---|---|---|---|---|
| 15 | 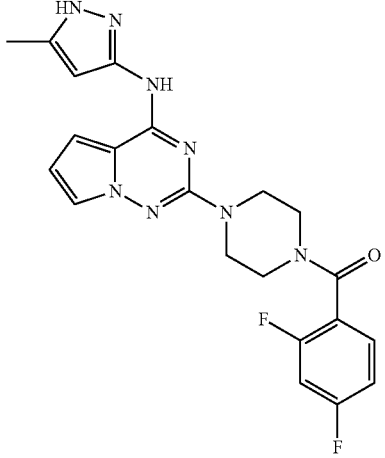 [SMILES: Cc1cc(Nc2nc(N3CCN(C(=O)c4ccc(F)cc4F)CC3)nn3cccc23)n[nH]1] | 2-(4-(2,4-difluorobenzoyl)-1-piperazinyl)-N-(5-methyl-1H-pyrazol-3-yl)pyrrolo[2,1-f][1,2,4]triazin-4-amine | 2.33 | 439.16 |
| 16 | 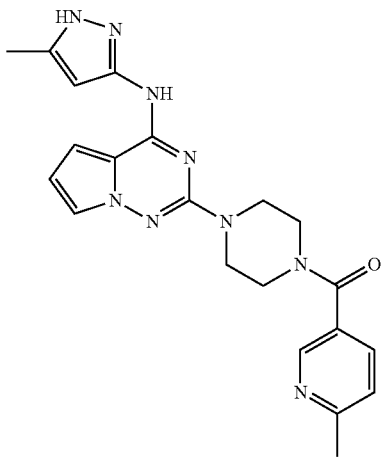 | N-(5-methyl-1H-pyrazol-3-yl)-2-(4-((6-methyl-3-pyridinyl)carbonyl)-1-piperazinyl)pyrrolo[2,1-f][1,2,4]triazin-4-amine | 1.93 | 418.20 |
| 17 | 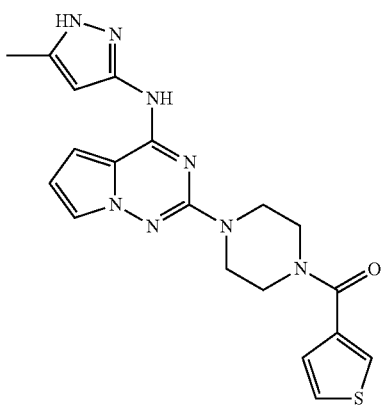 [SMILES: Cc1cc(Nc2nc(N3CCN(C(=O)c4ccsc4)CC3)nn3cccc23)n[nH]1] | N-(5-methyl-1H-pyrazol-3-yl)-2-(4-(3-thienylcarbonyl)-1-piperazinyl)pyrrolo[2,1-f][1,2,4]triazin-4-amine | 2.16 | 409.13 |

TABLE 1-continued

| Ex. No. | Structure | Name | HPLC Ret. time (min) | m/z [M + H] |
|---|---|---|---|---|
| 18 | 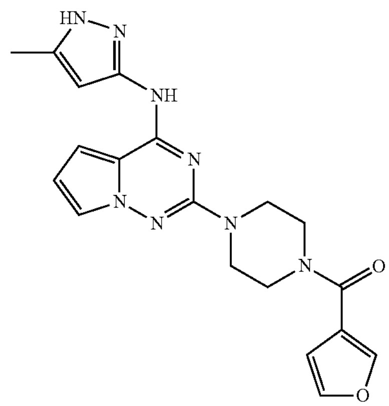 [SMILES: Cc1cc(Nc2nc(N3CCN(C(=O)c4ccoc4)CC3)nn3cccc23)n[nH]1] | 2-(4-(3-furoyl)-1-piperazinyl)-N-(5-methyl-1H-pyrazol-3-yl)pyrrolo[2,1-f][1,2,4]triazin-4-amine | 2.09 | 393.17 |
| 19 | 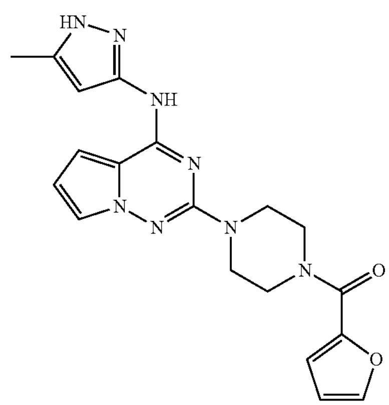 [SMILES: Cc1cc(Nc2nc(N3CCN(C(=O)c4ccco4)CC3)nn3cccc23)n[nH]1] | 2-(4-(2-furoyl)-1-piperazinyl)-N-(5-methyl-1H-pyrazol-3-yl)pyrrolo[2,1-f][1,2,4]triazin-4-amine | 2.09 | 393.15 |
| 20 | 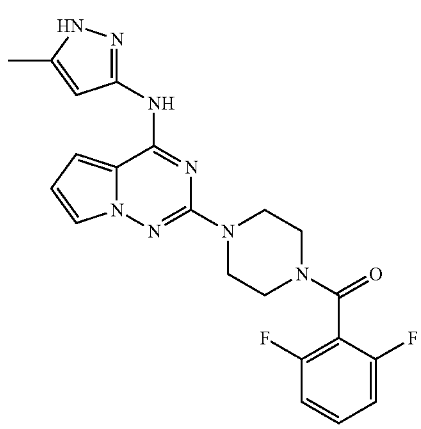 [SMILES: Cc1cc(Nc2nc(N3CCN(C(=O)c4c(F)cccc4F)CC3)nn3cccc23)n[nH]1] | 2-(4-(2,6-difluorobenzoyl)-1-piperazinyl)-N-(5-methyl-1H-pyrazol-3-yl)pyrrolo[2,1-f][1,2,4]triazin-4-amine | 2.32 | 439.15 |

TABLE 1-continued

| Ex. No. | Structure | Name | HPLC Ret. time (min) | m/z [M + H] |
|---|---|---|---|---|
| 21 | 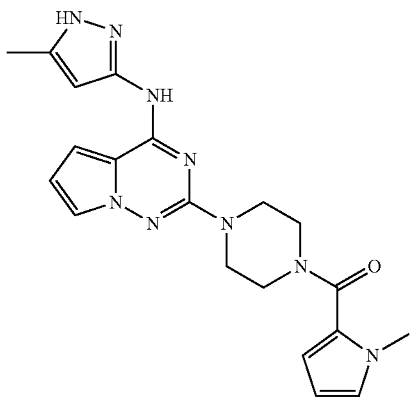 | N-(5-methyl-1H-pyrazol-3-yl)-2-(4-((1-methyl-1H-pyrrol-2-yl)carbonyl)-1-piperazinyl)pyrrolo[2,1-f][1,2,4]triazin-4-amine | 2.24 | 406.19 |
| 22 | 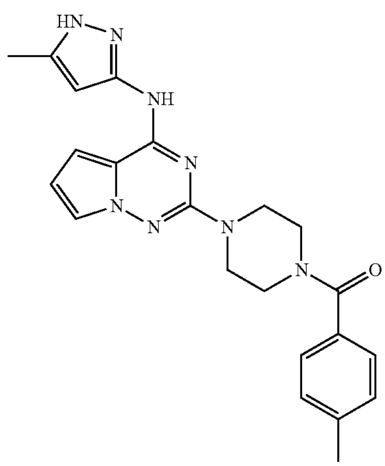 [SMILES: Cc1ccc(C(=O)N2CCN(c3nc(Nc4cc(C)[nH]n4)c4cccn4n3)CC2)cc1] | 2-(4-(4-methylbenzoyl)-1-piperazinyl)-N-(5-methyl-1H-pyrazol-3-yl)pyrrolo[2,1-f][1,2,4]triazin-4-amine | 2.38 | 417.21 |
| 23 | 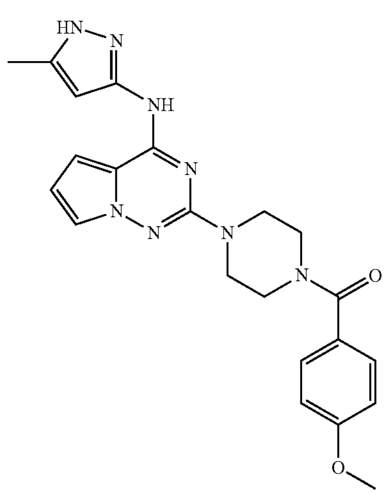 | 2-(4-(4-methoxybenzoyl)-1-piperazinyl)-N-(5-methyl-1H-pyrazol-3-yl)pyrrolo[2,1-f][1,2,4]triazin-4-amine | 2.22 | 433.18 |

TABLE 1-continued

| Ex. No. | Structure | Name | HPLC Ret. time (min) | m/z [M + H] |
|---|---|---|---|---|
| 24 | 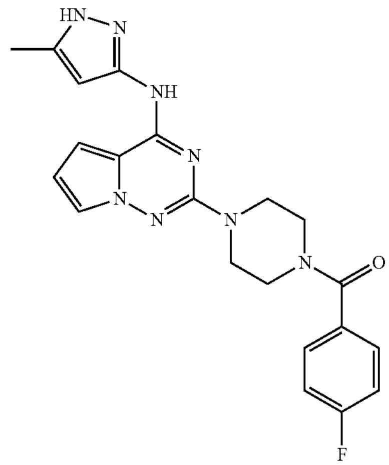 [SMILES: Cc1cc(Nc2nc(N3CCN(C(=O)c4ccc(F)cc4)CC3)nn3cccc23)n[nH]1] | 2-(4-(4-fluorobenzoyl)-1-piperazinyl)-N-(5-methyl-1H-pyrazol-3-yl)pyrrolo[2,1-f][1,2,4]triazin-4-amine | 2.30 | 421.17 |
| 25 | 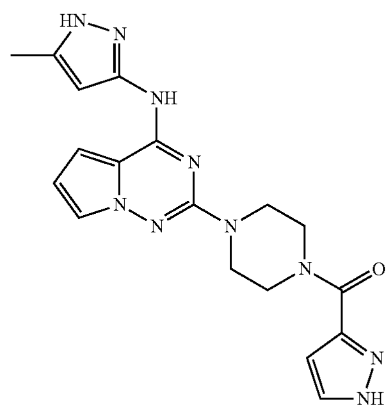 [SMILES: Cc1cc(Nc2nc(N3CCN(C(=O)c4cc[nH]n4)CC3)nn3cccc23)n[nH]1] | N-(5-methyl-1H-pyrazol-3-yl)-2-(4-(1H-pyrazol-3-ylcarbonyl)-1-piperazinyl)pyrrolo[2,1-f][1,2,4]triazin-4-amine | 1.83 | 393.18 |
| 26 | 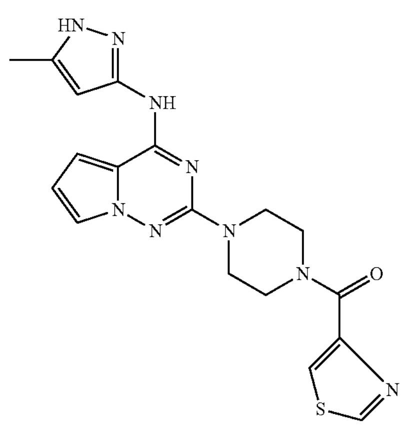 [SMILES: Cc1cc(Nc2nc(N3CCN(C(=O)c4cscn4)CC3)nn3cccc23)n[nH]1] | N-(5-methyl-1H-pyrazol-3-yl)-2-(4-(1,3-thiazol-4-ylcarbonyl)-1-piperazinyl)pyrrolo[2,1-f][1,2,4]triazin-4-amine | 1.96 | 410.13 |

TABLE 1-continued

| Ex. No. | Structure | Name | HPLC Ret. time (min) | m/z [M + H] |
|---|---|---|---|---|
| 27 | 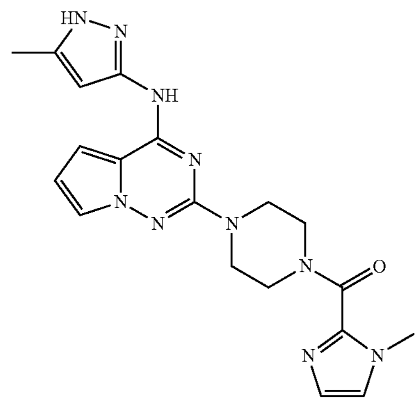 | 2-(4-((1-methyl-1H-imidazol-2-yl)carbonyl)-1-piperazinyl)-N-(5-methyl-1H-pyrazol-3-yl)pyrrolo[2,1-f][1,2,4]triazin-4-amine | 1.88 | 407.18 |
| 28 | 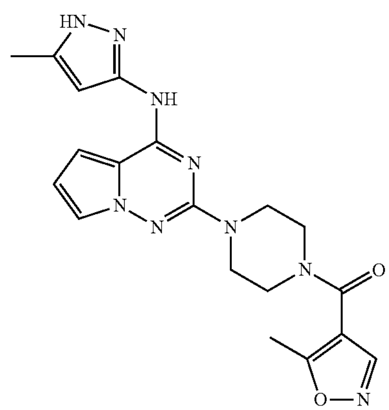 [SMILES: Cc1cc(Nc2nc(N3CCN(C(=O)c4cnoc4C)CC3)nn3cccc23)n[nH]1] | 2-(4-((5-methyl-4-isoxazolyl)carbonyl)-1-piperazinyl)-N-(5-methyl-1H-pyrazol-3-yl)pyrrolo[2,1-f][1,2,4]triazin-4-amine | 2.04 | 408.18 |
| 29 | 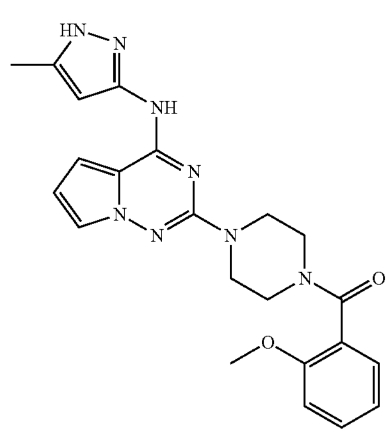 [SMILES: COc1ccccc1C(=O)N1CCN(c2nc(Nc3cc(C)[nH]n3)c3cccn3n2)CC1] | 2-(4-(2-methoxybenzoyl)-1-piperazinyl)-N-(5-methyl-1H-pyrazol-3-yl)pyrrolo[2,1-f][1,2,4]triazin-4-amine | 2.22 | 433.19 |

TABLE 1-continued

| Ex. No. | Structure | Name | HPLC Ret. time (min) | m/z [M + H] |
|---|---|---|---|---|
| 30 | 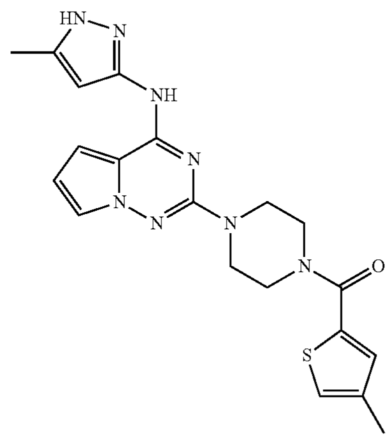 | N-(5-methyl-1H-pyrazol-3-yl)-2-(4-((4-methyl-2-thienyl)carbonyl)-1-piperazinyl)pyrrolo[2,1-f][1,2,4]triazin-4-amine | 2.39 | 423.14 |
| 31 | 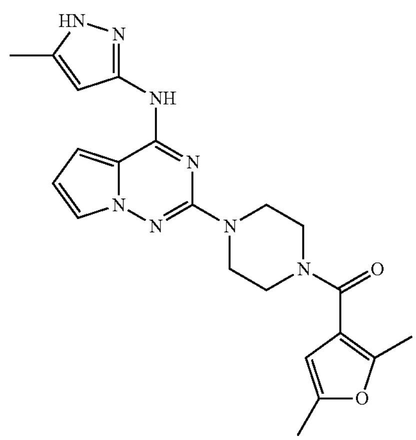 | 2-(4-(2,5-dimethyl-3-furoyl)-1-piperazinyl)-N-(5-methyl-1H-pyrazol-3-yl)pyrrolo[2,1-f][1,2,4]triazin-4-amine | 2.36 | 421.19 |
| 32 | 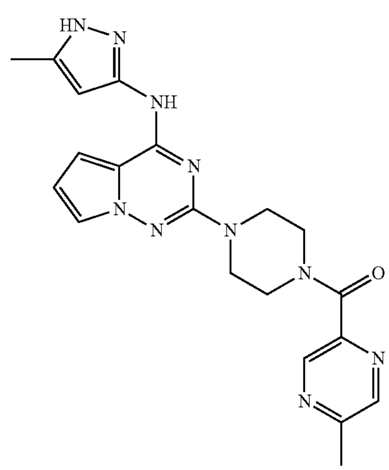 [SMILES: Cc1cnc(C(=O)N2CCN(c3nc(Nc4cc(C)[nH]n4)c4cccn4n3)CC2)cn1] | 2-(4-((5-methyl-2-pyrazinyl)carbonyl)-1-piperazinyl)-N-(5-methyl-1H-pyrazol-3-yl)pyrrolo[2,1-f][1,2,4]triazin-4-amine | 1.92 | 419.20 |

TABLE 1-continued

| Ex. No. | Structure | Name | HPLC Ret. time (min) | m/z [M + H] |
|---|---|---|---|---|
| 33 | 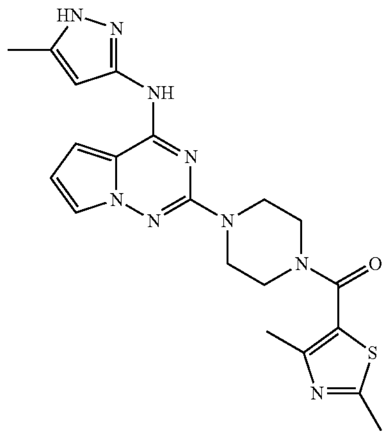 | 2-(4-((2,4-dimethyl-1,3-thiazol-5-yl)carbonyl)-1-piperazinyl)-N-(5-methyl-1H-pyrazol-3-yl)pyrrolo[2,1-f][1,2,4]triazin-4-amine | 1.97 | 438.16 |
| 34 | 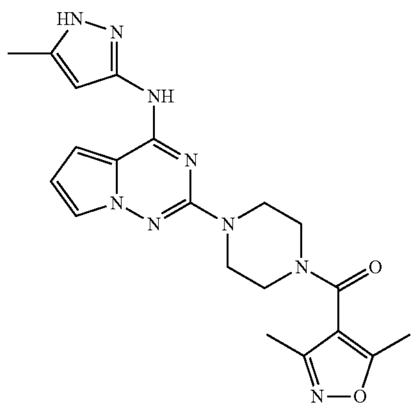 | 2-(4-((3,5-dimethyl-4-isoxazolyl)carbonyl)-1-piperazinyl)-N-(5-methyl-1H-pyrazol-3-yl)pyrrolo[2,1-f][1,2,4]triazin-4-amine | 2.00 | 422.19 |
| 35 | 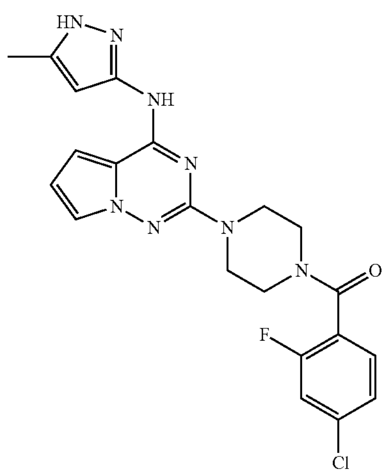 [SMILES: Cc1cc(Nc2nc(N3CCN(C(=O)c4ccc(Cl)cc4F)CC3)nn3cccc23)n[nH]1] | 2-(4-(4-chloro-2-fluorobenzoyl)-1-piperazinyl)-N-(5-methyl-1H-pyrazol-3-yl)pyrrolo[2,1-f][1,2,4]triazin-4-amine | 2.46 | 455.12 |

TABLE 1-continued

| Ex. No. | Structure | Name | HPLC Ret. time (min) | m/z [M + H] |
|---|---|---|---|---|
| 36 | 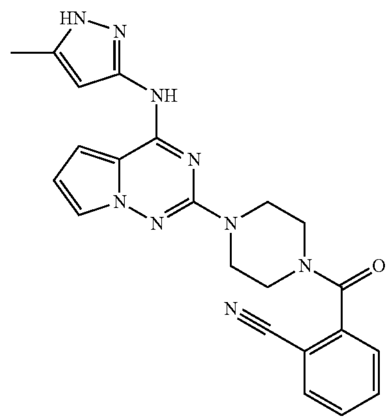 [SMILES: Cc1cc(Nc2nc(N3CCN(C(=O)c4ccccc4C#N)CC3)nn3cccc23)n[nH]1] | 2-((4-(4-((5-methyl-1H-pyrazol-3-yl)amino)pyrrolo[2,1-f][1,2,4]triazin-2-yl)-1-piperazinyl)carbonyl)benzonitrile | 2.11 | 428.18 |
| 37 | 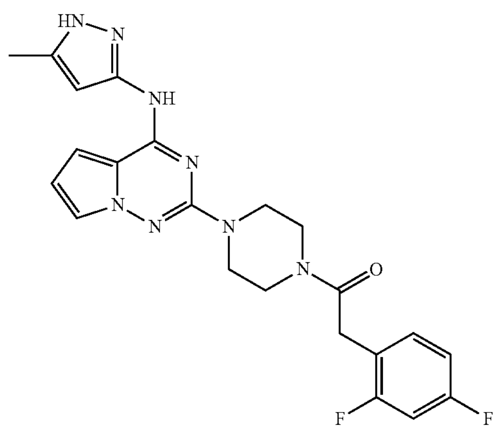 [SMILES: Cc1cc(Nc2nc(N3CCN(C(=O)Cc4ccc(F)cc4F)CC3)nn3cccc23)n[nH]1] | 2-(4-((2,4-difluorophenyl)acetyl)-1-piperazinyl)-N-(5-methyl-1H-pyrazol-3-yl)pyrrolo[2,1-f][1,2,4]triazin-4-amine | 2.35 | 453.16 |
| 38 | 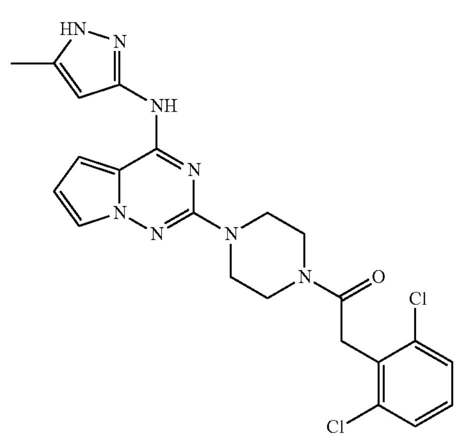 [SMILES: Cc1cc(Nc2nc(N3CCN(C(=O)Cc4c(Cl)cccc4Cl)CC3)nn3cccc23)n[nH]1] | 2-(4-((2,6-dichlorophenyl)acetyl)-1-piperazinyl)-N-(5-methyl-1H-pyrazol-3-yl)pyrrolo[2,1-f][1,2,4]triazin-4-amine | 2.54 | 485.10 |

TABLE 1-continued

| Ex. No. | Structure | Name | HPLC Ret. time (min) | m/z [M + H] |
|---|---|---|---|---|
| 39 | 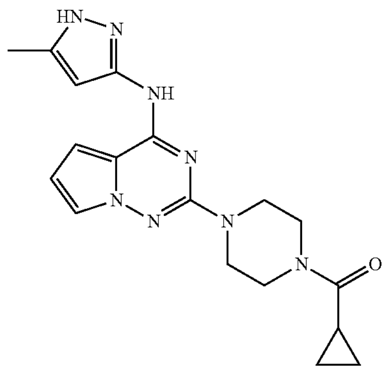 [SMILES: Cc1cc(Nc2nc(N3CCN(C(=O)C4CC4)CC3)nn3cccc23)n[nH]1] | 2-(4-(cyclopropylcarbonyl)-1-piperazinyl)-N-(5-methyl-1H-pyrazol-3-yl)pyrrolo[2,1-f][1,2,4]triazin-4-amine | 1.98 | 367.21 |
| 40 | 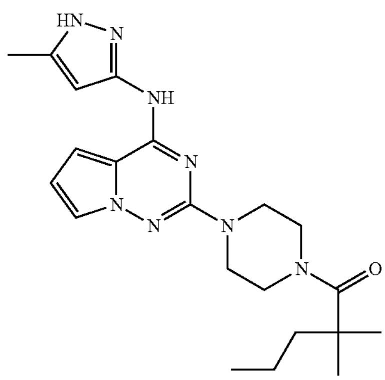 [SMILES: CCCC(C)(C)C(=O)N1CCN(c2nc(Nc3cc(C)[nH]n3)c3cccn3n2)CC1] | 2-(4-(2,2-dimethylpentanoyl)-1-piperazinyl)-N-(5-methyl-1H-pyrazol-3-yl)pyrrolo[2,1-f][1,2,4]triazin-4-amine | 2.51 | 411.25 |
| 41 | 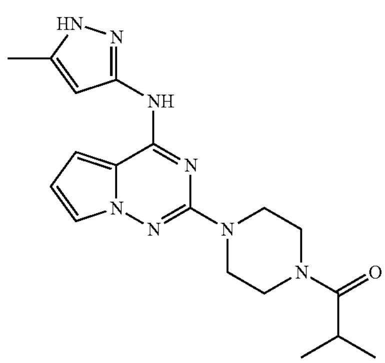 [SMILES: Cc1cc(Nc2nc(N3CCN(C(=O)C(C)C)CC3)nn3cccc23)n[nH]1] | 2-(4-isobutyryl-1-piperazinyl)-N-(5-methyl-1H-pyrazol-3-yl)pyrrolo[2,1-f][1,2,4]triazin-4-amine | 2.04 | 369.21 |
| 42 | 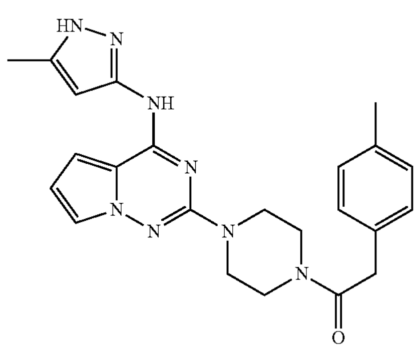 [SMILES: Cc1ccc(CC(=O)N2CCN(c3nc(Nc4cc(C)[nH]n4)c4cccn4n3)CC2)cc1] | 2-(4-((4-methylphenyl)acetyl)-1-piperazinyl)-N-(5-methyl-1H-pyrazol-3-yl)pyrrolo[2,1-f][1,2,4]triazin-4-amine | 2.28 | 431.42 |

TABLE 1-continued

| Ex. No. | Structure | Name | HPLC Ret. time (min) | m/z [M + H] |
|---|---|---|---|---|
| 43 | 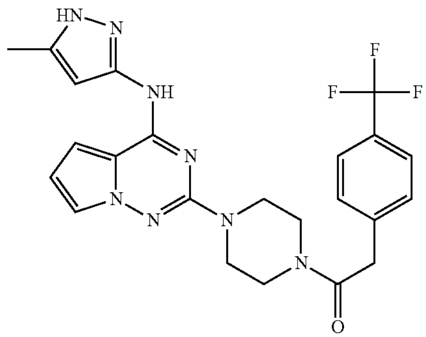 [SMILES: Cc1cc(Nc2nc(N3CCN(C(=O)Cc4ccc(C(F)(F)F)cc4)CC3)nn3cccc23)n[nH]1] | N-(5-methyl-1H-pyrazol-3-yl)-2-(4-((4-(trifluoromethyl)phenyl)acetyl)-1-piperazinyl)pyrrolo[2,1-f][1,2,4]triazin-4-amine | 2.48 | 485.41 |
| 44 | 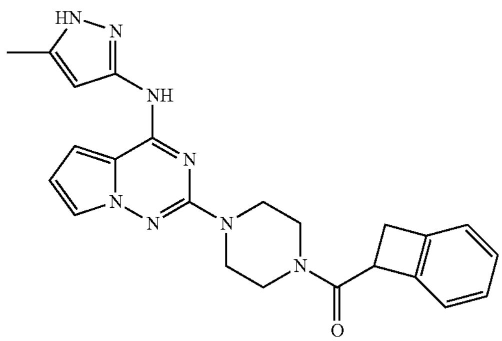 [SMILES: Cc1cc(Nc2nc(N3CCN(C(=O)C4Cc5ccccc54)CC3)nn3cccc23)n[nH]1] | 2-(4-(bicyclo[4.2.0]octa-1,3,5-trien-7-ylcarbonyl)-1-piperazinyl)-N-(5-methyl-1H-pyrazol-3-yl)pyrrolo[2,1-f][1,2,4]triazin-4-amine | 2.30 | 429.42 |
| 45 | 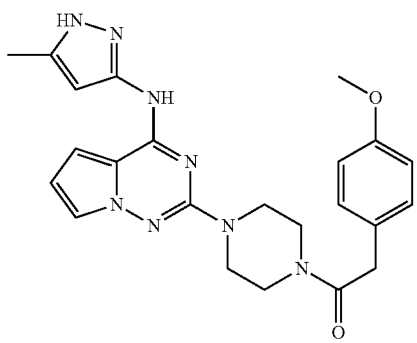 [SMILES: COc1ccc(CC(=O)N2CCN(c3nc(Nc4cc(C)[nH]n4)c4cccn4n3)CC2)cc1] | 2-(4-((4-methoxyphenyl)acetyl)-1-piperazinyl)-N-(5-methyl-1H-pyrazol-3-yl)pyrrolo[2,1-f][1,2,4]triazin-4-amine | 2.12 | 447.43 |
| 46 | 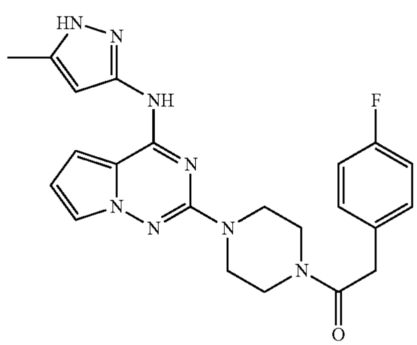 [SMILES: Cc1cc(Nc2nc(N3CCN(C(=O)Cc4ccc(F)cc4)CC3)nn3cccc23)n[nH]1] | 2-(4-((4-fluorophenyl(acetyl)-1-piperazinyl)-N-(5-methyl-1H-pyrazol-3-yl)pyrrolo[2,1-f][1,2,4]triazin-4-amine | 2.18 | 435.42 |

TABLE 1-continued

| Ex. No. | Structure | Name | HPLC Ret. time (min) | m/z [M + H] |
|---|---|---|---|---|
| 47 | 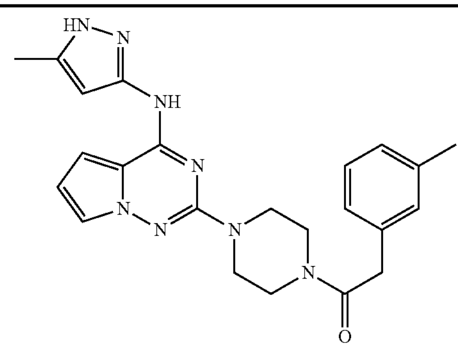 | 2-(4-((3-methylphenyl)acetyl)-1-piperazinyl)-N-(5-methyl-1H-pyrazol-3-yl)pyrrolo[2,1-f][1,2,4]triazin-4-amine | 2.30 | 431.43 |
| 48 | 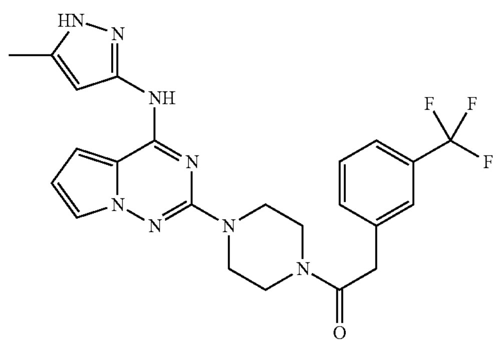 [SMILES: Cc1cc(Nc2nc(N3CCN(C(=O)Cc4cccc(C(F)(F)F)c4)CC3)nn3cccc23)n[nH]1] | N-(5-methyl-1H-pyrazol-3-yl)-2-(4-((3-(trifluoromethyl)phenyl)acetyl)-1-piperazinyl)pyrrolo[2,1-f][1,2,4]triazin-4-amine | 2.46 | 485.42 |
| 49 | 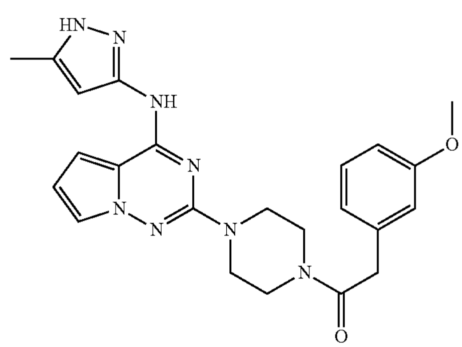 | 2-(4-((3-methoxyphenyl)acetyl)-1-piperazinyl)-N-(5-methyl-1H-pyrazol-3-yl)pyrrolo[2,1-f][1,2,4]triazin-4-amine | 2.13 | 447.44 |
| 50 | 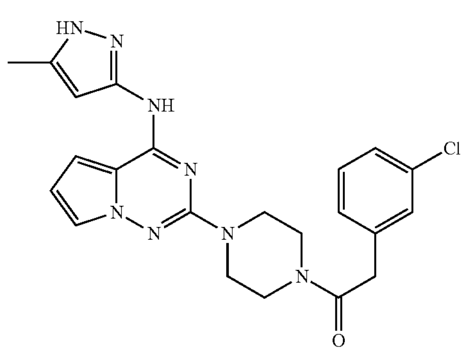 [SMILES: Cc1cc(Nc2nc(N3CCN(C(=O)Cc4cccc(Cl)c4)CC3)nn3cccc23)n[nH]1] | 2-(4-((3-chlorophenyl)acetyl)-1-piperazinyl)-N-(5-methyl-1H-pyrazol-3-yl)pyrrolo[2,1-f][1,2,4]triazin-4-amine | 2.34 | 451.39 |

TABLE 1-continued

| Ex. No. | Structure | Name | HPLC Ret. time (min) | m/z [M + H] |
|---|---|---|---|---|
| 51 | 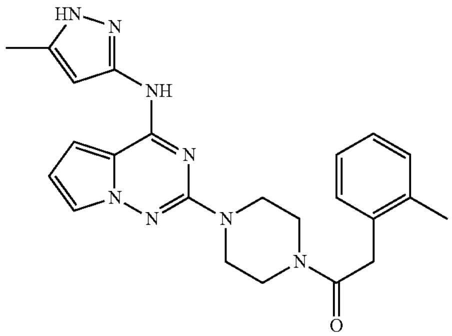 | 2-(4-((2-methylphenyl)acetyl)-1-piperazinyl)-N-(5-methyl-1H-pyrazol-3-yl)pyrrolo[2,1-f][1,2,4]triazin-4-amine | 2.29 | 431.43 |
| 52 | 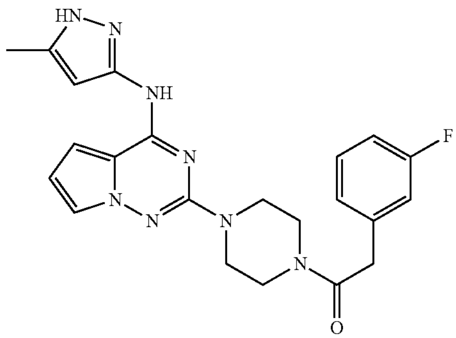 [SMILES: Cc1cc(Nc2nc(N3CCN(C(=O)Cc4cccc(F)c4)CC3)nn3cccc23)n[nH]1] | 2-(4-((3-fluorophenyl)acetyl)-l-piperazinyl)-N-(5-methyl-1H-pyrazol-3-yl)pyrrolo[2,1-f][1,2,4]triazin-4-amine | 2.20 | 435.42 |
| 53 | 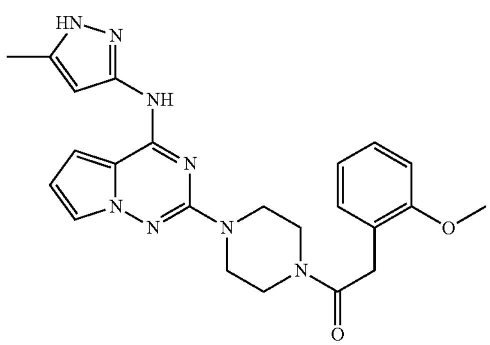 | 2-(4-((2-methoxyphenyl)acetyl)-1-piperazinyl)-N-(5-methyl-1H-pyrazol-3-yl)pyrrolo[2,1-f][1,2,4]triazin-4-amine | 2.18 | 447.43 |
| 54 | 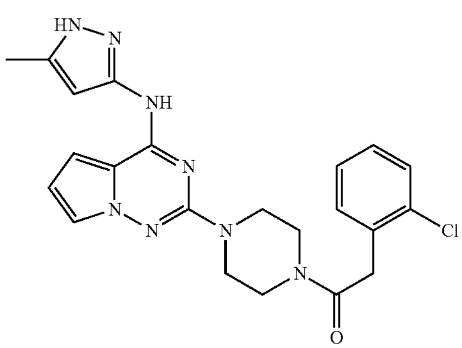 [SMILES: Cc1cc(Nc2nc(N3CCN(C(=O)Cc4ccccc4Cl)CC3)nn3cccc23)n[nH]1] | 2-(4-((2-chlorophenyl)acetyl)-1-piperazinyl)-N-(5-methyl-1H-pyrazol-3-yl)pyrrolo[2,1-f][1,2,4]triazin-4-amine | 2.34 | 451.39 |

TABLE 1-continued

| Ex. No. | Structure | Name | HPLC Ret. time (min) | m/z [M + H] |
|---|---|---|---|---|
| 55 | 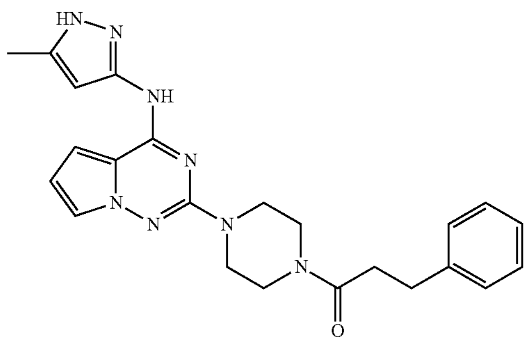 [SMILES: Cc1cc(Nc2nc(N3CCN(C(=O)CCc4ccccc4)CC3)nn3cccc23)n[nH]1] | N-(5-methyl-1H-pyrazol-3-yl)-2-(4-(3-phenylpropanoyl)-1-piperazinyl)pyrrolo[2,1-f][1,2,4]triazin-4-amine | 2.28 | 431.44 |
| 56 | 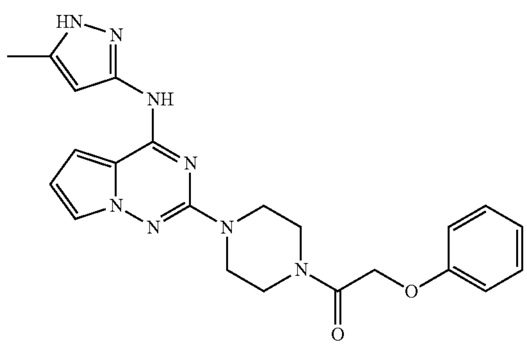 [SMILES: Cc1cc(Nc2nc(N3CCN(C(=O)COc4ccccc4)CC3)nn3cccc23)n[nH]1] | N-(5-methyl-1H-pyrazol-3-yl)-2-(4-(phenoxyacetyl)-1-piperazinyl)pyrrolo[2,1-f][1,2,4]triazin-4-amine | 2.18 | 433.42 |
| 57 | 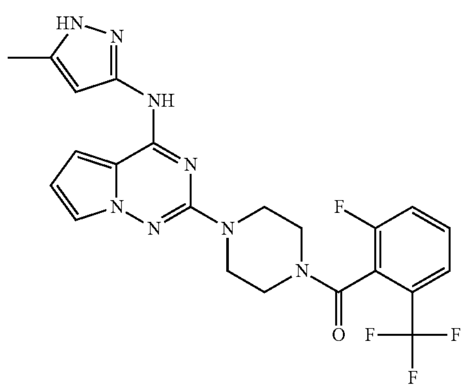 [SMILES: Cc1cc(Nc2nc(N3CCN(C(=O)c4c(F)cccc4C(F)(F)F)CC3)nn3cccc23)n[nH]1] | 2-(4-(2-fluoro-6-(trifluoromethyl)benzoyl)-1-piperazinyl)-N-(5-methyl-1H-pyrazol-3-yl)pyrrolo[2,1-f][1,2,4]triazin-4-amine | 2.34 | 489.40 |
| 58 | 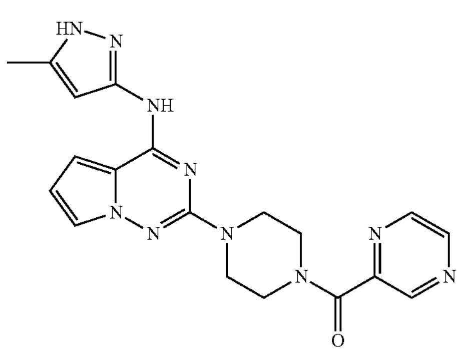 [SMILES: Cc1cc(Nc2nc(N3CCN(C(=O)c4cnccn4)CC3)nn3cccc23)n[nH]1] | N-(5-methyl-1H-pyrazol-3-yl])-2-(4-(2-pyrazinylcarbonyl)-1-piperazinyl)pyrrolo[2,1-f][1,2,4]triazin-4-amine | 1.68 | 405.39 |

TABLE 1-continued

| Ex. No. | Structure | Name | HPLC Ret. time (min) | m/z [M + H] |
|---|---|---|---|---|
| 59 | 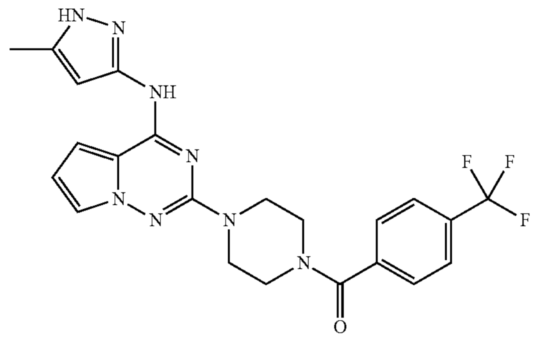 [SMILES: Cc1cc(Nc2nc(N3CCN(C(=O)c4ccc(C(F)(F)F)cc4)CC3)nn3cccc23)n[nH]1] | N-(5-methyl-1H-pyrazol-3-yl)-2-(4-(4-(trifluoromethyl)benzoyl)-1-piperazinyl)pyrrolo[2,1-f][1,2,4]triazin-4-amine | 2.44 | 471.41 |
| 60 | 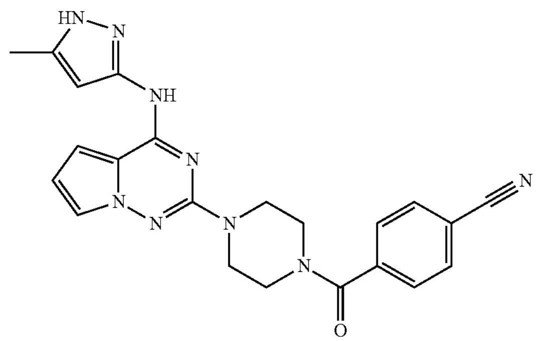 [SMILES: Cc1cc(Nc2nc(N3CCN(C(=O)c4ccc(C#N)cc4)CC3)nn3cccc23)n[nH]1] | 4-((4-(4-((5-methyl-1H-pyrazol-3-yl)amino)pyrrolo[2,1-f][1,2,4]triazin-2-yl)-1-piperazinyl)carbonyl)benzonitrile | 2.02 | 428.41 |
| 61 | 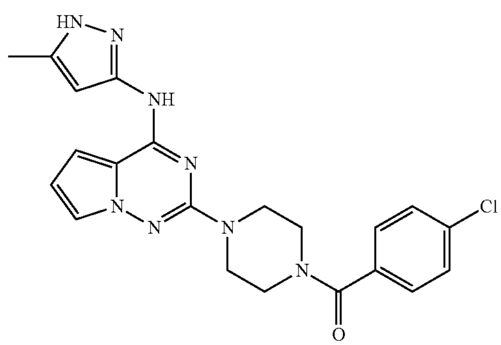 [SMILES: Cc1cc(Nc2nc(N3CCN(C(=O)c4ccc(Cl)cc4)CC3)nn3cccc23)n[nH]1] | 2-(4-(4-chlorobenzoyl)-1-piperazinyl)-N-(5-methyl-1H-pyrazol-3-yl)pyrrolo[2,1-f][1,2,4]triazin-4-amine | 2.33 | 437.38 |
| 62 | 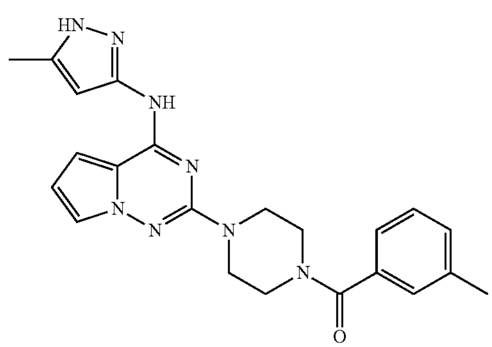 | 2-(4-(3-methylbenzoyl)-1-piperazinyl)-N-(5-methyl-1H-pyrazol-3-yl)pyrrolo[2,1-f][1,2,4]triazin-4-amine | 2.23 | 417.42 |

TABLE 1-continued

| Ex. No. | Structure | Name | HPLC Ret. time (min) | m/z [M + H] |
|---|---|---|---|---|
| 63 | 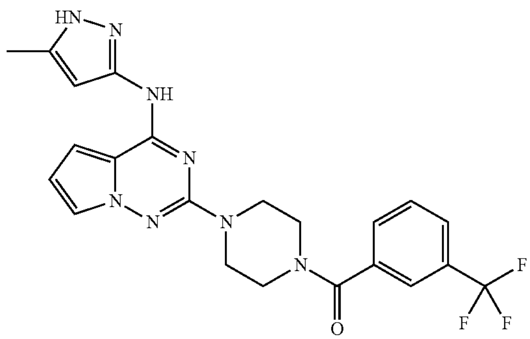 [SMILES: Cc1cc(Nc2nc(N3CCN(C(=O)c4cccc(C(F)(F)F)c4)CC3)nn3cccc23)n[nH]1] | N-(5-methyl-1H-pyrazol-3-yl)-2-(4-(3-(trifluoromethyl)benzoyl)-1-piperazinyl)pyrrolo[2,1-f][1,2,4]triazin-4-amine | 2.42 | 471.42 |
| 64 | 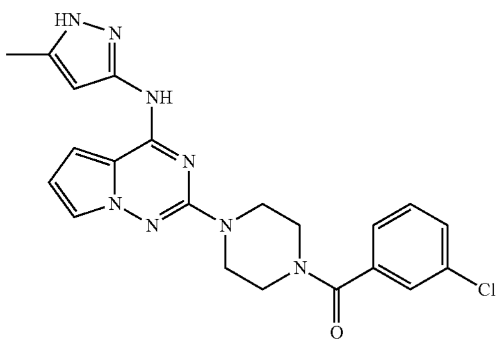 [SMILES: Cc1cc(Nc2nc(N3CCN(C(=O)c4cccc(Cl)c4)CC3)nn3cccc23)n[nH]1] | 2-(4-(3-chlorobenzoyl)-1-piperazinyl)-N-(5-methyl-1H-pyrazol-3-yl)pyrrolo[2,1-f][1,2,4]triazin-4-amine | 2.30 | 437.38 |
| 65 | 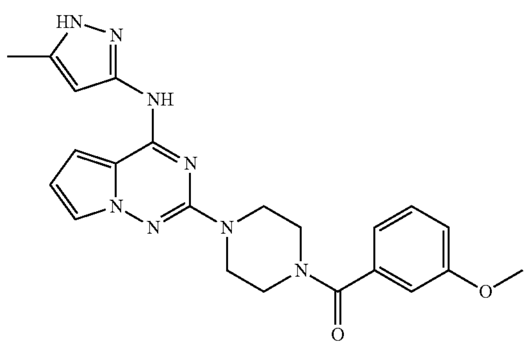 | 2-(4-(3-methoxybenzoyl)-1-piperazinyl)-N-(5-methyl-1H-pyrazol-3-yl)pyrrolo[2,1-f][1,2,4]triazin-4-amine | 2.13 | 433.42 |
| 66 | 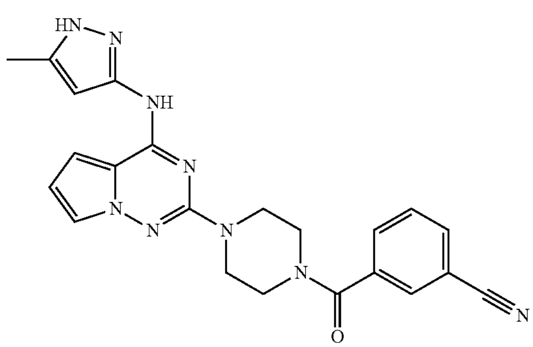 [SMILES: Cc1cc(Nc2nc(N3CCN(C(=O)c4cccc(C#N)c4)CC3)nn3cccc23)n[nH]1] | 3-((4-(4-((5-methyl-1H-pyrazol-3-yl)amino)pyrrolo[2,1-f][1,2,4]triazin-2-yl)-1-piperazinyl)carbonyl)benzonitrile | 2.02 | 428.42 |

TABLE 1-continued

| Ex. No. | Structure | Name | HPLC Ret. time (min) | m/z [M + H] |
|---|---|---|---|---|
| 67 | 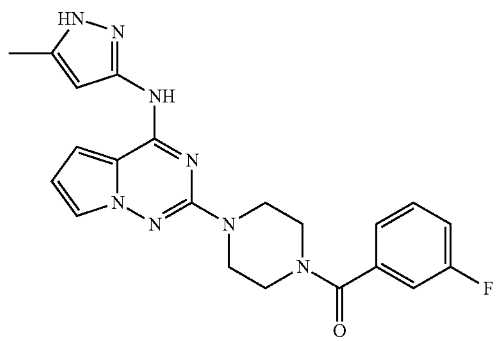 [SMILES: Cc1cc(Nc2nc(N3CCN(C(=O)c4cccc(F)c4)CC3)nn3cccc23)n[nH]1] | 2-(4-(3-fluorobenzoyl)-1-piperazinyl)-N-(5-methyl-1H-pyrazol-3-yl)pyrrolo[2,1-f][1,2,4]triazin-4-amine | 2.15 | 421.40 |
| 68 | 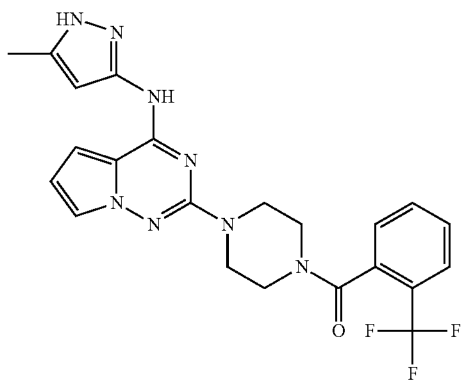 [SMILES: Cc1cc(Nc2nc(N3CCN(C(=O)c4ccccc4C(F)(F)F)CC3)nn3cccc23)n[nH]1] | N-(5-methyl-1H-pyrazol-3-yl)-2-(4-(2-(trifluoromethyl(benzoyl)-1-piperazinyl)pyrrolo[2,1-f][1,2,4]triazin-4-amine | 2.32 | 471.41 |
| 69 | 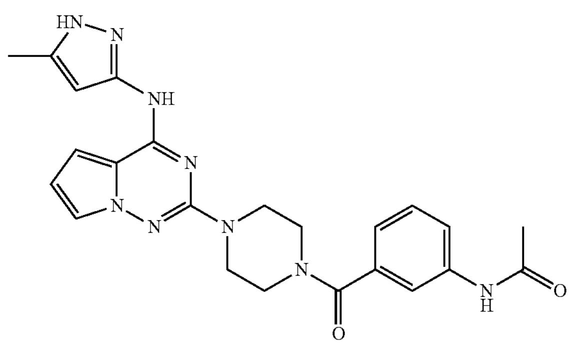 [SMILES: CC(=O)Nc1cccc(C(=O)N2CCN(c3nc(Nc4cc(C)[nH]n4)c4cccn4n3)CC2)c1] | N-(3-((4-(4-((5-methyl-1H-pyrazol-3-yl)amino)pyrrolo[2,1-f][1,2,4]triazin-2-yl)-1-piperazinyl)carbonyl)phenyl)acetamide | 1.77 | 460.45 |
| 70 | 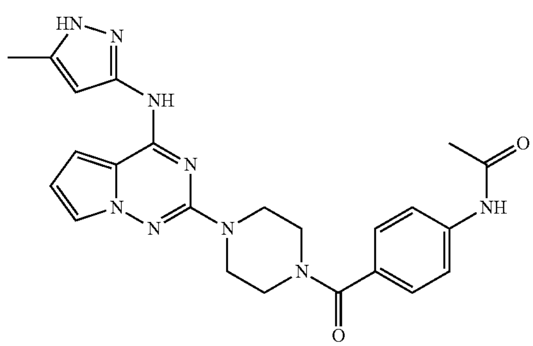 [SMILES: CC(=O)Nc1ccc(C(=O)N2CCN(c3nc(Nc4cc(C)[nH]n4)c4cccn4n3)CC2)cc1] | N-(4-((4-(4-((5-methyl-1H-pyrazol-3-yl)amino)pyrrolo[2,1-f][1,2,4]triazin-2-yl)-1-piperazinyl)carbonyl)phenyl)acetamide | 1.73 | 460.46 |

TABLE 1-continued

| Ex. No. | Structure | Name | HPLC Ret. time (min) | m/z [M + H] |
|---|---|---|---|---|
| 71 | 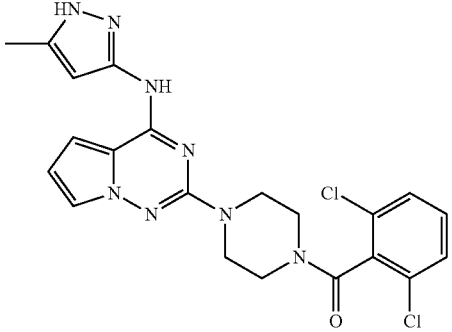 [SMILES: Cc1cc(Nc2nc(N3CCN(C(=O)c4c(Cl)cccc4Cl)CC3)nn3cccc23)n[nH]1] | 2-(4-(2,6-dichlorobenzoyl)-1-piperazinyl)-N-(5-methyl-1H-pyrazol-3-yl)pyrrolo[2,1-f][1,2,4]triazin-4-amine | 2.32 | 471.37 |
| 72 | 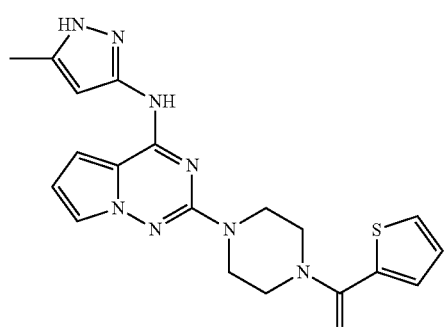 | N-(5-methyl-1H-pyrazol-3-yl)-2-(4-(2-thienylcarbonyl)-1-piperazinyl)pyrrolo[2,1-f][1,2,4]triazin-4-amine | 2.08 | 409.38 |
| 73 | 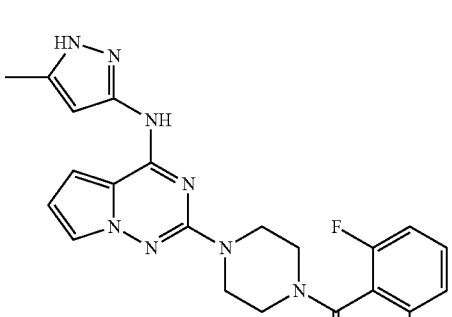 | 2-(4-(2-chloro-6-fluorobenzoyl)-1-piperazinyl)-N-(5-methyl-1H-pyrazol-3-yl)pyrrolo[2,1-f][1,2,4]triazin-4-amine | 2.26 | 455.39 |
| 74 | 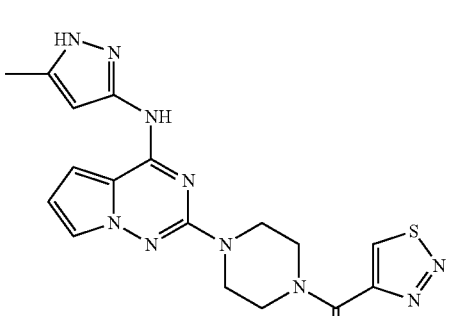 | N-(5-methyl-1H-pyrazol-3-yl)-2-(4-(1,2,3-thiadiazol-4-ylcarbonyl)-1-piperazinyl)pyrrolo[2,1-f][1,2,4]triazin-4-amine | 1.82 | 411.37 |

TABLE 1-continued

| Ex. No. | Structure | Name | HPLC Ret. time (min) | m/z [M + H] |
|---|---|---|---|---|
| 75 | 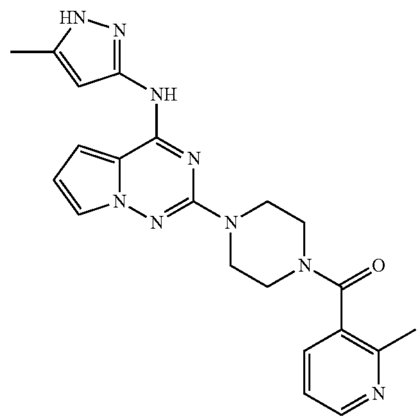 | N-(5-methyl-1H-pyrazol-3-yl)-2-(4-((2-methyl-3-pyridinyl)carbonyl)-1-piperazinyl)pyrrolo[2,1-f][1,2,4]triazin-4-amine | 2.12 | 418.21 |
| 76 | 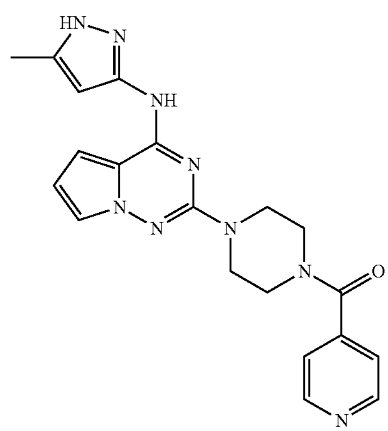 [SMILES: Cc1cc(Nc2nc(N3CCN(C(=O)c4ccncc4)CC3)nn3cccc23)n[nH]1] | 2-(4-isonicotinoyl-1-piperazinyl)-N-(5-methyl-1H-pyrazol-3-yl)pyrrolo[2,1-f][1,2,4]triazin-4-amine | 2.16 | 404.20 |
| 77 | 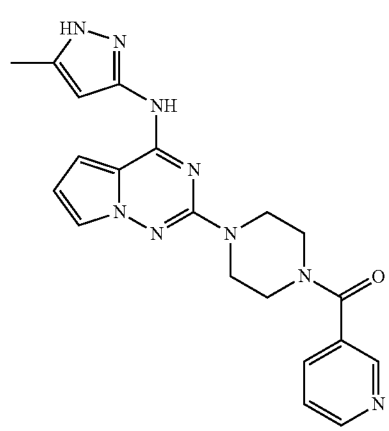 [SMILES: Cc1cc(Nc2nc(N3CCN(C(=O)c4cccnc4)CC3)nn3cccc23)n[nH]1] | N-(5-methyl-1H-pyrazol-3-yl)-2-(4-(3-pyridinylcarbonyl)-1-piperazinyl)pyrrolo[2,1-f][1,2,4]triazin-4-amine | 2.34 | 404.19 |

TABLE 1-continued

| Ex. No. | Structure | Name | HPLC Ret. time (min) | m/z [M + H] |
| --- | --- | --- | --- | --- |
| 78 | 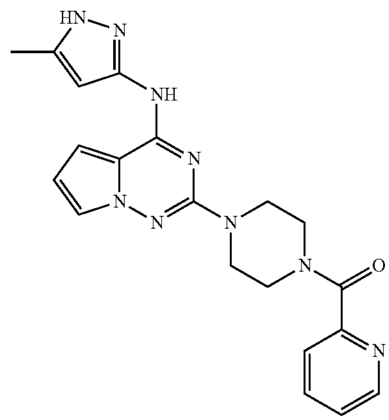 [SMILES: Cc1cc(Nc2nc(N3CCN(C(=O)c4ccccn4)CC3)nn3cccc23)n[nH]1] | N-(5-methyl-1H-pyrazol-3-yl)-2-(4-(2-pyridinylcarbonyl)-1-piperazinyl)pyrrolo[2,1-f][1,2,4]triazin-4-amine | 2.59 | 404.21 |
| 79 | 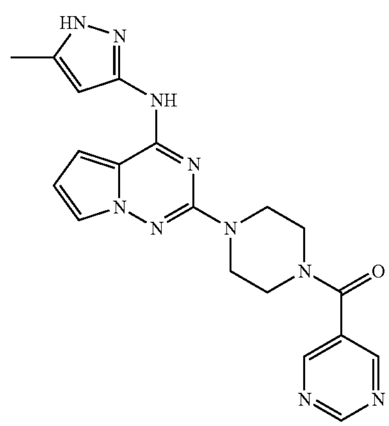 [SMILES: Cc1cc(Nc2nc(N3CCN(C(=O)c4cncnc4)CC3)nn3cccc23)n[nH]1] | N-(5-methyl-1H-pyrazol-3-yl)-2-(4-(5-pyrimidinylcarbonyl)-1-piperazinyl)pyrrolo[2,1-f][1,2,4]triazin-4-amine | 2.44 | 405.20 |
| 80 | 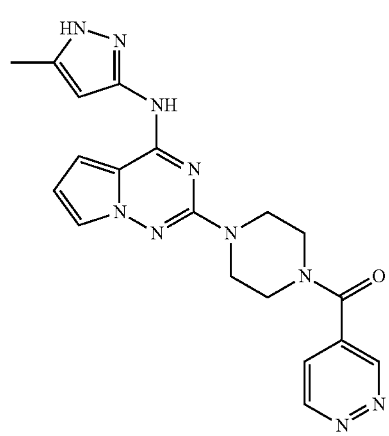 [SMILES: Cc1cc(Nc2nc(N3CCN(C(=O)c4ccnnc4)CC3)nn3cccc23)n[nH]1] | N-(5-methyl-1H-pyrazol-3-yl)-2-(4-(4-pyridazinylcarbonyl)-1-piperazinyl)pyrrolo[2,1-f][1,2,4]triazin-4-amine | 2.30 | 405.20 |

TABLE 1-continued

| Ex. No. | Structure | Name | HPLC Ret. time (min) | m/z [M + H] |
|---|---|---|---|---|
| 81 | 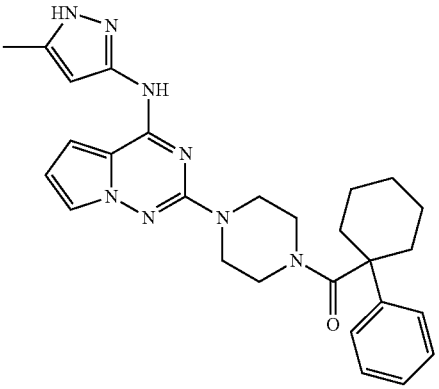 [SMILES: Cc1cc(Nc2nc(N3CCN(C(=O)C4(c5ccccc5)CCCCC4)CC3)nn3cccc23)n[nH]1] | N-(5-methyl-1H-pyrazol-3-yl)-2-(4-((1-phenylcyclohexyl)carbonyl)-1-piperazinyl)pyrrolo[2,1-f][1,2,4]triazin-4-amine | 2.84 | 485.02 |
| 82 | 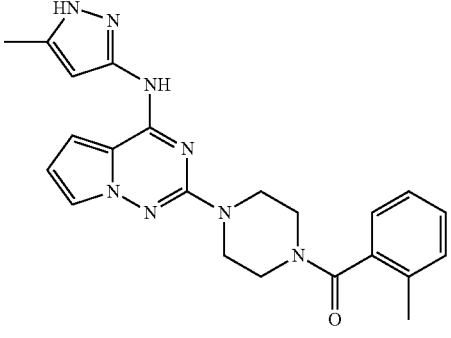 [SMILES: Cc1cc(Nc2nc(N3CCN(C(=O)c4ccccc4C)CC3)nn3cccc23)n[nH]1] | 2-(4-(2-methylbenzoyl)-1-piperazinyl)-N-(5-methyl-1H-pyrazol-3-yl)pyrrolo[2,1-f][1,2,4]triazin-4-amine | 2.01 | 417.01 |
| 83 | 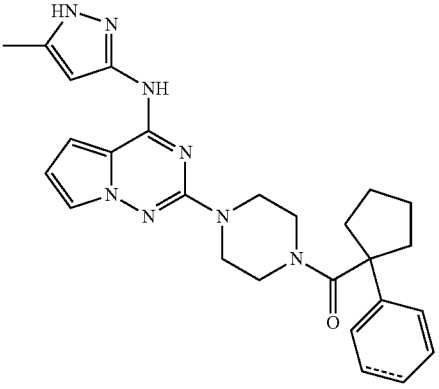 | N-(5-methyl-1H-pyrazol-3-yl)-2-(4-((1-phenylcyclopentyl)carbonyl)-1-piperazinyl)pyrrolo[2,1-f][1,2,4]triazin-4-amine | 2.61 | 471.03 |
| 84 | 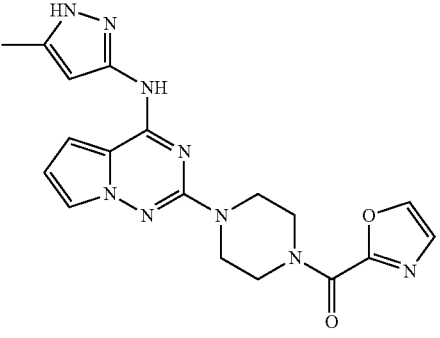 [SMILES: Cc1cc(Nc2nc(N3CCN(C(=O)c4ncco4)CC3)nn3cccc23)n[nH]1] | N-(5-methyl-1H-pyrazol-3-yl)-2-(4-(1,3-oxazol-2-ylcarbonyl)-1-piperazinyl)pyrrolo[2,1-f][1,2,4]triazin-4-amine | 1.64 | 393.96 |

TABLE 1-continued

| Ex. No. | Structure | Name | HPLC Ret. time (min) | m/z [M + H] |
|---|---|---|---|---|
| 85 | 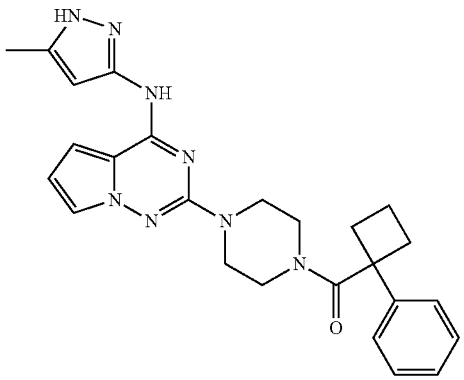 [SMILES: Cc1cc(Nc2nc(N3CCN(C(=O)C4(c5ccccc5)CCC4)CC3)nn3cccc23)n[nH]1] | N-(5-methyl-1H-pyrazol-3-yl)-2-(4-((1-phenylcyclobutyl)carbonyl)-1-piperazinyl)pyrrolo[2,1-f][1,2,4]triazin-4-amine | 2.40 | 457.01 |
| 86 | 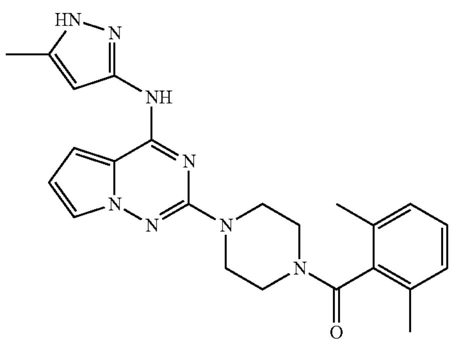 [SMILES: Cc1cc(Nc2nc(N3CCN(C(=O)c4c(C)cccc4C)CC3)nn3cccc23)n[nH]1] | 2-(4-(2,6-dimethylbenzoyl)-1-piperazinyl)-N-(5-methyl-1H-pyrazol-3-yl)pyrrolo[2,1-f][1,2,4]triazin-4-amine | 2.10 | 431.01 |
| 87 | 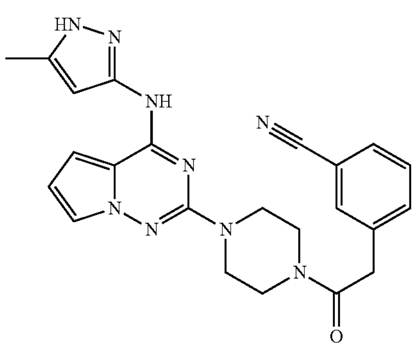 [SMILES: Cc1cc(Nc2nc(N3CCN(C(=O)Cc4cccc(C#N)c4)CC3)nn3cccc23)n[nH]1] | 3-(2-(4-(4-((5-methyl-1H-pyrazol-3-yl)amino)pyrrolo[2,1-f][1,2,4]triazin-2-yl)-1-piperazinyl)-2-oxoethyl)benzonitrile | 1.91 | 441..99 |
| 88 | 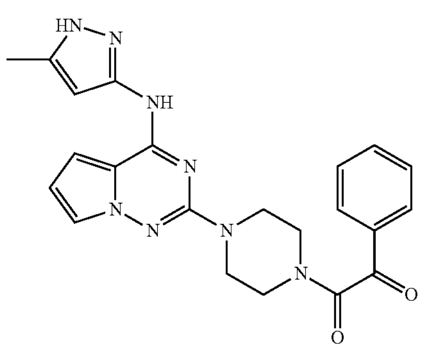 [SMILES: Cc1cc(Nc2nc(N3CCN(C(=O)C(=O)c4ccccc4)CC3)nn3cccc23)n[nH]1] | 2-(4-(4-((5-methyl-1H-pyrazol-3-yl)amino)pyrrolo[2,1-f][1,2,4]triazin-2-yl)-1-piperazinyl)-2-oxo-1-phenylethanone | 2.10 | 430.97 |

TABLE 1-continued

| Ex. No. | Structure | Name | HPLC Ret. time (min) | m/z [M + H] |
|---|---|---|---|---|
| 89 | 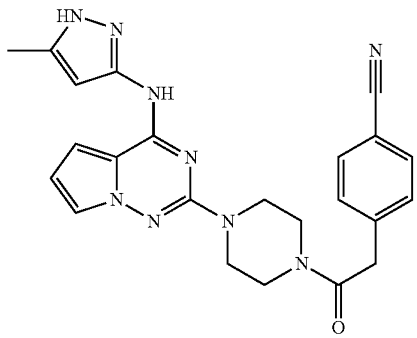 [SMILES: Cc1cc(Nc2nc(N3CCN(C(=O)Cc4ccc(C#N)cc4)CC3)nn3cccc23)n[nH]1] | 4-(2-(4-(4-((5-methyl-1H-pyrazol-3-yl)amino)pyrrolo[2,1-f][1,2,4]triazin-2-yl)-1-piperazinyl)-2-oxoethyl)benzonitrile | 1.90 | 441.96 |
| 90 | 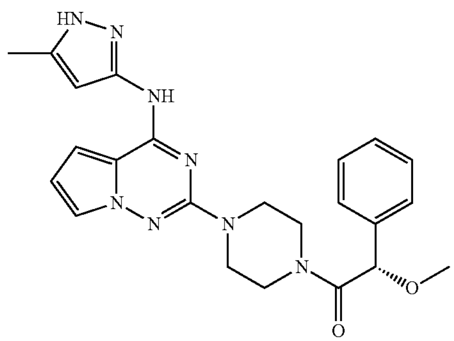 | 2-(4-((2S)-2-methoxy-2-phenylacetyl)-1-piperazinyl)-N-(5-methyl-1H-pyrazol-3-yl)pyrrolo[2,1-f][1,2,4]triazin-4-amine | 1.94 | 446.99 |
| 91 | 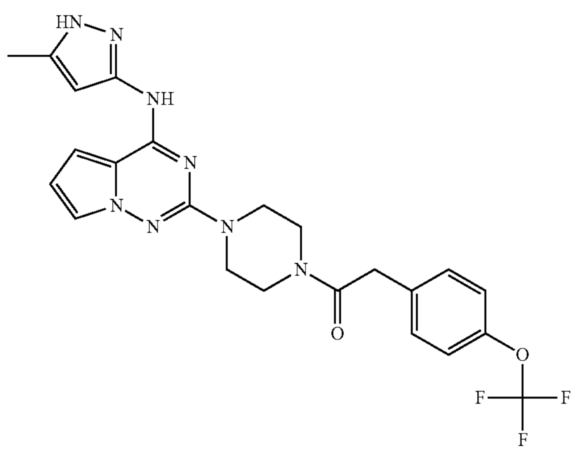 [SMILES: Cc1cc(Nc2nc(N3CCN(C(=O)Cc4ccc(OC(F)(F)F)cc4)CC3)nn3cccc23)n[nH]1] | N-(5-methyl-1H-pyrazol-3-yl)-2-(4-((4-(trifluoromethoxy)phenyl)acetyl)-1-piperazinyl)pyrrolo[2,1-f][1,2,4]triazin-4-amine | 2.39 | 500.94 |
| 92 | 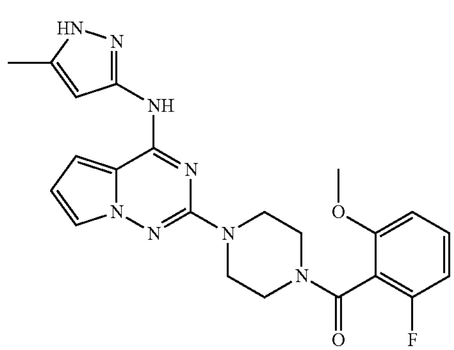 [SMILES: COc1cccc(F)c1C(=O)N1CCN(c2nc(Nc3cc(C)[nH]n3)c3cccn3n2)CC1] | 2-(4-(2-fluoro-6-methoxybenzoyl)-1-piperazinyl)-N-(5-methyl-1H-pyrazol-3-yl)pyrrolo[2,1-f][1,2,4]triazin-4-amine | 1.96 | 450.97 |

TABLE 1-continued

| Ex. No. | Structure | Name | HPLC Ret. time (min) | m/z [M + H] |
|---|---|---|---|---|
| 93 | 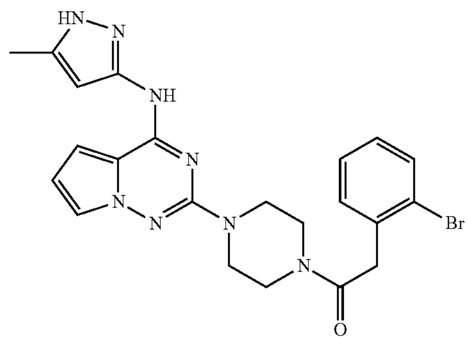 [SMILES: Cc1cc(Nc2nc(N3CCN(C(=O)Cc4ccccc4Br)CC3)nn3cccc23)n[nH]1] | 2-(4-((2-bromophenyl)acetyl)-1-piperazinyl)-N-(5-methyl-1H-pyrazol-3-yl)pyrrolo[2,1-f][1,2,4]triazin-4-amine | 2.24 | 494.87 |
| 94 | 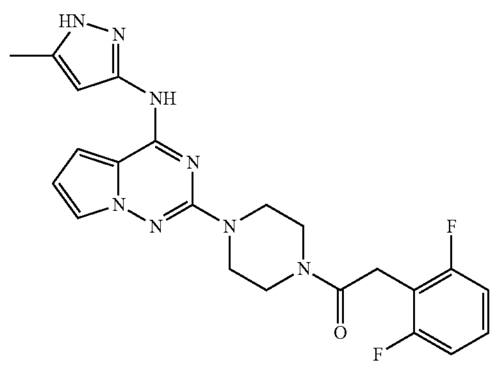 [SMILES: Cc1cc(Nc2nc(N3CCN(C(=O)Cc4c(F)cccc4F)CC3)nn3cccc23)n[nH]1] | 2-(4-((2,6-difluorophenyl)acetyl)-1-piperazinyl)-N-(5-methyl-1H-pyrazol-3-yl)pyrrolo[2,1-f][1,2,4]triazin-4-amine | 2.12 | 452.96 |
| 95 | 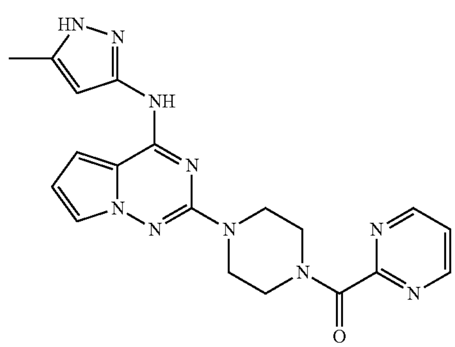 [SMILES: Cc1cc(Nc2nc(N3CCN(C(=O)c4ncccn4)CC3)nn3cccc23)n[nH]1] | N-(5-methyl-1H-pyrazol-3-yl)-2-(4-(2-pyrimidinylcarbonyl)-1-piperazinyl)pyrrolo[2,1-f][1,2,4]triazin-4-amine | 1.41 | 404.98 |
| 96 | 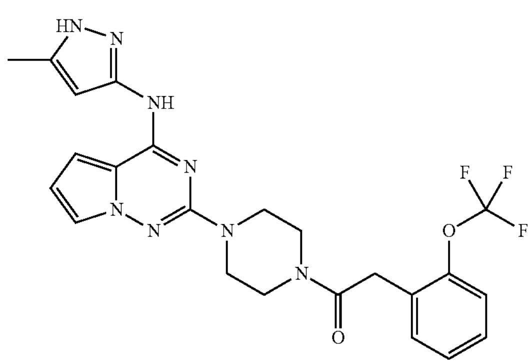 [SMILES: Cc1cc(Nc2nc(N3CCN(C(=O)Cc4ccccc4OC(F)(F)F)CC3)nn3cccc23)n[nH]1] | N-(5-methyl-1H-pyrazol-3-yl)-2-(4-((2-(trifluoromethoxy)phenyl)acetyl)-1-piperazinyl)pyrrolo[2,1-f][1,2,4]triazin-4-amine | 2.39 | 500.93 |

TABLE 1-continued

| Ex. No. | Structure | Name | HPLC Ret. time (min) | m/z [M + H] |
|---|---|---|---|---|
| 97 | 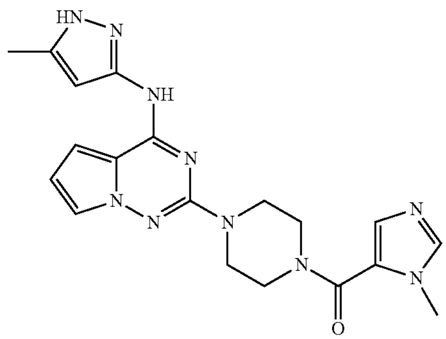 [SMILES: Cc1cc(Nc2nc(N3CCN(C(=O)c4cncn4C)CC3)nn3cccc23)n[nH]1] | 2-(4-((1-methyl-1H-imidazol-5-yl)carbonyl)-1-piperazinyl)-N-(5-methyl-1H-pyrazol-3-yl)pyrrolo[2,1-f][1,2,4]triazin-4-amine | 1.39 | 407.00 |
| 98 | 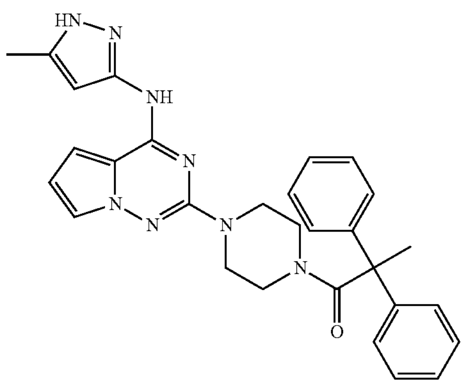 [SMILES: Cc1cc(Nc2nc(N3CCN(C(=O)C(C)(c4ccccc4)c4ccccc4)CC3)nn3cccc23)n[nH]1] | 2-(4-(2,2-diphenylpropanoyl)-1-piperazinyl)-N-(5-methyl-1H-pyrazol-3-yl)pyrrolo[2,1-f][1,2,4]triazin-4-amine | 2.74 | 507.01 |
| 99 | 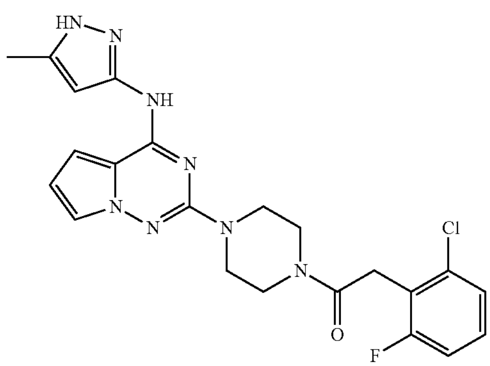 [SMILES: Cc1cc(Nc2nc(N3CCN(C(=O)Cc4c(F)cccc4Cl)CC3)nn3cccc23)n[nH]1] | 2-(4-((2-chloro-6-fluorophenyl)acetyl)-1-piperazinyl)-N-(5-methyl-1H-pyrazol-3-yl)pyrrolo[2,1-f][1,2,4]triazin-4-amine | 2.25 | 468.92 |
| 100 | 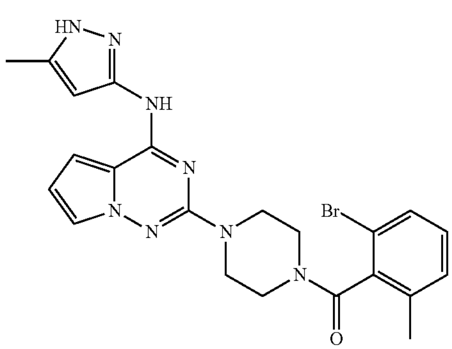 [SMILES: Cc1cc(Nc2nc(N3CCN(C(=O)c4c(C)cccc4Br)CC3)nn3cccc23)n[nH]1] | 2-(4-(2-bromo-6-methylbenzoyl)-1-piperazinyl)-N-(5-methyl-1H-pyrazol-3-yl)pyrrolo[2,1-f][1,2,4]triazin-4-amine | 2.23 | 494.87 |

TABLE 1-continued

| Ex. No. | Structure | Name | HPLC Ret. time (min) | m/z [M + H] |
|---|---|---|---|---|
| 101 | 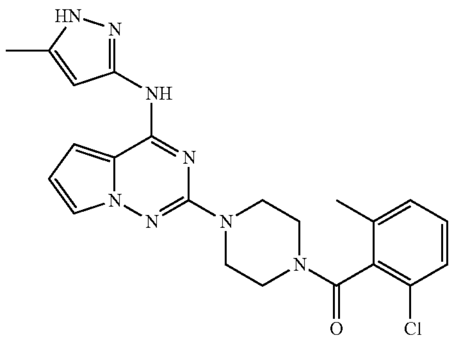 [SMILES: Cc1cc(Nc2nc(N3CCN(C(=O)c4c(C)cccc4Cl)CC3)nn3cccc23)n[nH]1] | 2-(4-(2-chloro-6-methylbenzoyl)-1-piperazinyl)-N-(5-methyl-1H-pyrazol-3-yl)pyrrolo[2,1-f][1,2,4]triazin-4-amine | 2.18 | 450.95 |
| 102 | 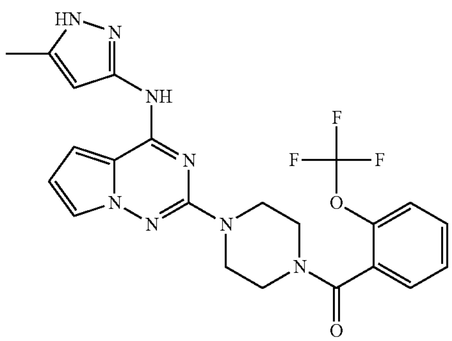 [SMILES: Cc1cc(Nc2nc(N3CCN(C(=O)c4ccccc4OC(F)(F)F)CC3)nn3cccc23)n[nH]1] | N-(5-methyl-1H-pyrazol-3-yl)-2-(4-(2-(trifluoromethoxy)benzoyl)-1-piperazinyl)pyrrolo[2,1-f][1,2,4]triazin-4-amine | 2.25 | 486.94 |
| 103 | 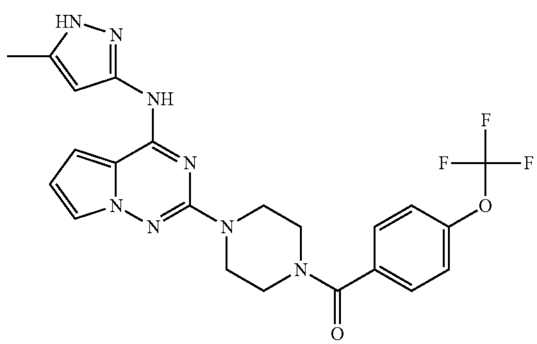 [SMILES: Cc1cc(Nc2nc(N3CCN(C(=O)c4ccc(OC(F)(F)F)cc4)CC3)nn3cccc23)n[nH]1] | N-(5-methyl-1H-pyrazol-3-yl)-2-(4-(4-(trifluoromethoxy)benzoyl)-1-piperazinyl)pyrrolo[2,1-f][1,2,4]triazin-4-amine | 2.38 | 486.94 |
| 104 | 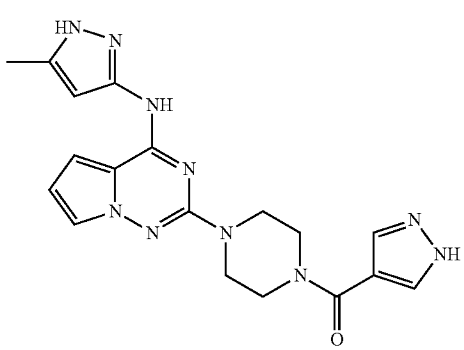 [SMILES: Cc1cc(Nc2nc(N3CCN(C(=O)c4cn[nH]c4)CC3)nn3cccc23)n[nH]1] | N-(5-methyl-1H-pyrazol-3-yl)-2-(4-1H-pyrazol-4-ylcarbonyl)-1-piperazinyl)pyrrolo[2,1-f][1,2,4]triazin-4-amine | 1.36 | 392.99 |

TABLE 1-continued

| Ex. No. | Structure | Name | HPLC Ret. time (min) | m/z [M + H] |
|---|---|---|---|---|
| 105 | 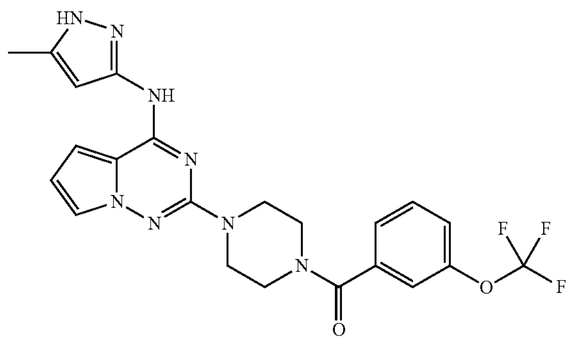 [SMILES: Cc1cc(Nc2nc(N3CCN(C(=O)c4cccc(OC(F)(F)F)c4)CC3)nn3cccc23)n[nH]1] | N-(5-methyl-1H-pyrazol-3-yl)-2-(4-(3-(trifluoromethoxy)benzoyl)-1-piperazinyl)pyrrolo[2,1-f][1,2,4]triazin-4-amine | 2.34 | 486.94 |
| 106 | 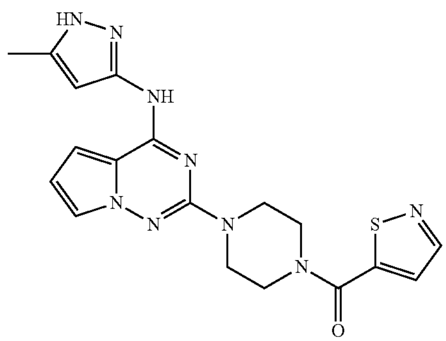 [SMILES: Cc1cc(Nc2nc(N3CCN(C(=O)c4ccns4)CC3)nn3cccc23)n[nH]1] | 2-(4-(5-isothiazolylcarbonyl)-1-piperazinyl)-N-(5-methyl-1H-pyrazol-3-yl)pyrrolo[2,1-f][1,2,4]triazin-4-amine | 1.74 | 409.94 |
| 107 | 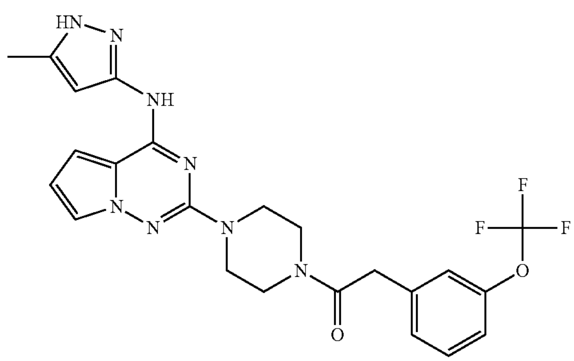 [SMILES: Cc1cc(Nc2nc(N3CCN(C(=O)Cc4cccc(OC(F)(F)F)c4)CC3)nn3cccc23)n[nH]1] | N-(5-methyl-1H-pyrazol-3-yl)-2-(4-((3-(trifluoromethoxy)phenyl)acetyl)-1-piperazinyl)pyrrolo[2,1-f][1,2,4]triazin-4-amine | 2.41 | 500.93 |
| 108 | 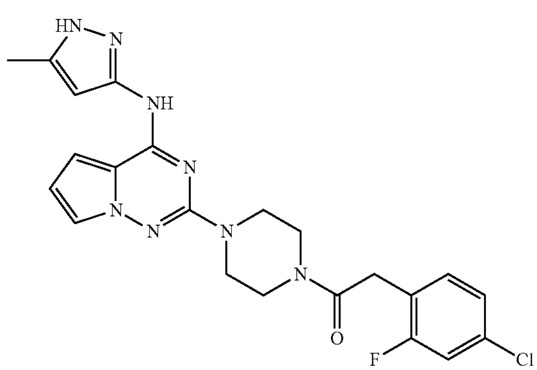 [SMILES: Cc1cc(Nc2nc(N3CCN(C(=O)Cc4ccc(Cl)cc4F)CC3)nn3cccc23)n[nH]1] | 2-(4-((4-chloro-2-fluorophenyl)acetyl)-1-piperazinyl)-N-(5-methyl-1H-pyrazol-3-yl)pyrrolo[2,1-f][1,2,4]triazin-4-amine | 2.32 | 468.94 |

TABLE 1-continued

| Ex. No. | Structure | Name | HPLC Ret. time (min) | m/z [M + H] |
|---|---|---|---|---|
| 109 | 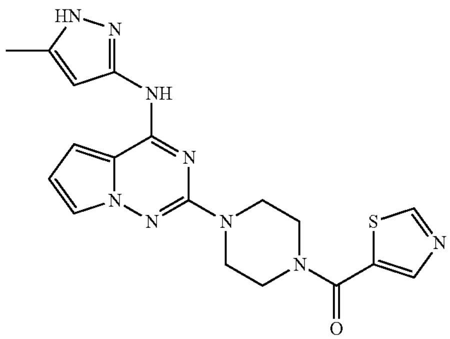 [SMILES: Cc1cc(Nc2nc(N3CCN(C(=O)c4cncs4)CC3)nn3cccc23)n[nH]1] | N-(5-methyl-1H-pyrazol-3-yl)-2-(4-(1,3-thiazol-5-ylcarbonyl)-1-piperazinyl)pyrrolo[2,1-f][1,2,4]triazin-4-amine | 1.57 | 409.95 |
| 110 | 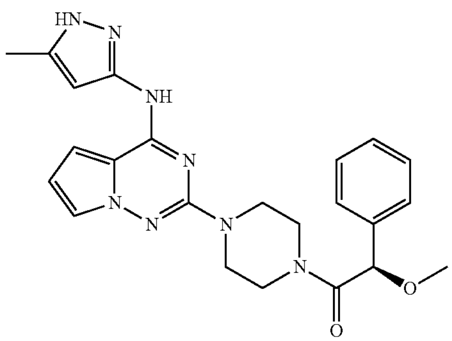 | 2-(4-((2R)-2-methoxy-2-phenylacetyl)-1-piperazinyl)-N-(5-methyl-1H-pyrazol-3-yl)pyrrolo[2,1-f][1,2,4]triazin-4-amine | 1.94 | 446.99 |
| 111 | 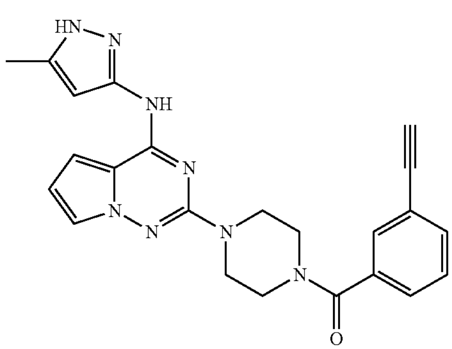 [SMILES: C#Cc1cccc(C(=O)N2CCN(c3nc(Nc4cc(C)[nH]n4)c4cccn4n3)CC2)c1] | 2-(4-(3-ethynylbenzoyl)-1-piperazinyl)-N-(5-methyl-1H-pyrazol-3-yl)pyrrolo[2,1-f][1,2,4]triazin-4-amine | 2.09 | 426.98 |
| 112 | 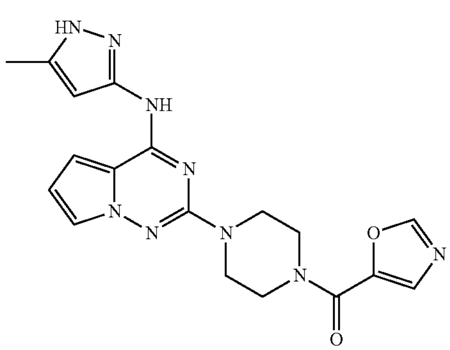 [SMILES: Cc1cc(Nc2nc(N3CCN(C(=O)c4cnco4)CC3)nn3cccc23)n[nH]1] | N-(5-methyl-1H-pyrazol-3-yl)-2-(4-(1,3-oxazol-5-ylcarbonyl)-1-piperazinyl)pyrrolo[2,1-f][1,2,4]triazin-4-amine | 1.50 | 393.98 |

TABLE 1-continued

| Ex. No. | Structure | Name | HPLC Ret. time (min) | m/z [M + H] |
|---|---|---|---|---|
| 113 | 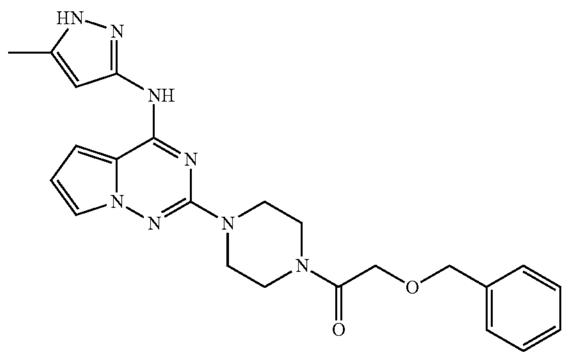 [SMILES: Cc1cc(Nc2nc(N3CCN(C(=O)COCc4ccccc4)CC3)nn3cccc23)n[nH]1] | 2-(4-((benzyloxy)acetyl)-1-piperazinyl)-N-(5-methyl-1H-pyrazol-3-yl)pyrrolo[2,1-f][1,2,4]triazin-4-amine | 2.01 | 446.99 |
| 114 | 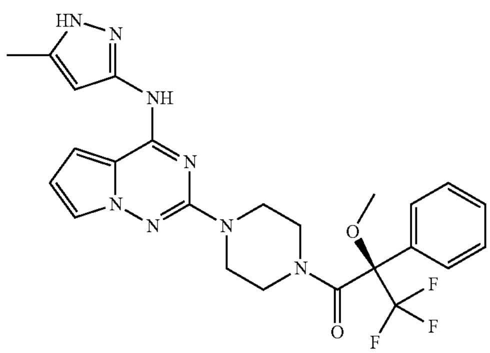 [SMILES: CO[C@@](C(=O)N1CCN(c2nc(Nc3cc(C)[nH]n3)c3cccn3n2)CC1)(c1ccccc1)C(F)(F)F] | N-(5-methyl-1H-pyrazol-3-yl)-2-(4-((2R)-3,3,3-trifluoro-2-methoxy-2-phenylpropanoyl)-1-piperazinyl)pyrrolo[2,1-f][1,2,4]triazin-4-amine | 2.62 | 514.95 |
| 115 | 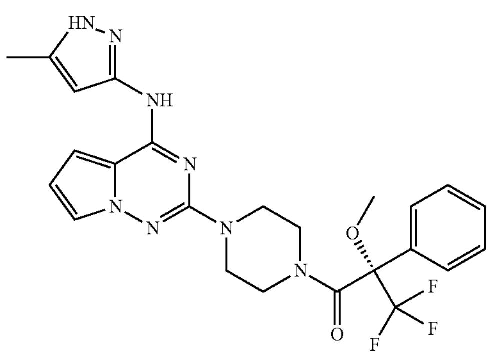 [SMILES: CO[C@](C(=O)N1CCN(c2nc(Nc3cc(C)[nH]n3)c3cccn3n2)CC1)(c1ccccc1)C(F)(F)F] | N-(5-methyl-1H-pyrazol-3-yl)-2-(4-((2S)-3,3,3-trifluoro-2-methoxy-2-phenylpropanoyl)-1-piperazinyl)pyrrolo[2,1-f][1,2,4]triazin-4-amine | 2.63 | 514.96 |
| 116 | 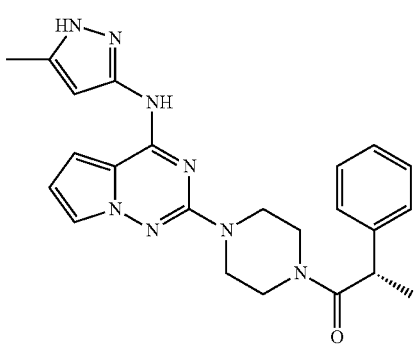 [SMILES: Cc1cc(Nc2nc(N3CCN(C(=O)[C@@H](C)c4ccccc4)CC3)nn3cccc23)n[nH]1] | N-(5-methyl-1H-pyrazol-3-yl)-2-(4-((2S)-2-phenylpropanoyl)-1-piperazinyl)pyrrolo[2,1-f][1,2,4]triazin-4-amine | 2.17 | 431.03 |

TABLE 1-continued

| Ex. No. | Structure | Name | HPLC Ret. time (min) | m/z [M + H] |
|---|---|---|---|---|
| 117 | 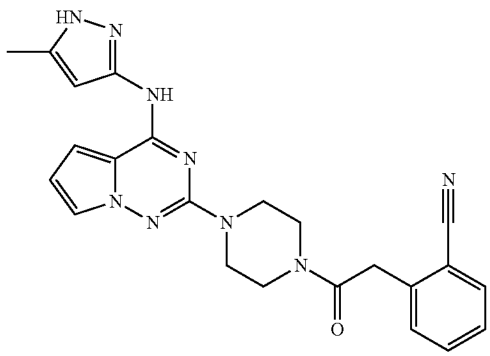 [SMILES: Cc1cc(Nc2nc(N3CCN(C(=O)Cc4ccccc4C#N)CC3)nn3cccc23)n[nH]1] | 2-(2-(4-(4-((5-methyl-1H-pyrazol-3-yl)amino)pyrrolo[2,1-f][1,2,4]triazin-2-yl)-1-piperazinyl)-2-oxoethyl)benzonitrile | 1.92 | 441.98 |
| 118 | 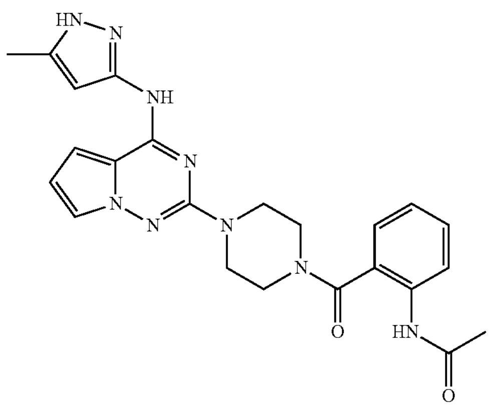 [SMILES: CC(=O)Nc1ccccc1C(=O)N1CCN(c2nc(Nc3cc(C)[nH]n3)c3cccn3n2)CC1] | N-(2-((4-(4-((5-methyl-1H-pyrazol-3-yl)amino)pyrrolo[2,1-f][1,2,4]triazin-2-yl)-1-piperazinyl)carbonyl)phenyl)acetamide | 1.59 | 460.01 |
| 119 | 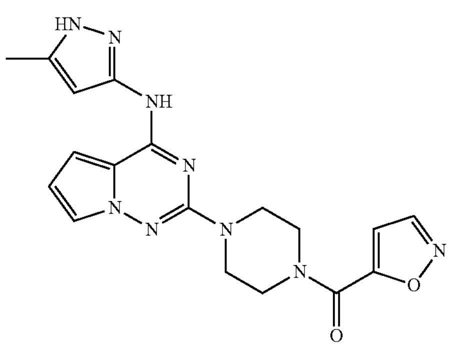 [SMILES: Cc1cc(Nc2nc(N3CCN(C(=O)c4ccno4)CC3)nn3cccc23)n[nH]1] | 2-(4-(5-isoxazolylcarbonyl)-1-piperazinyl)-N-(5-methyl-1H-pyrazol-3-yl)pyrrolo[2,1-f][1,2,4]triazin-4-amine | 1.72 | 393.98 |
| 120 | 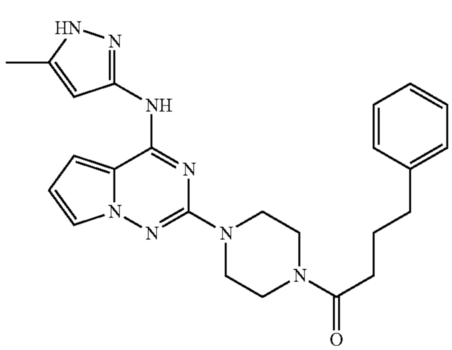 [SMILES: Cc1cc(Nc2nc(N3CCN(C(=O)CCCc4ccccc4)CC3)nn3cccc23)n[nH]1] | N-(5-methyl-1H-pyrazol-3-yl)-2-(4-(4-phenylbutanoyl)-1-piperazinyl)pyrrolo[2,1-f][1,2,4]triazin-4-amine | 2.27 | 445.07 |

TABLE 1-continued

| Ex. No. | Structure | Name | HPLC Ret. time (min) | m/z [M + H] |
|---|---|---|---|---|
| 121 | 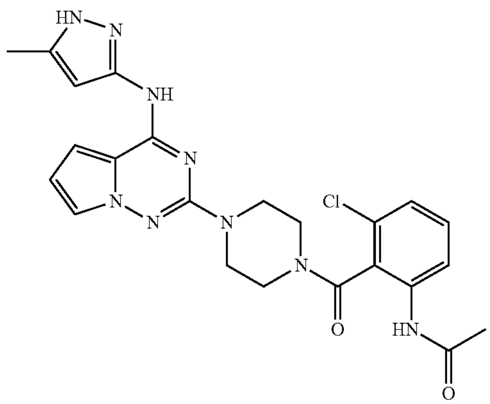 [SMILES: CC(=O)Nc1cccc(Cl)c1C(=O)N1CCN(c2nc(Nc3cc(C)[nH]n3)c3cccn3n2)CC1] | N-(3-chloro-2-((4-(4-((5-methyl-1H-pyrazol-3-yl)amino)pyrrolo[2,1-f][1,2,4]triazin-2-yl)-1-piperazinyl)carbonyl)phenyl)acetamide | 1.76 | 493.94 |
| 122 | 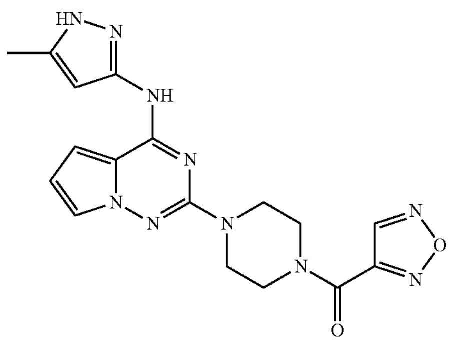 [SMILES: Cc1cc(Nc2nc(N3CCN(C(=O)c4cnon4)CC3)nn3cccc23)n[nH]1] | N-(5-methyl-1H-pyrazol-3-yl)-2-(4-(1,2,5-oxadiazol-3-ylcarbonyl)-1-piperazinyl)pyrrolo[2,1-f][1,2,4]triazin-4-amine | 1.35 | 395.00 |
| 123 | 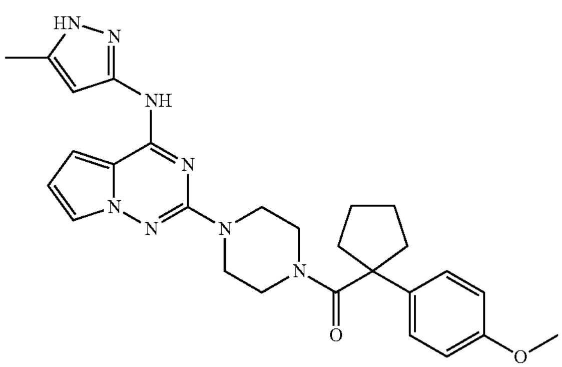 | 2-(4-((1-(4-methoxyphenyl)cyclopentyl)carbonyl)-1-piperazinyl)-N-(5-methyl-1H-pyrazol-3-yl)pyrrolo[2,1-f][1,2,4]triazin-4-amine | 2.89 | 501.06 |
| 124 | 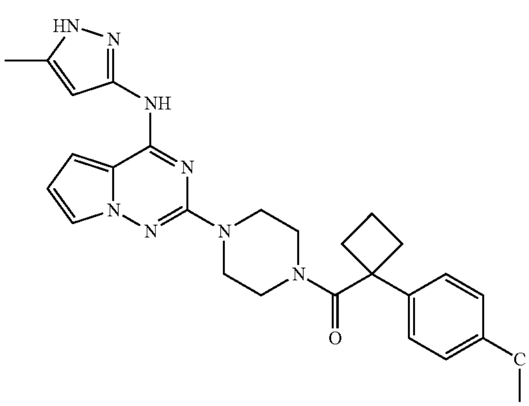 [SMILES: CCc1ccc(C2(C(=O)N3CCN(c4nc(Nc5cc(C)[nH]n5)c5cccn5n4)CC3)CCC2)cc1] | 2-(4-((1-(4-chlorophenyl)cyclobutyl)carbonyl)-1-piperazinyl)-N-(5-methyl-1H-pyrazol-3-yl)pyrrolo[2,1-f][1,2,4]triazin-4-amine | 2.93 | 490.99 |

TABLE 1-continued

| Ex. No. | Structure | Name | HPLC Ret. time (min) | m/z [M + H] |
|---|---|---|---|---|
| 125 | 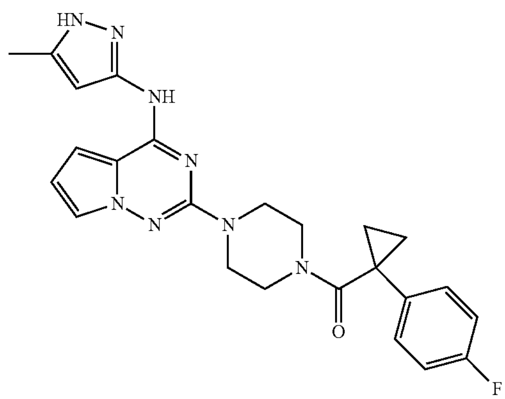 [SMILES: Cc1cc(Nc2nc(N3CCN(C(=O)C4(c5ccc(F)cc5)CC4)CC3)nn3cccc23)n[nH]1] | 2-(4-((1-(4-fluorophenyl)cyclopropyl)carbonyl)-1-piperazinyl)-N-(5-methyl-1H-pyrazol-3-yl)pyrrolo[2,1-f][1,2,4]triazin-4-amine | 2.62 | 461.03 |
| 126 | 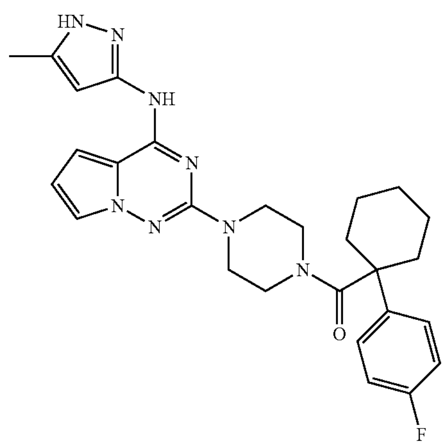 [SMILES: Cc1cc(Nc2nc(N3CCN(C(=O)C4(c5ccc(F)cc5)CCCCC4)CC3)nn3cccc23)n[nH]1] | 2-(4-((1-(4-fluorophenyl)cyclohexyl)carbonyl)-1-piperazinyl)-N-(5-methyl-1H-pyrazol-3-yl)pyrrolo[2,1-f][1,2,4]triazin-4-amine | 3.08 | 503.08 |
| 127 | 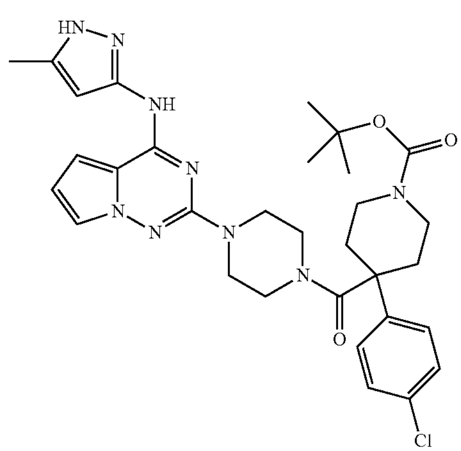 [SMILES: Cc1cc(Nc2nc(N3CCN(C(=O)C4(c5ccc(Cl)cc5)CCN(C(=O)OC(C)(C)C)CC4)CC3)nn3cccc23)n[nH]1] | tert-butyl 4-(4-chlorophenyl)-4-((4-(4-((5-methyl-1H-pyrazol-3-yl)amino)pyrrolo[2,1-f][1,2,4]triazin-2-yl)-1-piperazinyl)carbonyl)-1-piperidinecarboxylate | 3.14 | 620.08 |

TABLE 1-continued

| Ex. No. | Structure | Name | HPLC Ret. time (min) | m/z [M + H] |
|---|---|---|---|---|
| 128 | 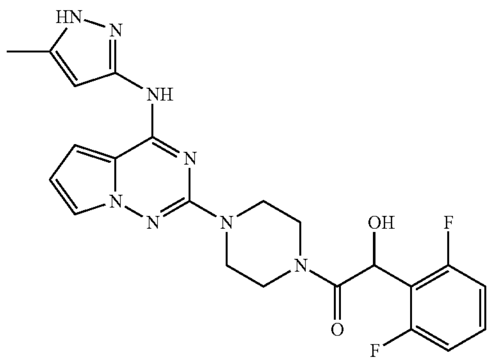 [SMILES: Cc1cc(Nc2nc(N3CCN(C(=O)C(O)c4c(F)cccc4F)CC3)nn3cccc23)n[nH]1] | 1-(2,6-difluorophenyl)-2-(4-(4-((5-methyl-1H-pyrazol-3-yl)amino)pyrrolo[2,1-f][1,2,4]triazin-2-yl)-1-piperazinyl)-2-oxoethanol | 2.35 | 469.01 |
| 129 | 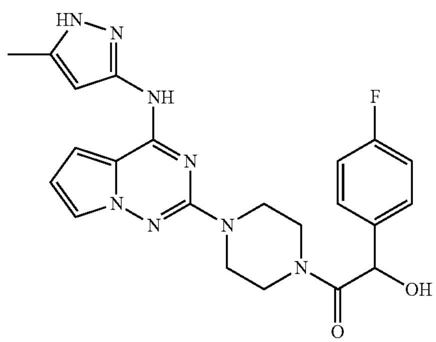 [SMILES: Cc1cc(Nc2nc(N3CCN(C(=O)C(O)c4ccc(F)cc4)CC3)nn3cccc23)n[nH]1] | 1-(4-fluorophenyl)-2-(4-(4-((5-methyl-1H-pyrazol-3-yl)amino)pyrrolo[2,1-f][1,2,4]triazin-2-yl)-1-piperazinyl)-2-oxoethanol | 2.30 | 451.02 |
| 130 | 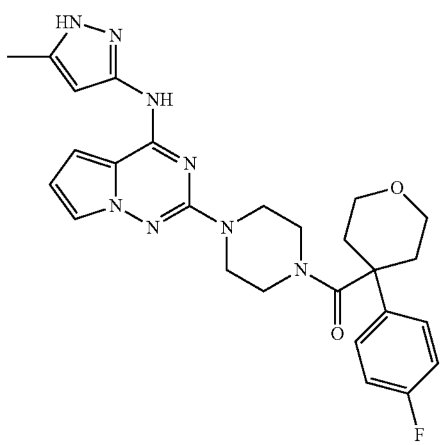 [SMILES: Cc1cc(Nc2nc(N3CCN(C(=O)C4(c5ccc(F)cc5)CCOCC4)CC3)nn3cccc23)n[nH]1] | 2-(4-((4-(4-fluorophenyl)tetrahydro-2H-pyran-4-yl)carbonyl)-1-piperazinyl)-N-(5-methyl-1H-pyrazol-3-yl)pyrrolo[2,1-f][1,2,4]triazin-4-amine | 2.48 | 505.06 |
| 131 | 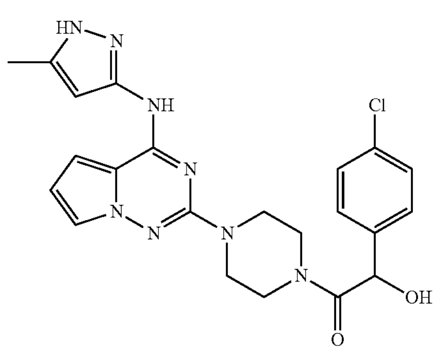 [SMILES: Cc1cc(Nc2nc(N3CCN(C(=O)C(O)c4ccc(Cl)cc4)CC3)nn3cccc23)n[nH]1] | 1-(4-chlorophenyl)-2-(4-(4-((5-methyl-1H-pyrazol-3-yl)amino)pyrrolo[2,1-f][1,2,4]triazin-2-yl)-1-piperazinyl)-2-oxoethanol | 2.44 | 467.01 |

TABLE 1-continued

| Ex. No. | Structure | Name | HPLC Ret. time (min) | m/z [M + H] |
|---|---|---|---|---|
| 132 | 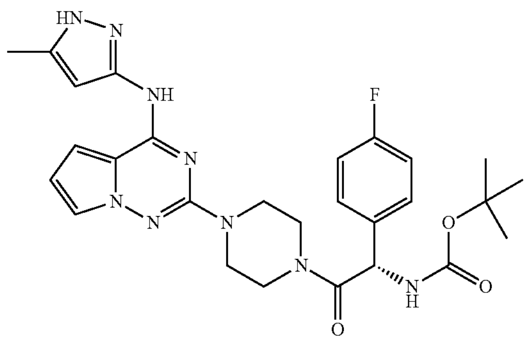 [SMILES: Cc1cc(Nc2nc(N3CCN(C(=O)[C@@H](NC(=O)OC(C)(C)C)c4ccc(F)cc4)CC3)nn3cccc23)n[nH]1] | tert-butyl((1S)-1-(4-fluorophenyl)-2-(4-(4-((5-methyl-1H-pyrazol-3-yl)amino)pyrrolo[2,1-f][1,2,4]triazin-2-yl)-1-piperazinyl)-2-oxoethyl)carbamate | 2.74 | 550.06 |
| 133 | 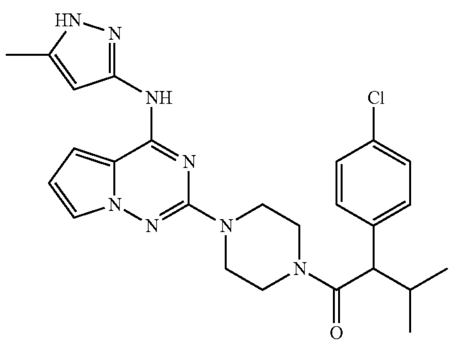 [SMILES: Cc1cc(Nc2nc(N3CCN(C(=O)C(c4ccc(Cl)cc4)C(C)C)CC3)nn3cccc23)n[nH]1] | 2-(4-(2-(4-chlorophenyl)-3-methylbutanoyl)-1-piperazinyl)-N-(5-methyl-1H-pyrazol-3-yl)pyrrolo[2,1-f][1,2,4]triazin-4-amine | 2.98 | 493.03 |
| 134 | 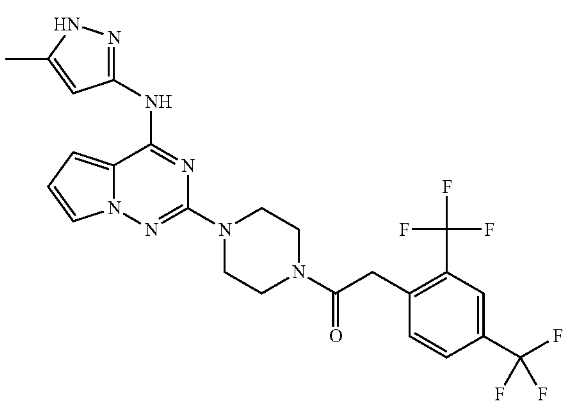 [SMILES: Cc1cc(Nc2nc(N3CCN(C(=O)Cc4ccc(C(F)(F)F)cc4C(F)(F)F)CC3)nn3cccc23)n[nH]1] | 2-(4-((2,4-bis(trifluoromethyl)phenyl)acetyl)-1-piperazinyl)-N-(5-methyl-1H-pyrazol-3-yl)pyrrolo[2,1-f][1,2,4]triazin-4-amine | 2.87 | 553.01 |
| 135 | 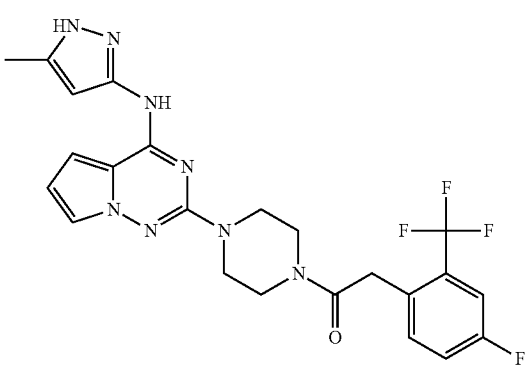 [SMILES: Cc1cc(Nc2nc(N3CCN(C(=O)Cc4ccc(F)cc4C(F)(F)F)CC3)nn3cccc23)n[nH]1] | 2-(4-((4-fluoro-2-(trifluoromethyl)phenyl)acetyl)-1-piperazinyl)-N-(5-methyl-1H-pyrazol-3-yl)pyrrolo[2,1-f][1,2,4]triazin-4-amine | 2.65 | 503.00 |

TABLE 1-continued

| Ex. No. | Structure | Name | HPLC Ret. time (min) | m/z [M + H] |
|---|---|---|---|---|
| 136 | 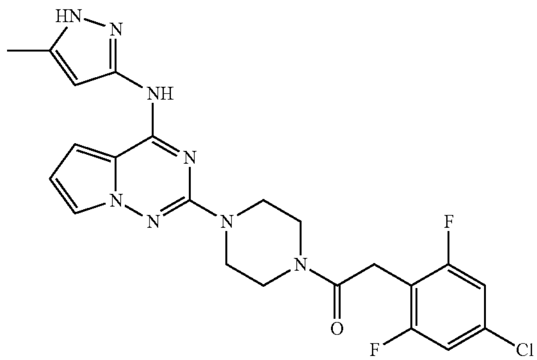 [SMILES: Cc1cc(Nc2nc(N3CCN(C(=O)Cc4c(F)cc(Cl)cc4F)CC3)nn3cccc23)n[nH]1] | 2-(4-((4-chloro-2,6-difluorophenyl)acetyl)-1-piperazinyl)-N-(5-methyl-1H-pyrazol-3-yl)pyrrolo[2,1-f][1,2,4]triazin-4-amine | 2.67 | 486.95 |
| 137 | 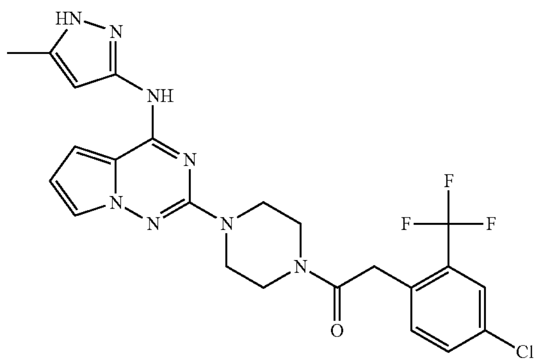 [SMILES: Cc1cc(Nc2nc(N3CCN(C(=O)Cc4ccc(Cl)cc4C(F)(F)F)CC3)nn3cccc23)n[nH]1] | 2-(4-((4-chloro-2-(trifluoromethyl)phenyl)acetyl)-1-piperazinyl)-N-(5-methyl-1H-pyrazol-3-yl)pyrrolo[2,1-f][1,2,4]triazin-4-amine | 2.79 | 518.96 |
| 138 | 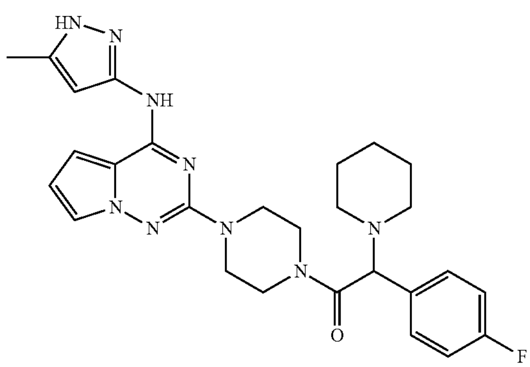 [SMILES: Cc1cc(Nc2nc(N3CCN(C(=O)C(c4ccc(F)cc4)N4CCCCC4)CC3)nn3cccc23)n[nH]1] | 2-(4-((4-fluorophenyl)(1-piperidinyl)acetyl)-1-piperazinyl)-N-(5-methyl-1H-pyrazol-3-yl)pyrrolo[2,1-f][1,2,4]triazin-4-amine | 2.41 | 518.08 |
| 139 | 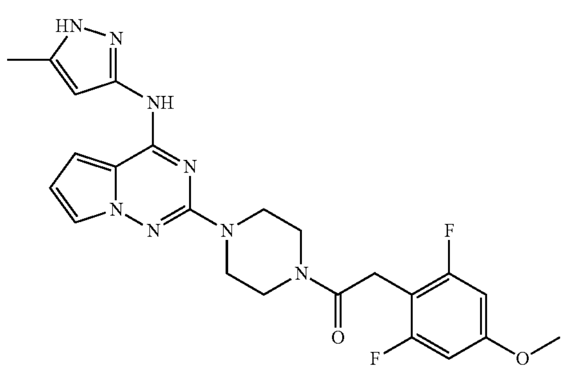 | 2-(4-((2,6-difluoro-4-methoxyphenyl)acetyl)-1-piperazinyl)-N-(5-methyl-1H-pyrazol-3-yl)pyrrolo[2,1-f][1,2,4]triazin-4-amine | 2.50 | 483.01 |

TABLE 1-continued

| Ex. No. | Structure | Name | HPLC Ret. time (min) | m/z [M + H] |
|---|---|---|---|---|
| 140 | 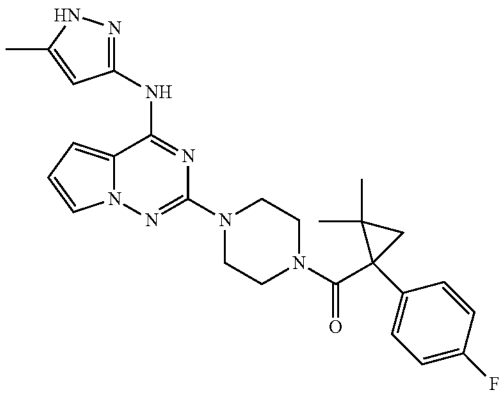 [SMILES: Cc1cc(Nc2nc(N3CCN(C(=O)C4(c5ccc(F)cc5)CC4(C)C)CC3)nn3cccc23)n[nH]1] | 2-(4-((1-(4-fluorophenyl)-2,2-dimethylcyclopropyl)carbonyl)-1-piperazinyl)-N-(5-methyl-1H-pyrazol-3-yl)pyrrolo[2,1-f][1,2,4]triazin-4-amine | 2.77 | 489.06 |
| 141 | 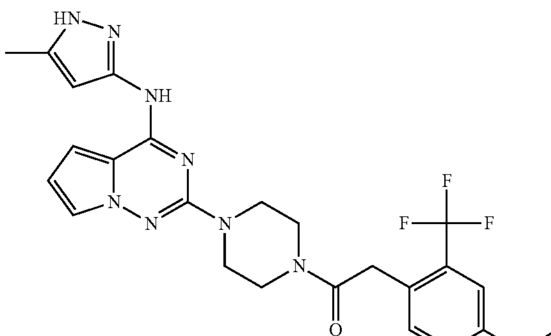 | 2-(4-((4-methoxy-2-(trifluoromethyl)phenyl)acetyl)-1-piperazinyl)-N-(5-methyl-1H-pyrazol-3-yl)pyrrolo[2,1-f][1,2,4]triazin-4-amine | 2.62 | 515.00 |
| 142 | 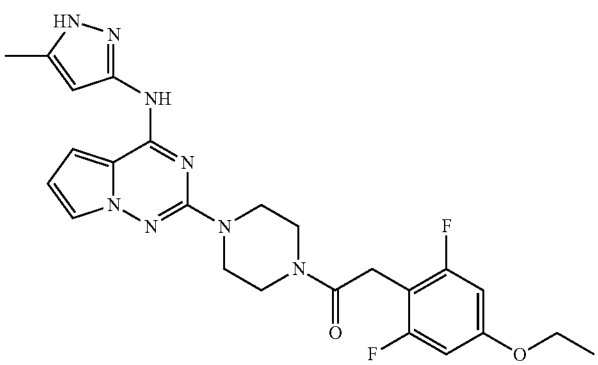 [SMILES: CCOc1cc(F)c(CC(=O)N2CCN(c3nc(Nc4cc(C)[nH]n4)c4cccn4n3)CC2)c(F)c1] | 2-(4-((4-ethoxy-2,6-difluorophenyl)acetyl)-1-piperazinyl)-N-(5-methyl-1H-pyrazol-3-yl)pyrrolo[2,1-f][1,2,4]triazin-4-amine | 2.66 | 497.02 |
| 143 | 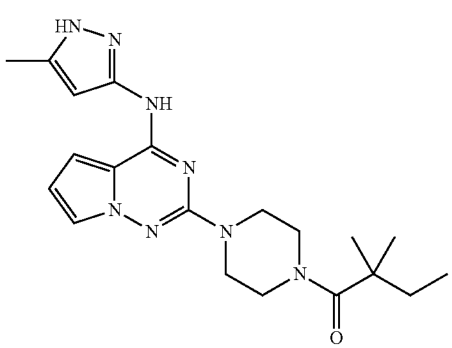 [SMILES: CCC(C)(C)C(=O)N1CCN(c2nc(Nc3cc(C)[nH]n3)c3cccn3n2)CC1] | 2-(4-(2,2-dimethyl-butanoyl)-1-piperazinyl)-N-(5-methyl-1H-pyrazol-3-yl)pyrrolo[2,1-f][1,2,4]triazin-4-amine | 2.60 | 397.08 |

TABLE 1-continued

| Ex. No. | Structure | Name | HPLC Ret. time (min) | m/z [M + H] |
|---|---|---|---|---|
| 144 | 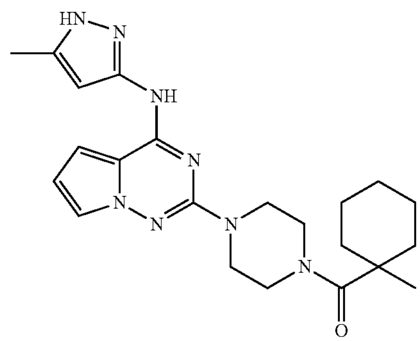 [SMILES: Cc1cc(Nc2nc(N3CCN(C(=O)C4(C)CCCCC4)CC3)nn3cccc23)n[nH]1] | 2-(4-((1-methylcyclo-hexyl)carbonyl)-1-piperazinyl)-N-(5-methyl-1H-pyrazol-3-yl)pyrrolo[2,1-f][1,2,4]triazin-4-amine | 2.83 | 423.08 |
| 145 | 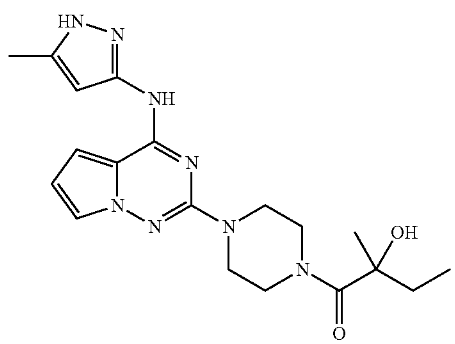 [SMILES: CCC(C)(O)C(=O)N1CCN(c2nc(Nc3cc(C)[nH]n3)c3cccn3n2)CC1] | 2-methyl-1-(4-(4-((5-methyl-1H-pyrazol-3-yl)amino)pyrrolo[2,1-f][1,2,4]triazin-2-yl)-1-piperazinyl)-1-oxo-2-butanol | 2.32 | 399.05 |
| 146 | 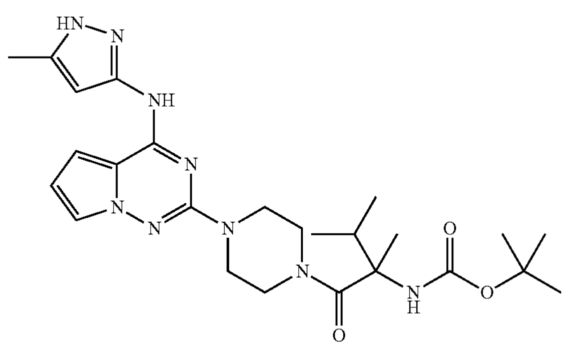 [SMILES: Cc1cc(Nc2nc(N3CCN(C(=O)C(C)(NC(=O)OC(C)(C)C)C(C)C)CC3)nn3cccc23)n[nH]1] | tert-butyl(1,2-dimethyl-1-((4-(4-((5-methyl-1H-pyrazol-3-yl)amino)pyrrolo[2,1-f][1,2,4]triazin-2-yl)-1-piperazinyl)carbonyl)propyl)carbamate | 2.60 | 512.11 |
| 147 | 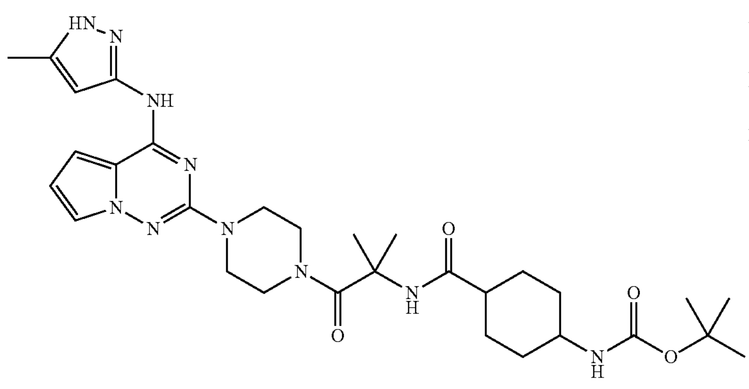 [SMILES: Cc1cc(Nc2nc(N3CCN(C(=O)C(C)(C)NC(=O)C4CCC(NC(=O)OC(C)(C)C)CC4)CC3)nn3cccc23)n[nH]1] | tert-butyl(4-((1,1-dimethyl-2-(4-(4-((5-methyl-1H-pyrazol-3-yl)amino)pyrrolo[2,1-f][1,2,4]triazin-2-yl)-1-piperazinyl)-2-oxoethyl)carbamoyl)cyclohexyl)carbamate | 2.43 | 609.12 |

TABLE 1-continued

| Ex. No. | Structure | Name | HPLC Ret. time (min) | m/z [M + H] |
|---|---|---|---|---|
| 148 | 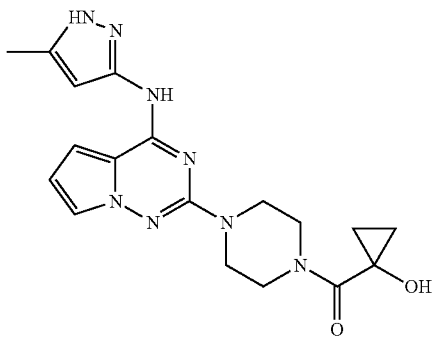 [SMILES: Cc1cc(Nc2nc(N3CCN(C(=O)C4(O)CC4)CC3)nn3cccc23)n[nH]1] | 1-((4-(4-((5-methyl-1H-pyrazol-3-yl)amino)pyrrolo[2,1-f][1,2,4]triazin-2-yl)-1-piperazinyl)carbonyl)cyclopropanol | 2.21 | 383.04 |
| 149 | 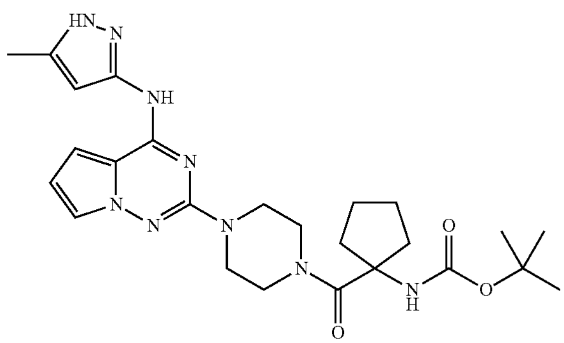 [SMILES: Cc1cc(Nc2nc(N3CCN(C(=O)C4(NC(=O)OC(C)(C)C)CCCC4)CC3)nn3cccc23)n[nH]1] | tert-butyl(1-((4-(4-((5-methyl-1H-pyrazol-3-yl)amino)pyrrolo[2,1-f][1,2,4]triazin-2-yl)-1-piperazinyl)carbonyl)cyclopentyl)carbamate | 2.56 | 510.06 |
| 150 | 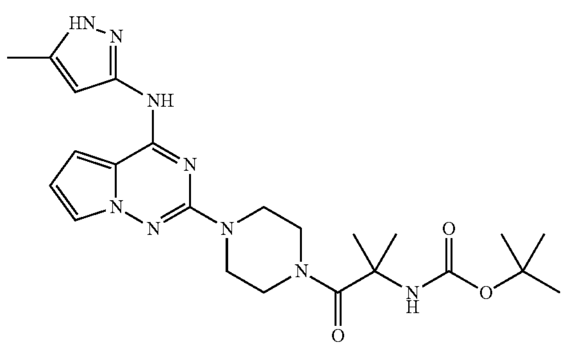 [SMILES: Cc1cc(Nc2nc(N3CCN(C(=O)C(C)(C)NC(=O)OC(C)(C)C)CC3)nn3cccc23)n[nH]1] | tert-butyl(1,1-dimethyl-2-(4-(4-((5-methyl-1H-pyrazol-3-yl)amino)pyrrolo[2,1-f][1,2,4]triazin-2-yl)-1-piperazinyl)-2-oxoethyl)carbamate | 2.44 | 484.05 |
| 151 | 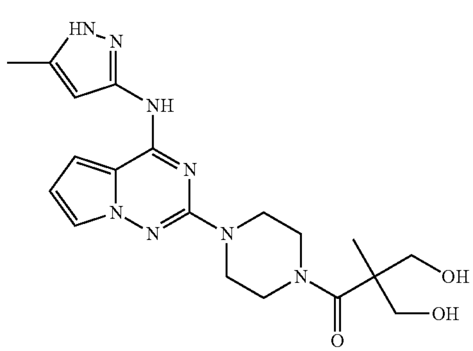 [SMILES: Cc1cc(Nc2nc(N3CCN(C(=O)C(C)(CO)CO)CC3)nn3cccc23)n[nH]1] | 2-methyl-2-((4-(4-((5-methyl-1H-pyrazol-3-yl)amino)pyrrolo[2,1-f][1,2,4]triazin-2-yl)-1-piperazinyl)carbonyl)-1,3-propanediol | 2.13 | 415.04 |

TABLE 1-continued

| Ex. No. | Structure | Name | HPLC Ret. time (min) | m/z [M + H] |
|---|---|---|---|---|
| 152 | 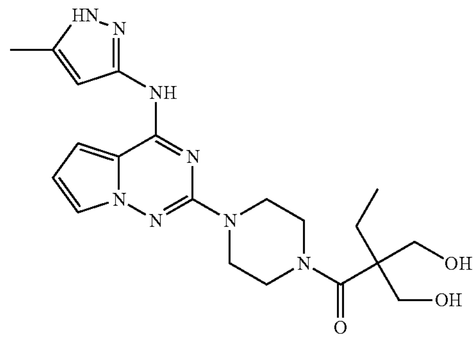 [SMILES: CCC(CO)(CO)C(=O)N1CCN(c2nc(Nc3cc(C)[nH]n3)c3cccn3n2)CC1] | 2-ethyl-2-((4-(4-((5-methyl-1H-pyrazol-3-yl)amino)pyrrolo[2,1-f][1,2,4]triazin-2-yl)-1-piperazinyl)carbonyl)-1,3-propanediol | 2.18 | 429.03 |
| 153 | 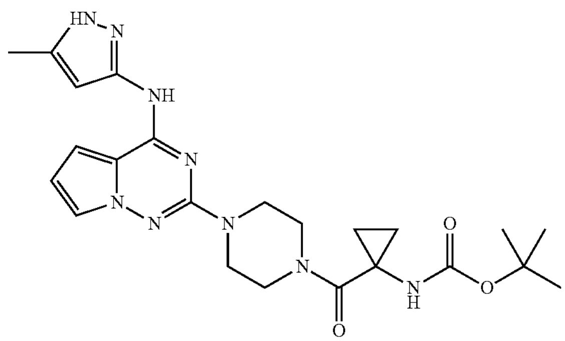 [SMILES: Cc1cc(Nc2nc(N3CCN(C(=O)C4(NC(=O)OC(C)(C)C)CC4)CC3)nn3cccc23)n[nH]1] | tert-butyl(1-((4-(4-((5-methyl-1H-pyrazol-3-yl)amino)pyrrolo[2,1-f][1,2,4]triazin-2-yl)-1-piperazinyl)carbonyl)cyclopropyl)carbamate | 2.39 | 482.05 |
| 154 | 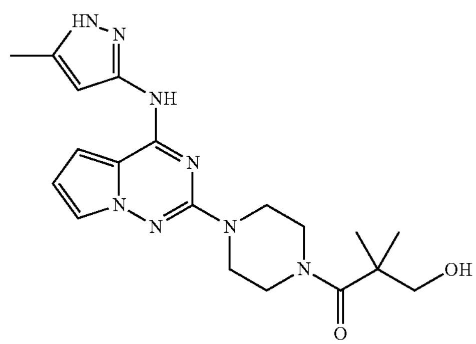 [SMILES: Cc1cc(Nc2nc(N3CCN(C(=O)C(C)(C)CO)CC3)nn3cccc23)n[nH]1] | 2,2-dimethyl-3-(4-(4-((5-methyl-1H-pyrazol-3-yl)amino)pyrrolo[2,1-f][1,2,4]triazin-2-yl)-1-piperazinyl)-3-oxo-1-propanol | 2.28 | 399.05 |
| 155 | 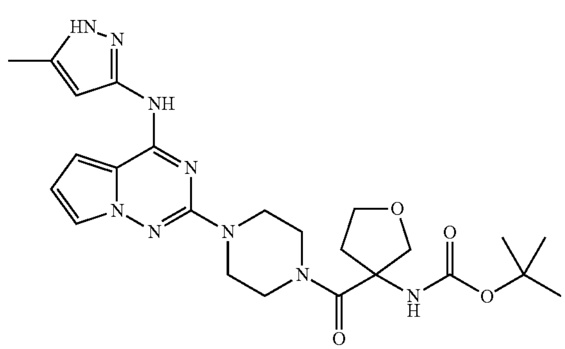 [SMILES: Cc1cc(Nc2nc(N3CCN(C(=O)C4(NC(=O)OC(C)(C)C)CCOC4)CC3)nn3cccc23)n[nH]1] | tert-butyl(3-((4-(4-((5-methyl-1H-pyrazol-3-yl)amino)pyrrolo[2,1-f][1,2,4]triazin-2-yl)-1-piperazinyl)carbonyl)tetrahydro-3-furanyl)carbamate | 2.37 | 512.04 |

TABLE 1-continued

| Ex. No. | Structure | Name | HPLC Ret. time (min) | m/z [M + H] |
|---|---|---|---|---|
| 156 | 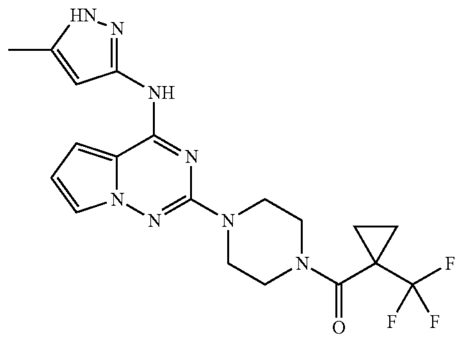 [SMILES: Cc1cc(Nc2nc(N3CCN(C(=O)C4(C(F)(F)F)CC4)CC3)nn3cccc23)n[nH]1] | N-(5-methyl-1H-pyrazol-3-yl)-2-(4-((1-(trifluoromethyl)cyclopropyl)carbonyl)-1-piperazinyl)pyrrolo[2,1-f][1,2,4]triazin-4-amine | 2.54 | 435.00 |
| 157 | 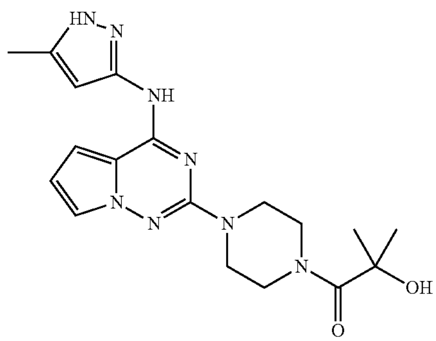 [SMILES: Cc1cc(Nc2nc(N3CCN(C(=O)C(C)(C)O)CC3)nn3cccc23)n[nH]1] | 2-methyl-1-(4-(4-((5-methyl-1H-pyrazol-3-yl)amino)pyrrolo[2,1-f][1,2,4]triazin-2-yl)-1-piperazinyl)-1-oxo-2-propanol | 2.21 | 385.02 |
| 158 | 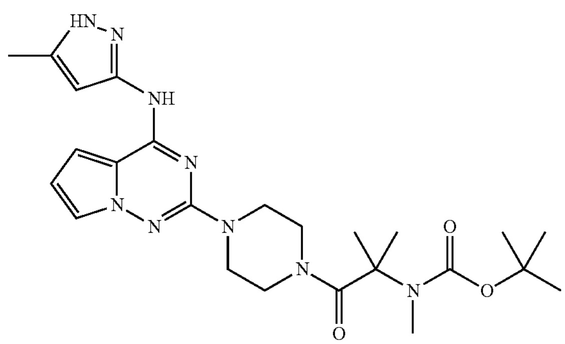 [SMILES: Cc1cc(Nc2nc(N3CCN(C(=O)C(C)(C)N(C)C(=O)OC(C)(C)C)CC3)nn3cccc23)n[nH]1] | tert-butyl(1,1-dimethyl-2-(4-(4-((5-methyl-1H-pyrazol-3-yl)amino)pyrrolo[2,1-f][1,2,4]triazin-2-yl)-1-piperazinyl)-2-oxoethyl)methylcarbamate | 2.57 | 498.05 |
| 159 | 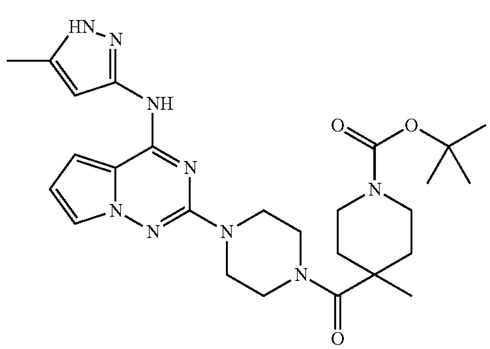 [SMILES: Cc1cc(Nc2nc(N3CCN(C(=O)C4(C)CCN(C(=O)OC(C)(C)C)CC4)CC3)nn3cccc23)n[nH]1] | tert-butyl 4-methyl-4-((4-(4-((5-methyl-1H-pyrazol-3-yl)amino)pyrrolo[2,1-f][1,2,4]triazin-2-yl)-1-piperazinyl)carbonyl)-1-piperidinecarboxylate | 2.74 | 524.02 |

TABLE 1-continued

| Ex. No. | Structure | Name | HPLC Ret. time (min) | m/z [M + H] |
|---|---|---|---|---|
| 160 | 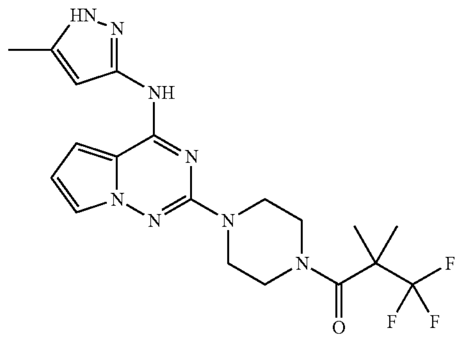 [SMILES: Cc1cc(Nc2nc(N3CCN(C(=O)C(C)(C)C(F)(F)F)CC3)nn3cccc23)n[nH]1] | N-(5-methyl-1H-pyrazol-3-yl)-2-(4-(3,3,3-trifluoro-2,2-dimethylpropanoyl)-1-piperazinyl)pyrrolo[2,1-f][1,2,4]triazin-4-amine | 2.67 | 436.99 |
| 161 | 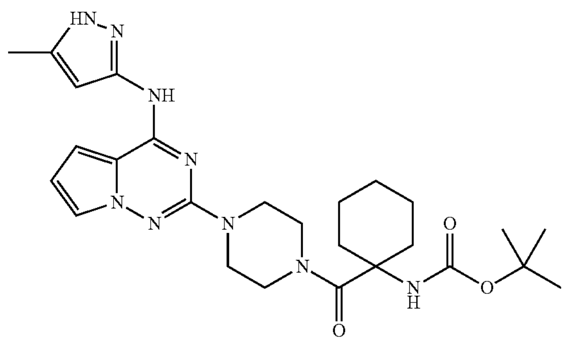 [SMILES: Cc1cc(Nc2nc(N3CCN(C(=O)C4(NC(=O)OC(C)(C)C)CCCCC4)CC3)nn3cccc23)n[nH]1] | tert-butyl(1-((4-(4-((5-methyl-1H-pyrazol-3-yl)amino)pyrrolo[2,1-f][1,2,4]triazin-2-yl)-1-piperazinyl)carbonyl)cyclohexyl)carbamate | 2.66 | 524.06 |
| 162 | 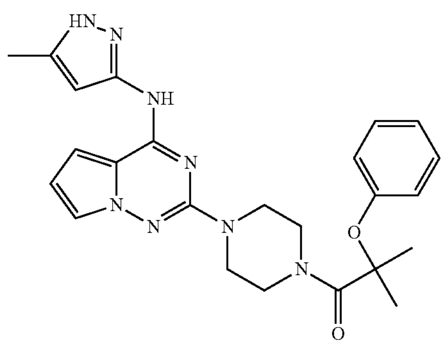 [SMILES: Cc1cc(Nc2nc(N3CCN(C(=O)C(C)(C)Oc4ccccc4)CC3)nn3cccc23)n[nH]1] | 2-(4-(2-methyl-2-phenoxypropanoyl)-1-piperazinyl)-N-(5-methyl-1H-pyrazol-3-yl)pyrrolo[2,1-f][1,2,4]triazin-4-amine | 2.84 | 461.02 |
| 163 | 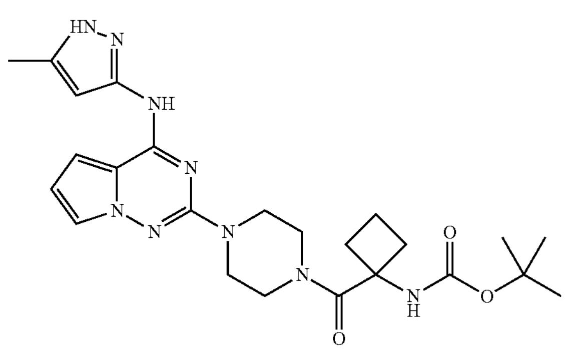 [SMILES: Cc1cc(Nc2nc(N3CCN(C(=O)C4(NC(=O)OC(C)(C)C)CCC4)CC3)nn3cccc23)n[nH]1] | tert-butyl(1-((4-(4-((5-methyl-1H-pyrazol-3-yl)amino)pyrrolo[2,1-f][1,2,4]triazin-2-yl)-1-piperazinyl)carbonyl)cyclobutyl)carbamate | 2.50 | 496.01 |

TABLE 1-continued

| Ex. No. | Structure | Name | HPLC Ret. time (min) | m/z [M + H] |
|---|---|---|---|---|
| 164 | 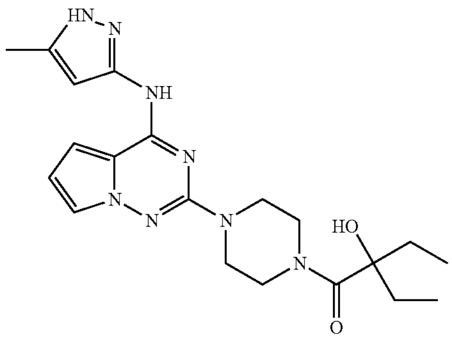 [SMILES: CCC(O)(CC)C(=O)N1CCN(c2nc(Nc3cc(C)[nH]n3)c3cccn3n2)CC1] | 3-((4-(4-((5-methyl-1H-pyrazol-3-yl)amino)pyrrolo[2,1-f][1,2,4]triazin-2-yl)-1-piperazinyl)carbonyl)-3-pentanol | 2.47 | 413.03 |
| 165 | 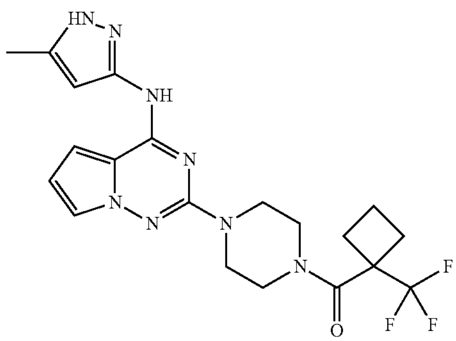 [SMILES: Cc1cc(Nc2nc(N3CCN(C(=O)C4(C(F)(F)F)CCC4)CC3)nn3cccc23)n[nH]1] | N-(5-methyl-1H-pyrazol-3-yl)-2-(4-((1-(trifluoromethyl)cyclobutyl)carbonyl)-1-piperazinyl)pyrrolo[2,1-f][1,2,4]triazin-4-amine | 2.68 | 448.98 |
| 166 | 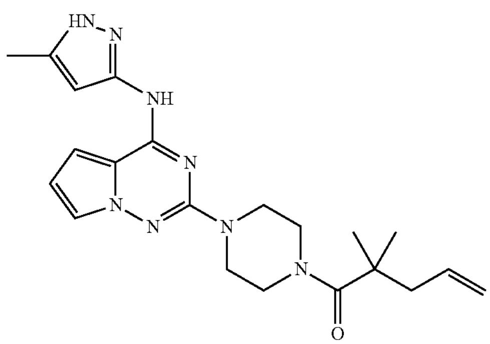 [SMILES: C=CCC(C)(C)C(=O)N1CCN(c2nc(Nc3cc(C)[nH]n3)c3cccn3n2)CC1] | 2-(4-(2,2-dimethyl-4-pentenoyl)-1-piperazinyl)-N-(5-methyl-1H-pyrazol-3-yl)pyrrolo[2,1-f][1,2,4]triazin-4-amine | 2.66 | 409.03 |
| 167 | 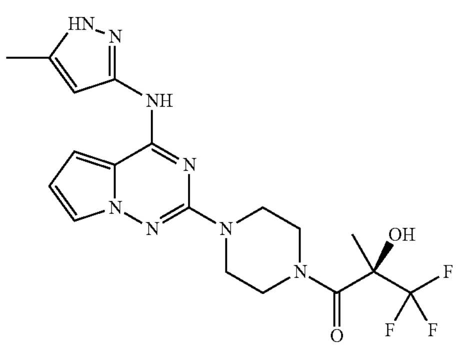 [SMILES: Cc1cc(Nc2nc(N3CCN(C(=O)[C@@](C)(O)C(F)(F)F)CC3)nn3cccc23)n[nH]1] | (2R)-1,1,1-trifluoro-2-methyl-3-(4-(4-((5-methyl-1H-pyrazol-3-yl)amino)pyrrolo[2,1-f][1,2,4]triazin-2-yl)-1-piperazinyl)-3-oxo-2-propanol | 2.47 | 438.94 |

TABLE 1-continued

| Ex. No. | Structure | Name | HPLC Ret. time (min) | m/z [M + H] |
|---|---|---|---|---|
| 168 | 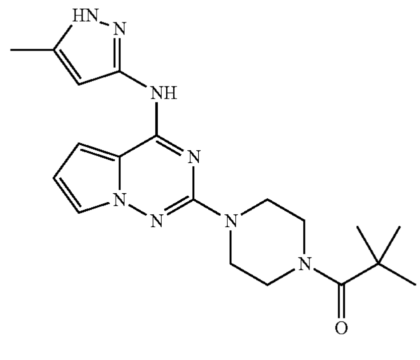 [SMILES: Cc1cc(Nc2nc(N3CCN(C(=O)C(C)(C)C)CC3)nn3cccc23)n[nH]1] | 2-(4-(2,2-dimethylpropanoyl)-1-piperazinyl)-N-(5-methyl-1H-pyrazol-3-yl)pyrrolo[2,1-f][1,2,4]triazin-4-amine | 2.54 | 383.02 |
| 169 | 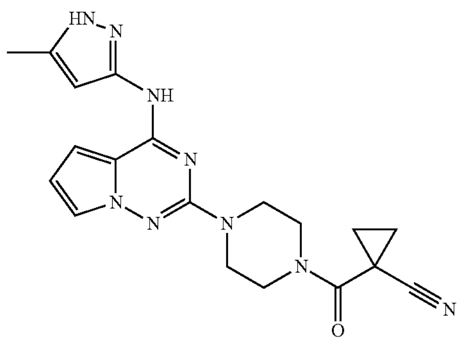 [SMILES: Cc1cc(Nc2nc(N3CCN(C(=O)C4(C#N)CC4)CC3)nn3cccc23)n[nH]1] | 1-((4-(4-((5-methyl-1H-pyrazol-3-yl)amino)pyrrolo[2,1-f][1,2,4]triazin-2-yl)-1-piperazinyl)carbonyl)cyclopropanecarbonitrile | 2.41 | 391.99 |
| 170 | 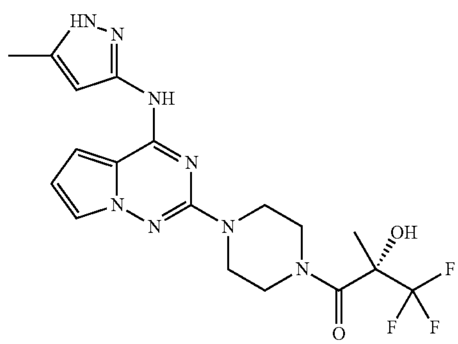 [SMILES: Cc1cc(Nc2nc(N3CCN(C(=O)[C@](C)(O)C(F)(F)F)CC3)nn3cccc23)n[nH]1] | (2S)-1,1,1-trifluoro-2-methyl-3-(4-(4-((5-methyl-1H-pyrazol-3-yl)amino)pyrrolo[2,1-f][1,2,4]triazin-2-yl)-1-piperazinyl)-3-oxo-2-propanol | 2.46 | 438.96 |
| 171 | 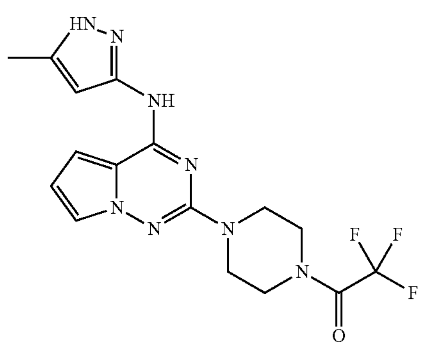 [SMILES: Cc1cc(Nc2nc(N3CCN(C(=O)C(F)(F)F)CC3)nn3cccc23)n[nH]1] | N-(5-methyl-1H-pyrazol-3-yl)-2-(4-(trifluoroacetyl)-1-piperazinyl)pyrrolo[2,1-f][1,2,4]triazin-4-amine | 2.64 | 394.96 |

TABLE 1-continued

| Ex. No. | Structure | Name | HPLC Ret. time (min) | m/z [M + H] |
| --- | --- | --- | --- | --- |
| 172 | 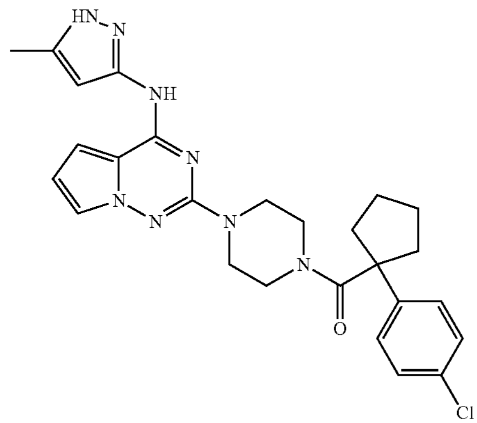 [SMILES: Cc1cc(Nc2nc(N3CCN(C(=O)C4(c5ccc(Cl)cc5)CCCC4)CC3)nn3cccc23)n[nH]1] | 2-(4-((1-(4-chlorophenyl)cyclopentyl)carbonyl)-1-piperazinyl)-N-(5-methyl-1H-pyrazol-3-yl)pyrrolo[2,1-f][1,2,4]triazin-4-amine | 3.10 | 505.01 |
| 173 | 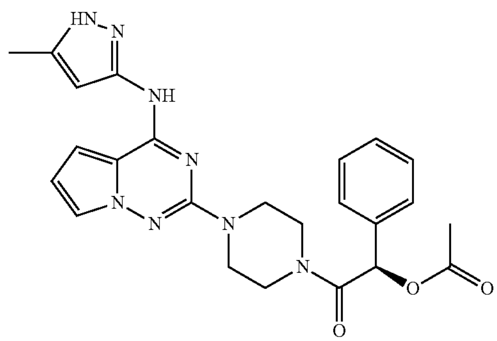 [SMILES: CC(=O)O[C@@H](C(=O)N1CCN(c2nc(Nc3cc(C)[nH]n3)c3cccn3n2)CC1)c1ccccc1] | (1R)-2-(4-(4-((5-methyl-1H-pyrazol-3-yl)amino)pyrrolo[2,1-f][1,2,4]triazin-2-yl)-1-piperazinyl)-2-oxo-1-phenylethyl acetate | 2.50 | 475.03 |
| 174 | 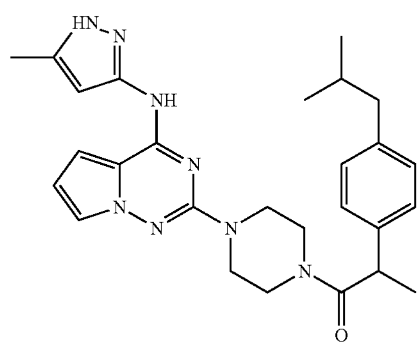 [SMILES: Cc1cc(Nc2nc(N3CCN(C(=O)C(C)c4ccc(CC(C)C)cc4)CC3)nn3cccc23)n[nH]1] | 2-(4-(2-(4-isobutylphenyl)propanoyl)-1-piperazinyl)-N-(5-methyl-1H-pyrazol-3-yl)pyrrolo[2,1-f][1,2,4]triazin-4-amine | 3.09 | 487.09 |
| 175 | 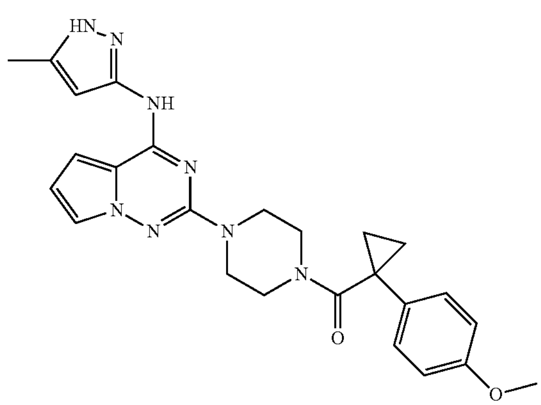 | 2-(4-((1-(4-methoxyphenyl)cyclopropyl)carbonyl)-1-piperazinyl)-N-(5-methyl-1H-pyrazol-3-yl)pyrrolo[2,1-f][1,2,4]triazin-4-amine | 2.59 | 473.03 |

TABLE 1-continued

| Ex. No. | Structure | Name | HPLC Ret. time (min) | m/z [M + H] |
|---|---|---|---|---|
| 176 | 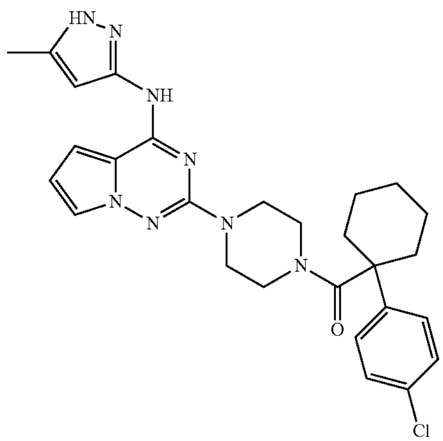 [SMILES: Cc1cc(Nc2nc(N3CCN(C(=O)C4(c5ccc(Cl)cc5)CCCCC4)CC3)nn3cccc23)n[nH]1] | 2-(4-((1-(4-chlorophenyl)cyclohexyl)carbonyl)-1-piperazinyl)-N-(5-methyl-1H-pyrazol-3-yl)pyrrolo[2,1-f][1,2,4]triazin-4-amine | 3.29 | 519.00 |
| 177 | 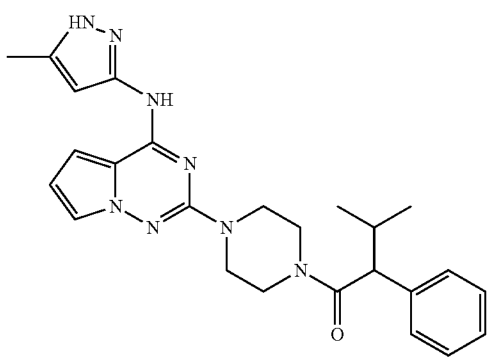 [SMILES: Cc1cc(Nc2nc(N3CCN(C(=O)C(c4ccccc4)C(C)C)CC3)nn3cccc23)n[nH]1] | 2-(4-(3-methyl-2-phenylbutanoyl)-1-piperazinyl)-N-(5-methyl-1H-pyrazol-3-yl)pyrrolo[2,1-f][1,2,4]triazin-4-amine | 2.86 | 459.08 |
| 178 | 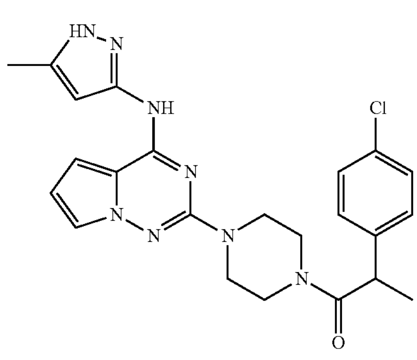 [SMILES: Cc1cc(Nc2nc(N3CCN(C(=O)C(C)c4ccc(Cl)cc4)CC3)nn3cccc23)n[nH]1] | 2-(4-(2-(4-chlorophenyl)propanoyl)-1-piperazinyl)-N-(5-methyl-1H-pyrazol-3-yl)pyrrolo[2,1-f][1,2,4]triazin-4-amine | 2.77 | 465.01 |

TABLE 1-continued

| Ex. No. | Structure | Name | HPLC Ret. time (min) | m/z [M + H] |
|---|---|---|---|---|
| 179 | 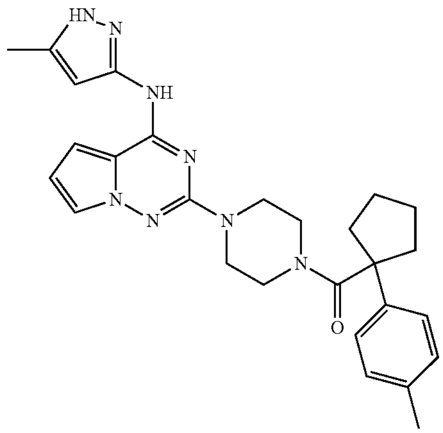 [SMILES: Cc1ccc(C2(C(=O)N3CCN(c4nc(Nc5cc(C)[nH]n5)c5cccn5n4)CC3)CCCC2)cc1] | 2-(4-((1-(4-methylphenyl) cyclopentyl) carbonyl)-1-piperazinyl)-N-(5-methyl-1H-pyrazol-3-yl)pyrrolo[2,1-f][1,2,4]triazin-4-amine | 3.06 | 485.07 |
| 180 | 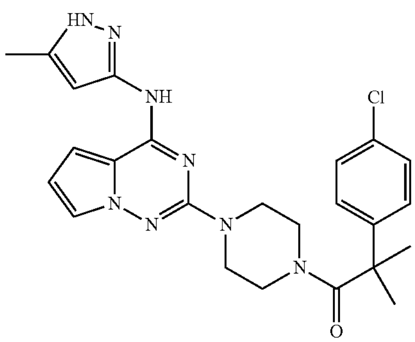 [SMILES: Cc1cc(Nc2nc(N3CCN(C(=O)C(C)(C)c4ccc(Cl)cc4)CC3)nn3cccc23)n[nH]1] | 2-(4-(2-(4-chloro-phenyl)-2-methyl-propanoyl)-1-piperazinyl)-N-(5-methyl-1H-pyrazol-3-yl)pyrrolo[2,1-f][1,2,4]triazin-4-amine | 2.85 | 479.00 |
| 181 | 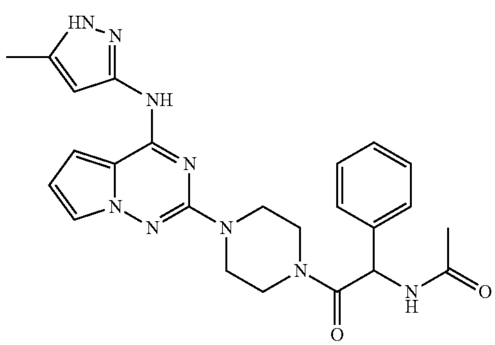 [SMILES: CC(=O)NC(C(=O)N1CCN(c2nc(Nc3cc(C)[nH]n3)c3cccn3n2)CC1)c1ccccc1] | N-(2-(4-(4-((5-methyl-1H-pyrazol-3-yl)amino)pyrrolo[2,1-f][1,2,4]triazin-2-yl)-1-piperazinyl)-2-oxo-1-phenylethyl)acetamide | 2.33 | 474.04 |
| 182 | 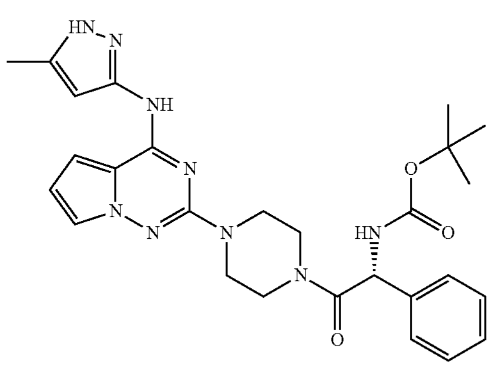 [SMILES: Cc1cc(Nc2nc(N3CCN(C(=O)[C@H](NC(=O)OC(C)(C)C)c4ccccc4)CC3)nn3cccc23)n[nH]1] | tert-butyl((1R)-2-(4-(4-((5-methyl-1H-pyrazol-3-yl)amino)pyrrolo[2,1-f][1,2,4]triazin-2-yl)-1-piperazinyl)-2-oxo-1-phenylethyl carbamate | 2.80 | 532.06 |

| Ex. No. | Structure | Name | HPLC Ret. time (min) | m/z [M + H] |
|---|---|---|---|---|
| 183 | 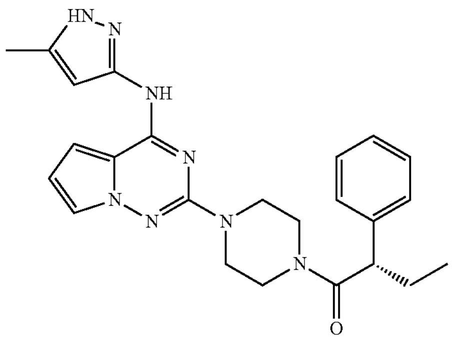 [SMILES: CC[C@H](C(=O)N1CCN(c2nc(Nc3cc(C)[nH]n3)c3cccn3n2)CC1)c1ccccc1] | N-(5-methyl-1H-pyrazol-3-yl)-2-(4-((2S)-2-phenylbutanoyl)-1-piperazinyl)pyrrolo[2,1-f][1,2,4]triazin-4-amine | 2.75 | 445.08 |
| 184 | 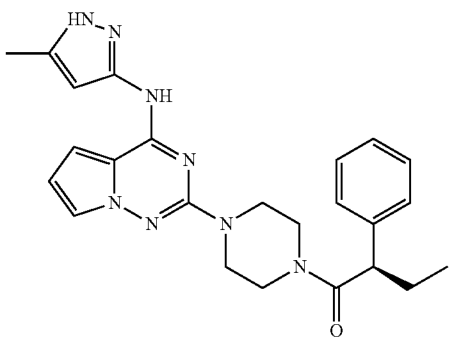 [SMILES: CC[C@@H](C(=O)N1CCN(c2nc(Nc3cc(C)[nH]n3)c3cccn3n2)CC1)c1ccccc1] | N-(5-methyl-1H-pyrazol-3-yl)-2-(4-((2R)-2-phenylbutanoyl)-1-piperazinyl)pyrrolo[2,1-f][1,2,4]triazin-4-amine | 2.75 | 445.07 |
| 185 | 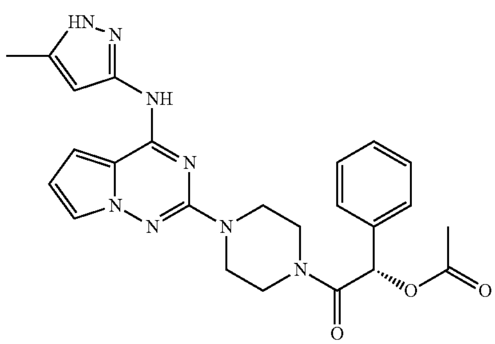 [SMILES: CC(=O)O[C@H](C(=O)N1CCN(c2nc(Nc3cc(C)[nH]n3)c3cccn3n2)CC1)c1ccccc1] | (1S)-2-(4-(4-((5-methyl-1H-pyrazol-3-yl)amino)pyrrolo[2,1-f][1,2,4]triazin-2-yl)-1-piperazinyl)-2-oxo-1-phenylethyl acetate | 2.51 | 475.04 |
| 186 | 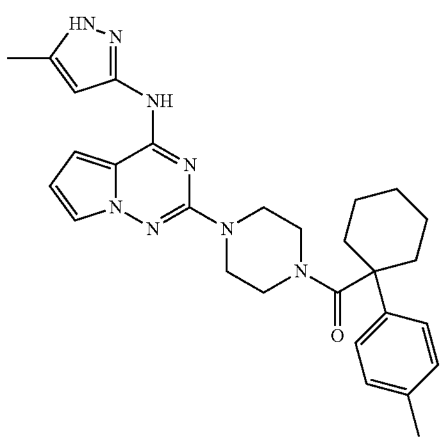 [SMILES: Cc1ccc(C2(C(=O)N3CCN(c4nc(Nc5cc(C)[nH]n5)c5cccn5n4)CC3)CCCCC2)cc1] | 2-(4-((1-(4-methylphenyl)cyclohexyl)carbonyl)-1-piperazinyl)-N-(5-methyl-1H-pyrazol-3-yl)pyrrolo[2,1-f][1,2,4]triazin-4-amine | 3.26 | 499.10 |

TABLE 1-continued

| Ex. No. | Structure | Name | HPLC Ret. time (min) | m/z [M + H] |
|---|---|---|---|---|
| 187 | 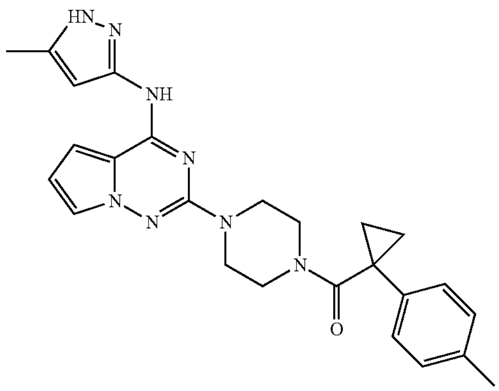 | 2-(4-((1-(4-methylphenyl)cyclopropyl)carbonyl)-1-piperazinyl)-N-(5-methyl-1H-pyrazol-3-yl)pyrrolo[2,1-f][1,2,4]triazin-4-amine | 2.72 | 457.06 |
| 188 | 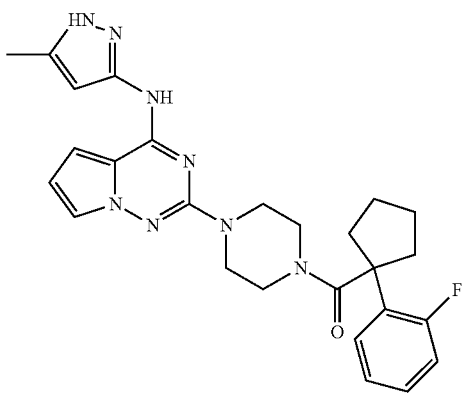 [SMILES: Cc1cc(Nc2nc(N3CCN(C(=O)C4(c5ccccc5F)CCCC4)CC3)nn3cccc23)n[nH]1] | 2-(4-((1-(2-fluorophenyl)cyclopentyl)carbonyl)-1-piperazinyl)-N-(5-methyl-1H-pyrazol-3-yl)pyrrolo[2,1-f][1,2,4]triazin-4-amine | 2.85 | 489.06 |
| 189 | 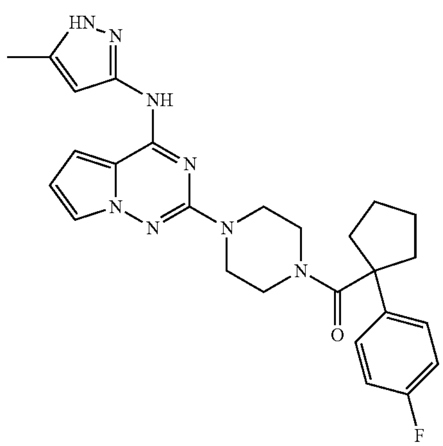 [SMILES: Cc1cc(Nc2nc(N3CCN(C(=O)C4(c5ccc(F)cc5)CCCC4)CC3)nn3cccc23)n[nH]1] | 2-(4-((1-(4-fluorophenyl)cyclopentyl)carbonyl)-1-piperazinyl)-N-(5-methyl-1H-pyrazol-3-yl)pyrrolo[2,1-f][1,2,4]triazin-4-amine | 2.92 | 489.06 |
| 190 | 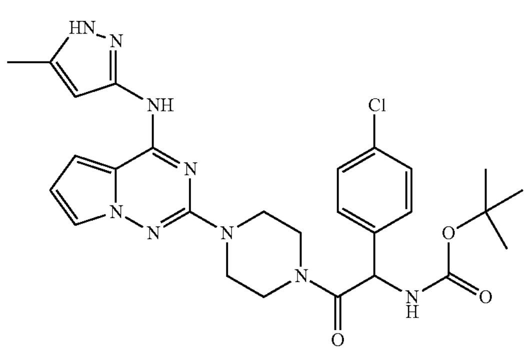 [SMILES: Cc1cc(Nc2nc(N3CCN(C(=O)C(NC(=O)OC(C)(C)C)c4ccc(Cl)cc4)CC3)nn3cccc23)n[nH]1] | tert-butyl(1-(4-chlorophenyl)-2-(4-(4-((5-methyl-1H-pyrazol-3-yl)amino)pyrrolo[2,1-f][1,2,4]triazin-2-yl)-1-piperazinyl)-2-oxoethyl)carbamate | 3.08 | 565.95 |

TABLE 1-continued

| Ex. No. | Structure | Name | HPLC Ret. time (min) | m/z [M + H] |
|---|---|---|---|---|
| 191 | 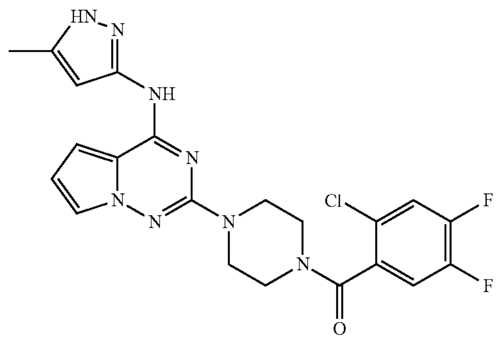 [SMILES: Cc1cc(Nc2nc(N3CCN(C(=O)c4cc(F)c(F)cc4Cl)CC3)nn3cccc23)n[nH]1] | 2-(4-(2-chloro-4,5-difluorobenzoyl)-1-piperazinyl)-N-(5-methyl-1H-pyrazol-3-yl)pyrrolo[2,1-f][1,2,4]triazin-4-amine | 2.78 | 472.91 |
| 192 | 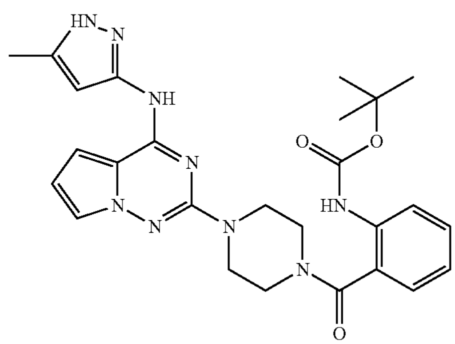 [SMILES: Cc1cc(Nc2nc(N3CCN(C(=O)c4ccccc4NC(=O)OC(C)(C)C)CC3)nn3cccc23)n[nH]1] | tert-butyl(2-((4-(4-((5-methyl-1H-pyrazol-3-yl)amino)pyrrolo[2,1-f][1,2,4]triazin-2-yl)-1-piperazinyl)carbonyl)phenyl)carbamate | 2.86 | 518.00 |
| 193 | 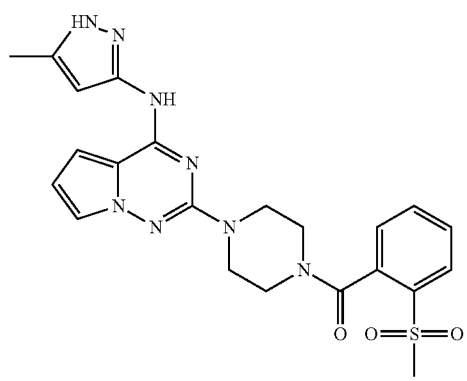 [SMILES: Cc1cc(Nc2nc(N3CCN(C(=O)c4ccccc4S(C)(=O)=O)CC3)nn3cccc23)n[nH]1] | N-(5-methyl-1H-pyrazol-3-yl)-2-(4-(2-(methylsulfonyl)benzoyl)-1-piperazinyl)pyrrolo[2,1-f][1,2,4]triazin-4-amine | 2.45 | 480.95 |
| 194 | 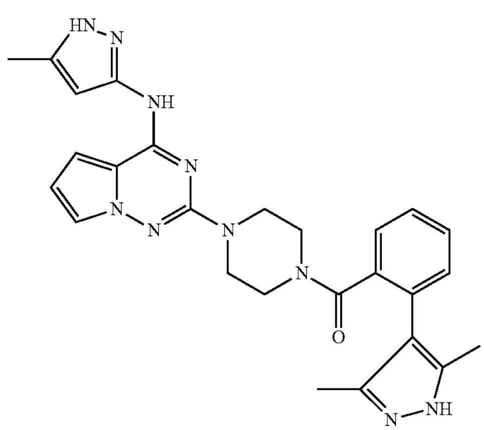 | 2-(4-(2-(3,5-dimethyl-1H-pyrazol-4-yl)benzoyl)-1-piperazinyl)-N-(5-methyl-1H-pyrazol-3-yl)pyrrolo[2,1-f][1,2,4]triazin-4-amine | 2.42 | 497.00 |

TABLE 1-continued

| Ex. No. | Structure | Name | HPLC Ret. time (min) | m/z [M + H] |
|---|---|---|---|---|
| 195 | 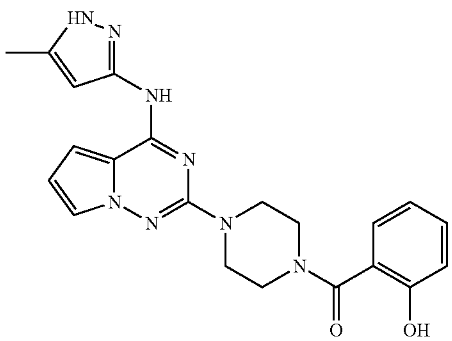 [SMILES: Cc1cc(Nc2nc(N3CCN(C(=O)c4ccccc4O)CC3)nn3cccc23)n[nH]1] | 2-((4-(4-((5-methyl-1H-pyrazol-3-yl)amino)pyrrolo[2,1-f][1,2,4]triazin-2-yl)-1-piperazinyl)carbonyl)phenol | 2.37 | 419.03 |
| 196 | 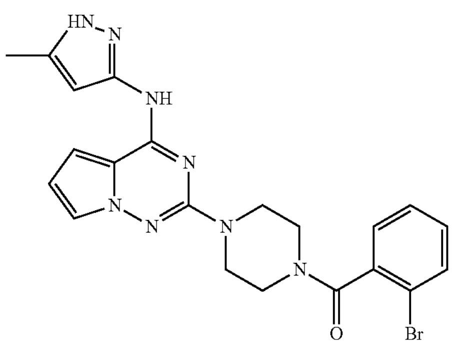 [SMILES: Cc1cc(Nc2nc(N3CCN(C(=O)c4ccccc4Br)CC3)nn3cccc23)n[nH]1] | 2-(4-(2-bromobenzoyl)-1-piperazinyl)-N-(5-methyl-1H-pyrazol-3-yl)pyrrolo[2,1-f][1,2,4]triazin-4-amine | 2.59 | 480.89 |
| 197 | 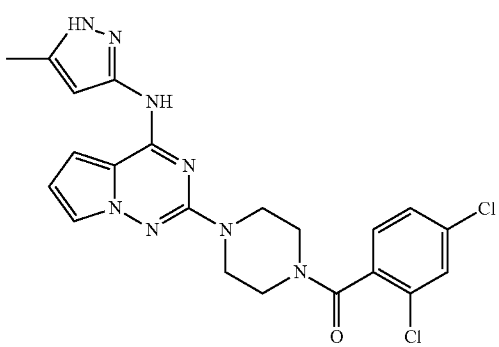 [SMILES: Cc1cc(Nc2nc(N3CCN(C(=O)c4ccc(Cl)cc4Cl)CC3)nn3cccc23)n[nH]1] | 2-(4-(2,4-dichlorobenzoly)-1-piperazinyl)-N-(5-methyl-1H-pyrazol-3-yl)pyrrolo[2,1-f][1,2,4]triazin-4-amine | 2.78 | 470.91 |
| 198 | 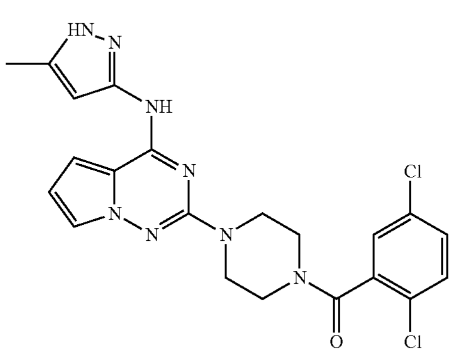 [SMILES: Cc1cc(Nc2nc(N3CCN(C(=O)c4cc(Cl)ccc4Cl)CC3)nn3cccc23)n[nH]1] | 2-(4-(2,5-dichlorobenzoyl)-1-piperazinyl)-N-(5-methyl-1H-pyrazol-3-yl)pyrrolo[2,1-f][1,2,4]triazin-4-amine | 2.73 | 470.92 |

TABLE 1-continued

| Ex. No. | Structure | Name | HPLC Ret. time (min) | m/z [M + H] |
|---|---|---|---|---|
| 199 | 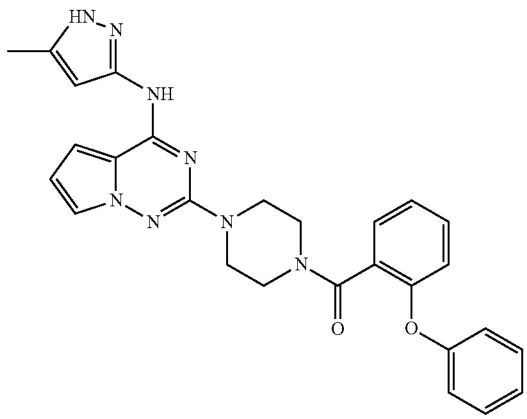 [SMILES: Cc1cc(Nc2nc(N3CCN(C(=O)c4ccccc4Oc4ccccc4)CC3)nn3cccc23)n[nH]1] | N-(5-methyl-1H-pyrazol-3-yl)-2-(4-(2-phenoxybenzoyl)-1-piperazinyl)pyrrolo[2,1-f][1,2,4]triazin-4-amine | 2.73 | 495.00 |
| 200 | 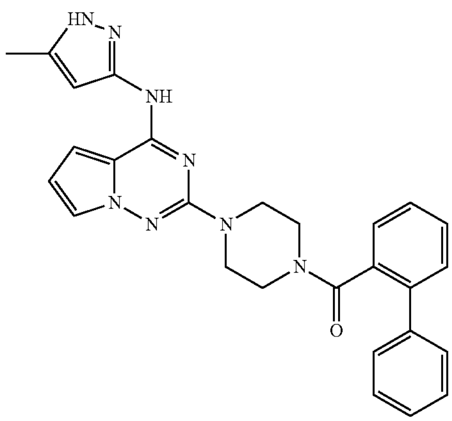 [SMILES: Cc1cc(Nc2nc(N3CCN(C(=O)c4ccccc4-c4ccccc4)CC3)nn3cccc23)n[nH]1] | 2-(4-(2-biphenylylcarbonyl)-1-piperazinyl)-N-(5-methyl-1H-pyrazol-3-yl)pyrrolo[2,1-f][1,2,4]triazin-4-amine | 2.72 | 479.04 |
| 201 | 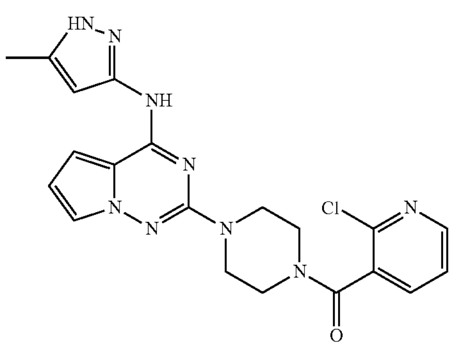 [SMILES: Cc1cc(Nc2nc(N3CCN(C(=O)c4cccnc4Cl)CC3)nn3cccc23)n[nH]1] | 2-(4-((2-chloro-3-pyridinyl)carbonyl)-1-piperazinyl)-N-(5-methyl-1H-pyrazol-3-yl)pyrrolo[2,1-f][1,2,4]triazin-4-amine | 2.35 | 438.02 |
| 202 | 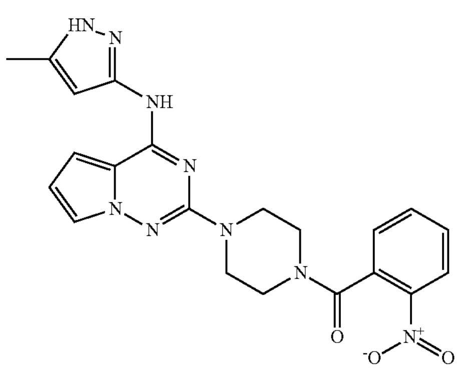 | N-(5-methyl-1H-pyrazol-3-yl)-2-(4-(2-nitrobenzoyl)-1-piperazinyl)pyrrolo[2,1-f][1,2,4]triazin-4-amine | 2.47 | 447.99 |

TABLE 1-continued

| Ex. No. | Structure | Name | HPLC Ret. time (min) | m/z [M + H] |
|---|---|---|---|---|
| 203 | 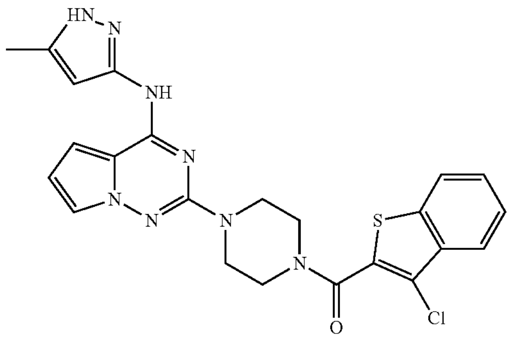 [SMILES: Cc1cc(Nc2nc(N3CCN(C(=O)c4sc5ccccc5c4Cl)CC3)nn3cccc23)n[nH]1] | 2-(4-((3-chloro-1-benzothiophen-2-yl)carbonyl)-1-piperazinyl)-N-(5-methyl-1H-pyrazol-3-yl)pyrrolo[2,1-f][1,2,4]triazin-4-amine | 2.88 | 492.93 |
| 204 | 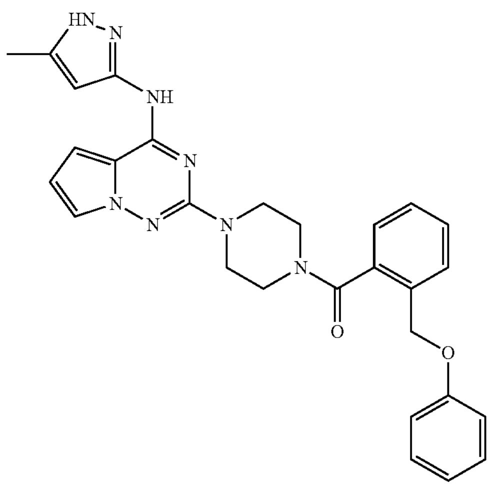 [SMILES: Cc1cc(Nc2nc(N3CCN(C(=O)c4ccccc4COc4ccccc4)CC3)nn3cccc23)n[nH]1] | N-(5-methyl-1H-pyrazol-3-yl)-2-(4-(2-(phenoxymethyl)benzoyl)-1-piperazinyl)pyrrolo[2,1-f][1,2,4]triazin-4-amine | 2.80 | 509.05 |
| 205 | 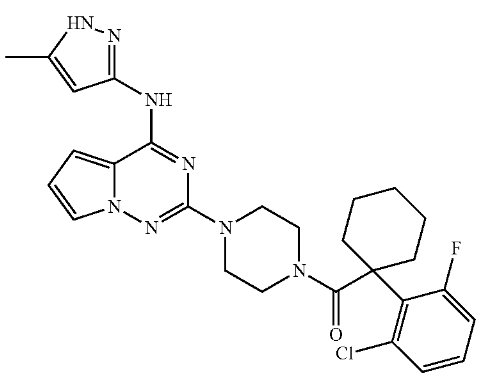 [SMILES: Cc1cc(Nc2nc(N3CCN(C(=O)C4(c5c(F)cccc5Cl)CCCCC4)CC3)nn3cccc23)n[nH]1] | 2-(4-((1-(2-chloro-6-fluorophenyl)cyclohexyl)carbonyl)-1-piperazinyl)-N-(5-methyl-1H-pyrazol-3-yl)pyrrolo[2,1-f][1,2,4]triazin-4-amine | 2.95 | 536.87 |

TABLE 1-continued

| Ex. No. | Structure | Name | HPLC Ret. time (min) | m/z [M + H] |
|---|---|---|---|---|
| 206 | 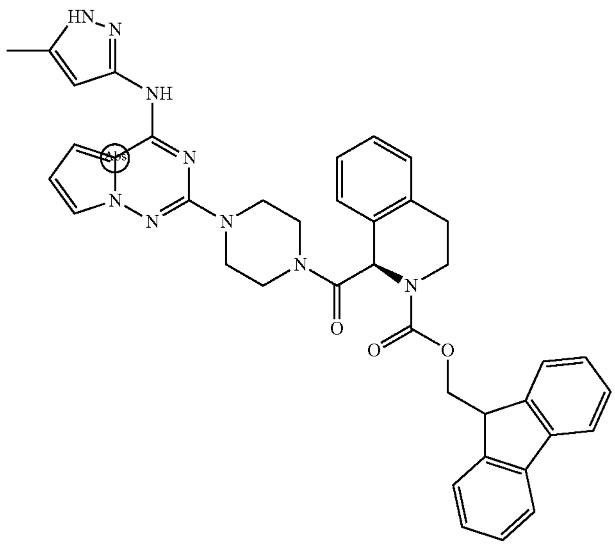 [SMILES: Cc1cc(Nc2nc(N3CCN(C(=O)[C@H]4c5ccccc5CCN4C(=O)OCC4c5ccccc5-c5ccccc54)CC3)nn3cccc23)n[nH]1] | 9H-fluoren-9-ylmethyl (1R)-1-((4-(4-((5-methyl-1H-pyrazol-3-yl)amino)pyrrolo[2,1-f][1,2,4]triazin-2-yl)-1-piperazinyl)carbonyl)-3,4-dihydro-2(1H)-isoquinolinecarboxylate | 2.97 | 680.00 |
| 207 | 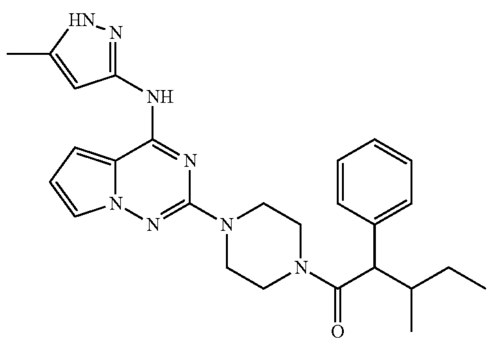 [SMILES: CCC(C)C(C(=O)N1CCN(c2nc(Nc3cc(C)[nH]n3)c3cccn3n2)CC1)c1ccccc1] | 2-(4-(3-methyl-2-phenylpentanoyl)-1-piperazinyl)-N-(5-methyl-1H-pyrazol-3-yl)pyrrolo[2,1-f][1,2,4]triazin-4-amine | 2.71 | 472.95 |
| 208 | 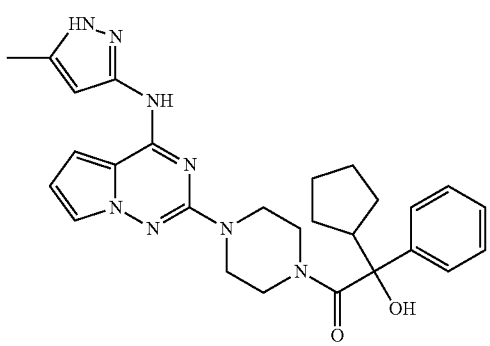 [SMILES: Cc1cc(Nc2nc(N3CCN(C(=O)C(O)(c4ccccc4)C4CCCC4)CC3)nn3cccc23)n[nH]1] | 1-cyclopentyl-2-(4-(4-((5-methyl-1H-pyrazol-3-yl)amino)pyrrolo[2,1-f][1,2,4]triazin-2-yl)-1-piperazinyl)-2-oxo-1-phenylethanol | 2.63 | 500.92 |
| 209 | 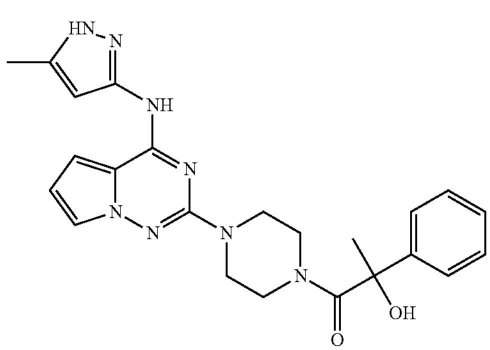 [SMILES: Cc1cc(Nc2nc(N3CCN(C(=O)C(C)(O)c4ccccc4)CC3)nn3cccc23)n[nH]1] | 1-(4-(4-((5-methyl-1H-pyrazol-3-yl)amino)pyrrolo[2,1-f][1,2,4]triazin-2-yl)-1-piperazinyl)-1-oxo-2-phenyl-2-propanol | 2.00 | 446.88 |

TABLE 1-continued

| Ex. No. | Structure | Name | HPLC Ret. time (min) | m/z [M + H] |
|---|---|---|---|---|
| 210 | 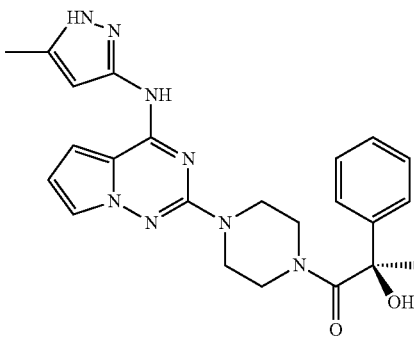 [SMILES: Cc1cc(Nc2nc(N3CCN(C(=O)[C@](C)(O)c4ccccc4)CC3)nn3cccc23)n[nH]1] | (2R)-1-(4-(4-((5-methyl-1H-pyrazol-3-yl)amino)pyrrolo[2,1-f][1,2,4]triazin-2-yl)-1-piperazinyl)-1-oxo-2-phenyl-2-propanol | 2.01 | 446.89 |
| 211 | 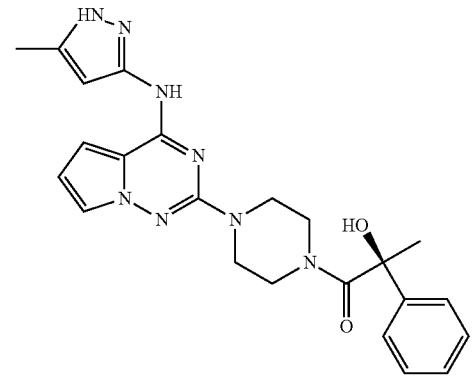 [SMILES: Cc1cc(Nc2nc(N3CCN(C(=O)[C@@](C)(O)c4ccccc4)CC3)nn3cccc23)n[nH]1] | (2S)-1-(4-(4-((5-methyl-1H-pyrazol-3-yl)amino)pyrrolo[2,1-f][1,2,4]triazin-2-yl)-1-piperazinyl)-1-oxo-2-phenyl-2-propanol | 2.01 | 446.89 |
| 212 | 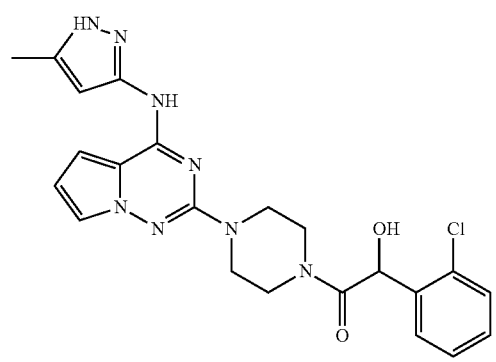 [SMILES: Cc1cc(Nc2nc(N3CCN(C(=O)C(O)c4ccccc4Cl)CC3)nn3cccc23)n[nH]1] | 1-(2-chlorophenyl)-2-(4-(4-((5-methyl-1H-pyrazol-3-yl)amino)pyrrolo[2,1-f][1,2,4]triazin-2-yl)-1-piperazinyl)-2-oxoethanol | 2.01 | 466.81 |
| 213 | 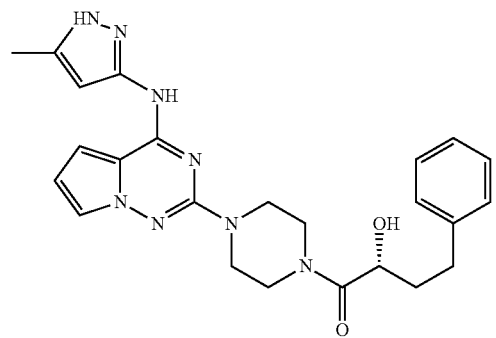 [SMILES: Cc1cc(Nc2nc(N3CCN(C(=O)[C@H](O)CCc4ccccc4)CC3)nn3cccc23)n[nH]1] | (2R)-1-(4-(4-((5-methyl-1H-pyrazol-3-yl)amino)pyrrolo[2,1-f][1,2,4]triazin-2-yl)-1-piperazinyl)-1-oxo-4-phenyl-2-butanol | 2.10 | 460.89 |

TABLE 1-continued

| Ex. No. | Structure | Name | HPLC Ret. time (min) | m/z [M + H] |
|---|---|---|---|---|
| 214 | 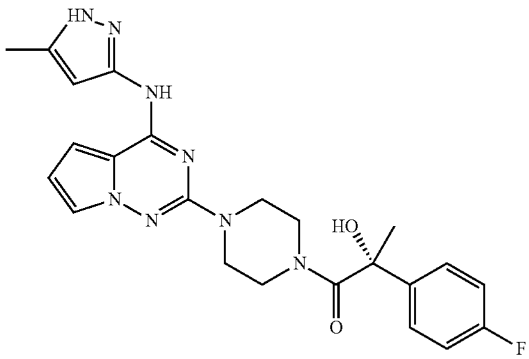 [SMILES: Cc1cc(Nc2nc(N3CCN(C(=O)[C@](C)(O)c4ccc(F)cc4)CC3)nn3cccc23)n[nH]1] | (2R)-2-(4-fluorophenyl)-1-(4-(4-((5-methyl-1H-pyrazol-3-yl)amino)pyrrolo[2,1-f][1,2,4]triazin-2-yl)-1-piperazinyl)-1-oxo-2-propanol | 2.07 | 464.87 |
| 215 | 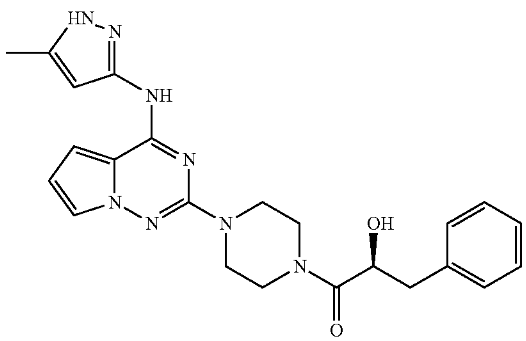 [SMILES: Cc1cc(Nc2nc(N3CCN(C(=O)[C@@H](O)Cc4ccccc4)CC3)nn3cccc23)n[nH]1] | (2S)-1-(4-(4-((5-methyl-1H-pyrazol-3-yl)amino)pyrrolo[2,1-f][1,2,4]triazin-2-yl)-1-piperazinyl)-1-oxo-3-phenyl-2-propanol | 1.92 | 446.91 |
| 216 | 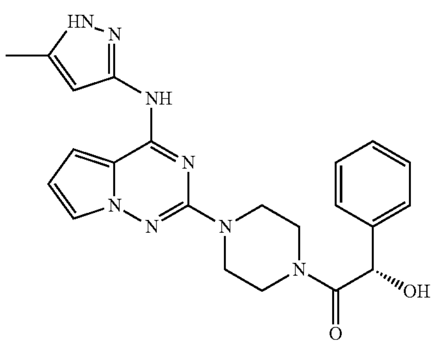 [SMILES: Cc1cc(Nc2nc(N3CCN(C(=O)[C@@H](O)c4ccccc4)CC3)nn3cccc23)n[nH]1] | (1S)-2-(4-(4-((5-methyl-1H-pyrazol-3-yl)amino)pyrrolo[2,1-f][1,2,4]triazin-2-yl)-1-piperazinyl)-2-oxo-1-phenylethanol | 1.85 | 432.91 |
| 217 | 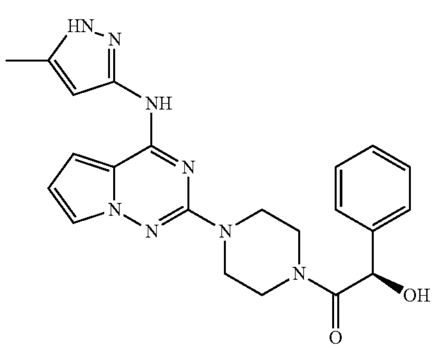 [SMILES: Cc1cc(Nc2nc(N3CCN(C(=O)[C@H](O)c4ccccc4)CC3)nn3cccc23)n[nH]1] | (1R)-2-(4-(4-((5-methyl-1H-pyrazol-3-yl)amino)pyrrolo[2,1-f][1,2,4]triazin-2-yl)-1-piperazinyl)-2-oxo-1-phenylethanol | 1.85 | 432.88 |

TABLE 1-continued

| Ex. No. | Structure | Name | HPLC Ret. time (min) | m/z [M + H] |
|---|---|---|---|---|
| 218 | 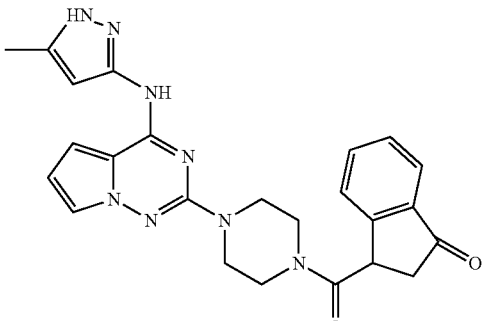 | 3-((4-(4-((5-methyl-1H-pyrazol-3-yl)amino)pyrrolo[2,1-f][1,2,4]triazin-2-yl)-1-piperazinyl)carbonyl)-1-indanone | 1.83 | 456.87 |
| 219 | 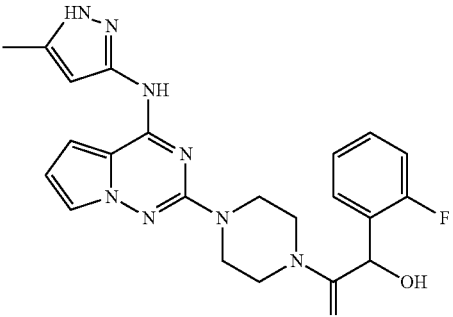 | 1-(2-fluorophenyl)-2-(4-(4-((5-methyl-1H-pyrazol-3-yl)amino)pyrrolo[2,1-f][1,2,4]triazin-2-yl)-1-piperazinyl)-2-oxoethanol | 1.89 | 450.87 |
| 220 | 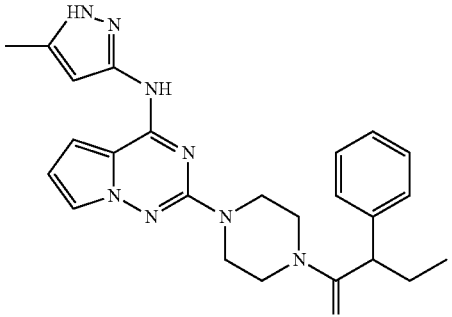 | N-(5-methyl-1H-pyrazol-3-yl)-2-(4-(2-phenylbutanoyl)-1-piperazinyl)pyrrolo[2,1-f][1,2,4]triazin-4-amine | 2.37 | 444.94 |
| 221 | 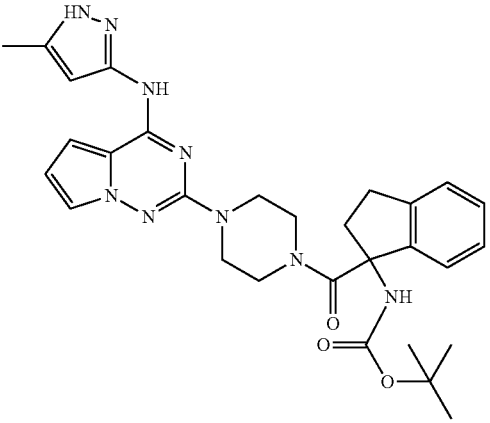 [SMILES: Cc1cc(Nc2nc(N3CCN(C(=O)C4(NC(=O)OC(C)(C)C)CCc5ccccc54)CC3)nn3cccc23)n[nH]1] | tert-butyl(1-((4-(4-((5-methyl-1H-pyrazol-3-yl)amino)pyrrolo[2,1-f][1,2,4]triazin-2-yl)-1-piperazinyl)carbonyl)-2,3-dihydro-1H-inden-1-yl)carbamate | 2.43 | 557.93 |

HPLC Conditions:
(c) YMC S5 Combiscreen ODS 4.6 × 50 mm, 10-90% aqueous methanol containing 0.2% $H_3PO_4$, 4 min gradient, monitored at 220 or 254 nm)
(d) Chromolith SpeedROD 4.6 × 50 mm, 10-90% aqueous methanol containing 0.1% TFA, 4 min gradient, monitored at 220 or 254 nm)

Example 252

(R)-1-(3-methyl-4-(4-(5-methyl-1H-pyrazol-3-ylamino)pyrrolo[1,2-f][1,2,4]triazin-2-yl)piperazin-1-yl)-2-phenylethanone

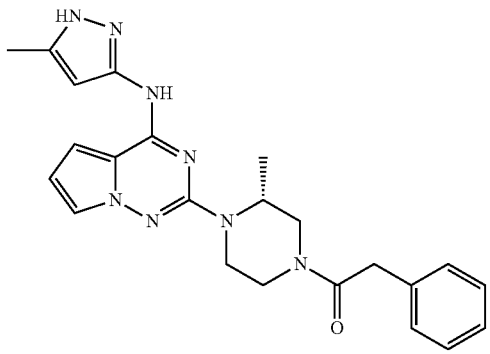 [SMILES: Cc1cc(Nc2nc(N3CCN(C(=O)Cc4ccccc4)C[C@H]3C)nn3cccc23)n[nH]1]

252A Preparation of (R)—N-(5-methyl-1H-pyrazol-3-yl)-2-(2-methylpiperazin-1-yl)pyrrolo[1,2-f][1,2,4]triazin-4-amine To 2-chloro-N-(5-methyl-1H-pyrazol-3-yl)pyrrolo[1,2-f][1,2,4]triazin-4-amine (100 mg, 0.402 mmol) and (R)-tert-butyl 3-methylpiperazine-1-carboxylate (965 mg, 4.82 mmol) in NMP (1 mL) in a vial was added DIPEA (0.211 mL, 1.206 mmol). The reaction was heated at 160° C. overnight. The reaction was cooled, diluted with MeOH and purified by prep HPLC (YMC ODS S5 30×100 mm, 10% MeOH to 90% MeOH/H2O with 0.1% TFA, 15 min, 20 ml/min flow rate). The residue obtained after concentration of fractions was treated with a 1:1 mixture of TFA/CH2Cl2 (4 ml) and stirred at RT for 30 min. The reaction mixture was concentrated to afford 47.3 mg of (R)—N-(5-methyl-1H-pyrazol-3-yl)-2-(2-methylpiperazin-1-yl)pyrrolo[1,2-f][1,2,4]triazin-4-amine.

252B Preparation of (R)-1-(3-methyl-4-(4-(5-methyl-1H-pyrazol-3-ylamino)pyrrolo[1,2-f][1,2,4]triazin-2-yl)piperazin-1-yl)-2-phenylethanone The (R)—N-(5-methyl-1H-pyrazol-3-yl)-2-(2-methylpiperazin-1-yl)pyrrolo[1,2-f][1,2,4]triazin-4-amine was dissolved in dichloromethane (2 mL) and cooled to 0° C. 2-phenylacetyl chloride (0.022 mL, 0.166 mmol) and DIPEA (0.087 mL, 0.497 mmol) were added and the reaction brought to RT and stirred for overnight. The solvent was removed in vacuo and remaining oil diluted with MeOH. 4 drops of 1N aqueous NaOH was added, and reaction stirred for 45 min. The reaction mixture was acidified with aqueous 1N HCl and purified by prep HPLC(YMC ODS S5 30×100 mm, 10% MeOH to 90% MeOH/H2O with 0.1% TFA, 15 min, 20 ml/min flow rate). To afford 20.7 g of (R)-1-(3-methyl-4-(4-(5-methyl-1H-pyrazol-3-ylamino)pyrrolo[1,2-f][1,2,4]triazin-2-yl)piperazin-1-yl)-2-phenylethanone, TFA.

m/z=431.2 (M+H)

1H NMR (CD$_3$OD) δ ppm 7.57-7.61 (m, 1H), 7.15-7.22 (m, J=9.07, 9.07, 5.50 Hz, 2H), 7.01 (ddd, J=11.41, 8.39, 2.75 Hz, 1H), 6.88-6.94 (m, 1H), 6.65-6.67 (m, 1H), 6.21 (s, 1H), 5.12-5.17 (m, J=1.65 Hz, 1H), 3.75-3.88 (m, 4H), 2.29-2.41 (m, 5H)

The invention claimed is:

1. A compound of formula I

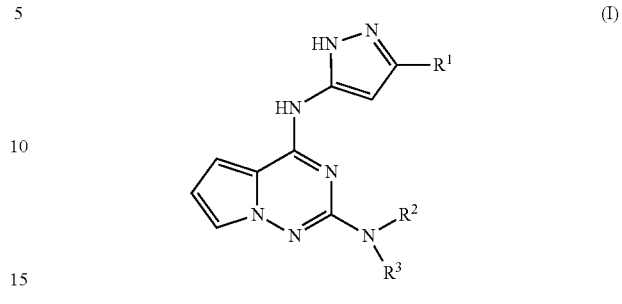

wherein:

$R^1$ is hydrogen, $C_{1-6}$ alkyl substituted with 0-3 $R^a$, $C_{3-6}$ cycloalkyl substituted with 0-3 $R^a$, $C_{6-10}$ aryl substituted with 0-3 $R^a$, or —CONR$^{12}$R$^{13}$;

$R^2$ and $R^3$ are taken together with the nitrogen atom to which they are attached to form a piperazinyl or diazabicyclo[2.2.1]heptanyl ring; the ring being substituted with at least one of —COR$^{14}$, —C(O)—C(O)—R$^{14}$, or —SO$_2$R$^{14}$, said ring also being substituted with 0-3 $R^a$;

$R^7$ and $R^8$ are independently hydrogen, $C_{1-6}$ alkyl, $C_{3-6}$ cycloalkyl, or (CH$_2$)$_r$-phenyl; alternatively $R^7$ and $R^8$, along with nitrogen atom to which they are attached, join to form a 5-10 membered heterocyclic ring;

$R^{12}$ and $R^{13}$ are independently hydrogen, $C_{1-6}$ alkyl optionally substituted with $R^a$, $C_{3-6}$ cycloalkyl optionally substituted with $R^a$, $C_{6-10}$ aryl substituted with 0-3 $R^a$, or a 5-10 membered heterocyclic system containing 1-4 heteroatoms selected from N, O, and S, substituted with 0-3 $R^a$; or alternatively, $R^{12}$ and $R^{13}$ are taken together with the nitrogen atom to which they are attached to form an 4-8 membered ring, the ring optionally containing one or more additional heteroatoms selected from —N—, —S— and —O—; the ring being substituted with 0-1 of hydrogen, —OH, or $C_{1-6}$ alkyl optionally substituted with 0-5 $R^a$;

$R^{14}$ is hydrogen, $C_{1-6}$ alkyl substituted with 0-3 $R^{14}$a, $C_{1-6}$ alkenyl substituted with 0-3 $R^{14a}$, $C_{1-6}$ alkynyl substituted with 0-3 $R^{14a}$, $C_{1-6}$ haloalkyl, (CHR)$_r$—C$_{36}$ cycloalkyl substitute with 0-3 $R^{14a}$, bicyclo[4.2.0]octatrienyl substituted with 0-3 $R^{14a}$, indenyl substituted with 0-3 $R^{14a}$, indanonyl substituted with 0-3 $R^{14a}$; —(CH$_2$)$_r$—C$_{6-10}$ aryl substituted with 0-5 $R^{14a}$, or —(CH$_2$)$_r$-5-10 membered heterocyclic system containing 1-4 heteroatoms selected from N, O, and S, substituted with 0-3 $R^{14a}$, $R^{14a}$ is F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^7$R$^8$, —(CH$_2$)$_r$C(O)NR$^7$R$^8$, —(CH$_2$)$_r$NR$^b$C(O)R$^b$, —(CH$_2$)$_r$NR$^b$C(O)OR$^c$, —NR$^b$C(O)NR$^7$R$^8$, —S(O)$_p$NR$^7$R$^8$, —NR$^b$S(O)$_p$R$^c$, —S(O)R$^c$, —S(O)$_2$R$^c$, $C_{1-6}$ alkyl substituted with 0-1 $R^a$, $C_{1-6}$ alkenyl substituted with 0-1 $R^a$, $C_{1-6}$ alkynyl substituted with 0-1 $R^a$, $C_{1-6}$ haloalkyl, a —(CH$_2$)$_r$-3-14 membered carbocycle optionally substituted with 0-2 $R^a$, or a —(CH$_2$)$_r$-5-7 membered heterocycle comprising carbon atoms and 1-4 heteroatoms selected from N, O, and S(O)$_p$, wherein said heterocycle is substituted with 0-2 $R^a$;

$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^c$, —$(CH_2)_rNR^bC(O)OR^c$, —$NR^bC(O)NR^7R^8$, —$S(O)_pNR^7R^8$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle, or —$(CH_2)_2$-5-7 membered heterocycle comprising carbon atoms and 1-4 heteroatoms selected from N, O, and $S(O)_p$;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, OCF3, CF3, CN, $NO_2$, —$OR^e$, —(CH2)rC(O)Rb, —$NR^eR^e$, —$NR^eC(O)OR^e$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

R, at each occurrence, is independently from H, $C_{1-6}$ alkyl, $(CH_2)_rC_{3-6}$ cycloalkyl, or $(CH_2)_r$phenyl;

p is 0, 1, or 2; and r is 0, 1, 2, 3, or 4;

or a pharmaceutically acceptable salt or stereoisomer thereof.

2. A compound according to claim 1 wherein:

$R^2$ and $R^3$ are taken together with the nitrogen atom to which they are attached to form the ring, the ring is:

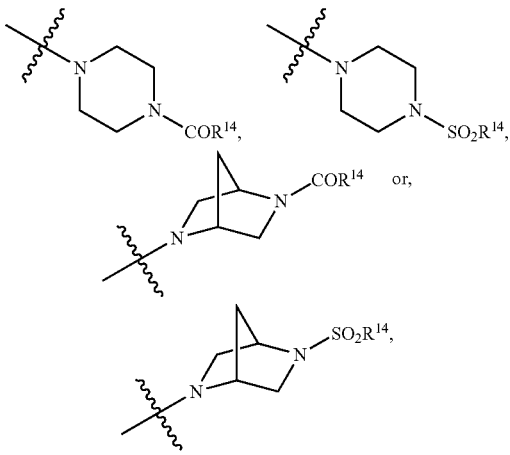

the ring also being substituted with 0-2 $R^a$.

3. A compound according to claim 2 wherein:

$R^1$ is hydrogen, $C_{1-4}$ alkyl, $C_{3-6}$ cycloalkyl substituted 0-1 $R^a$, or —$CONR^{12}R^{13}$; $R^{12}$ and $R^{13}$ are hydrogen, $C_{1-6}$ alkyl, or $C_{3-6}$ cycloalkyl.

4. A compound according to claim 3 wherein:

$R^7$ and $R^8$ are independently hydrogen, $C_{1-6}$ alkyl, $C_{3-6}$ cycloalkyl, or $(CH_2)_r$-phenyl.

5. A compound according to claim 1 wherein $R^{14}$ is hydrogen, $C_{1-6}$ alkyl substituted with 0-3 $R^{14a}$; $C_{1-6}$ alkenyl substituted with 0-3 $R^{14a}$; $(CHR)_r$—$C_{3-6}$ cycloalkyl substitute with 0-3 $R^{14a}$, wherein the cycloalkyl is cyclopropyl, cyclobutyl, cyclopentyl or cyclohexyl; —$(CH_2)_r$—$C_{6-10}$ aryl substituted with 0-5 $R^{14a}$, wherein the aryl is phenyl; bicyclo[4.2.0]octatrienyl substituted with 0-3 $R^{14a}$, indenyl substituted with 0-3 $R^{14a}$, indanonyl substituted with 0-3 $R^{14a}$, or —$(CH_2)_r$-5-10 membered heterocyclic system containing 1-4 heteroatoms selected from N, O, and S, substituted with 0-3 $R^{14a}$, $R^{14a}$ is F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^7R^8$, —$(CH_2)_rC(O)NR^7R^8$, —$(CH_2)_rNR^bC(O)R^b$, —$(CH_2)_rNR^bC(O)OR^c$, —$NR^bC(O)NR^7R^8$, —$S(O)_pNR^7R^8$, —$NR^bS(O)_pR^c$, —$S(O)R^c$, —$S(O)_2R^c$, $C_{1-6}$ alkyl substituted with 0-1 $R^a$, $C_{1-6}$ alkynyl substituted with 0-1 $R^a$, $C_{1-6}$ haloalkyl, a —$(CH_2)_r$-3-14 membered carbocycle optionally substituted with 0-2 $R^a$, wherein the carbocyclic residue is cyclopropyl, cyclopentyl, cyclohexyl, fluorenyl, or phenyl, or a —$(CH_2)_r$-5-7 membered heterocycle comprising carbon atoms and 1-4 heteroatoms selected from N, O, and $S(O)_p$, wherein said heterocycle is substituted with 0-2 $R^a$, wherein the heterocycle is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl.

6. A compound according to claim 1 wherein r is 0, 1, or 2.

7. A compound according to claim 6 wherein $R^{14}$ is hydrogen, $C_{1-6}$ alkyl substituted with 0-3 $R^{14}$a; $C_{1-6}$ alkenyl; $(CHR)_r$—$C_{3-6}$ cycloalkyl substitute with 0-3 $R^{14a}$, wherein the cycloalkyl is cyclobutyl, cyclopentyl or cyclohexyl; —$(CH_2)_r$—$C_{6-10}$ aryl substituted with 0-5 $R^{14a}$, wherein the aryl is phenyl, bicyclo[4.2.0]octatrienyl, indenyl, indanonyl; or —$(CH_2)_r$-heterocyclic system containing 1-4 heteroatoms selected from N, O, and S, substituted with 0-3 $R^{14a}$, wherein the heterocyclic system is pyridyl, pyridinyl, piperidinyl isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl, $R^{14a}$ is F, Cl, Br, $OCF_3$, $CF_3$, $CHF_2$, CN, $NO_2$, —$(CH_2)_rOR^b$, —$C(O)R^b$, —$C(O)OR^b$, —$OC(O)R^b$, —$(CH_2)_rNR^7R^8$, —$C(O)NR^7R^8$, —$NR^bC(O)R^b$, —$NR^bC(O)OR^c$, —$C(O)NR^7R^8$, —$S(O)_pNR^7R^8$, —$NR^bS(O)_pR^c$, —$S(O)R^c$, —$S(O)_2R^c$, $C_{1-6}$ alkyl substituted with 0-1 $R^a$, —C≡CH, $C_{1-2}$ haloalkyl, a —$(CH_2)_r$-3-7 membered carbocycle optionally substituted with 0-2 $R^a$, wherein the carbocyclic residue is cyclopropyl, cyclopentyl, cyclohexyl, fluorenyl, or phenyl, or a —$(CH_2)_r$-5-7 membered heterocycle comprising carbon atoms and 1-4 heteroatoms selected from N, O, and $S(O)_p$, wherein said heterocycle is substituted with 0-2 $R^a$, wherein the heterocycle is pyridyl, pyridinyl, isoxazyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl.

8. A compound according to claim 2 wherein:

$R^2$ and $R^3$ are taken together with the nitrogen atom to which they are attached to form the ring, the ring is:

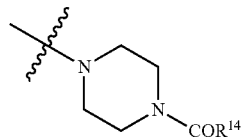

the ring also being substituted with 0-1 $R^a$.

9. A compound according to claim 3 wherein $R^1$ is methyl or cyclopropyl substituted with 0-1 methyl or trifluoromethyl.

10. A pharmaceutical composition comprising one or more compounds of claim 1 and a pharmaceutically acceptable carrier.

* * * * *